United States Patent
Firminger et al.

(10) Patent No.: US 8,103,613 B2
(45) Date of Patent: *Jan. 24, 2012

(54) HYPOTHESIS BASED SOLICITATION OF DATA INDICATING AT LEAST ONE OBJECTIVE OCCURRENCE

(75) Inventors: Shawn P. Firminger, Redmond, WA (US); Jason Garms, Redmond, WA (US); Edward K.Y. Jung, Bellevue, WA (US); Chris D. Karkanias, Sammamish, WA (US); Eric C. Leuthardt, St. Louis, MO (US); Royce A. Levien, Lexington, MA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Kristin M. Tolle, Redmond, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 321 days.

This patent is subject to a terminal disclaimer.

(21) Appl. No.: 12/387,465

(22) Filed: Apr. 30, 2009

(65) Prior Publication Data

US 2010/0131448 A1 May 27, 2010

Related U.S. Application Data

(63) Continuation-in-part of application No. 12/313,659, filed on Nov. 21, 2008, now Pat. No. 8,046,455, and a continuation-in-part of application No. 12/315,083, filed on Nov. 26, 2008, now Pat. No. 8,005,948, and a continuation-in-part of application No. 12/319,135, filed on Dec. 31, 2008, now Pat. No. 7,937,465, and a (Continued)

(51) Int. Cl.
*G06N 5/02* (2006.01)
*G06F 17/30* (2006.01)

(52) U.S. Cl. ............. 706/52; 706/12; 706/58; 706/11; 709/206; 709/217; 709/224; 709/204; 707/736; 707/687; 707/735

(58) Field of Classification Search ............... 709/203, 709/206, 224, 217, 218; 706/52, 12, 58
See application file for complete search history.

(56) References Cited

U.S. PATENT DOCUMENTS 3,599,149 A 8/1971 Pardoe
(Continued)

FOREIGN PATENT DOCUMENTS

WO WO 99/18842 4/1999

OTHER PUBLICATIONS

Hansen, et al.; "Microblogging—Facilitating Tacit Knowledge?"—A Second Year Term Paper; Information Management Study at Copenhagen Business School; 2008; pp. 1-42; located at http://www.scribd.com/doc/3460679/Microblogging-as-a-Facilitator-for-Tacit-Knowledge.

(Continued)

*Primary Examiner* — Jude Jean Gilles

(57) ABSTRACT

A computationally implemented method includes, but is not limited to: soliciting, based at least in part on a hypothesis that links one or more objective occurrences with one or more subjective user states and in response at least in part to an incidence of at least one subjective user state associated with a user, at least a portion of objective occurrence data including data indicating incidence of at least one objective occurrence; and acquiring the objective occurrence data including the data indicating incidence of at least one objective occurrence. In addition to the foregoing, other method aspects are described in the claims, drawings, and text forming a part of the present disclosure.

46 Claims, 35 Drawing Sheets

Related U.S. Application Data continuation-in-part of application No. 12/319,134, filed on Dec. 31, 2008, now Pat. No. 7,945,632, and a continuation-in-part of application No. 12/378,162, filed on Feb. 9, 2009, now Pat. No. 8,028,063, and a continuation-in-part of application No. 12/378,288, filed on Feb. 11, 2009, now Pat. No. 8,032,628, and a continuation-in-part of application No. 12/380,409, filed on Feb. 25, 2009, now Pat. No. 8,010,662, and a continuation-in-part of application No. 12/380,573, filed on Feb. 26, 2009, and a continuation-in-part of application No. 12/383,581, filed on Mar. 24, 2009, and a continuation-in-part of application No. 12/383,817, filed on Mar. 25, 2009, now Pat. No. 8,010,663, and a continuation-in-part of application No. 12/384,660, filed on Apr. 6, 2009, and a continuation-in-part of application No. 12/384,779, filed on Apr. 7, 2009, and a continuation-in-part of application No. 12/387,487, filed on Apr. 30, 2009.

(56) References Cited

U.S. PATENT DOCUMENTS

| | | | |
|---|---|---|---|
| 7,203,430 | B2 | 4/2007 | Ohta |
| 7,400,928 | B2 | 7/2008 | Hatlestsad |
| 7,627,544 | B2 | 12/2009 | Chkodrov et al. |
| 8,010,604 | B2 | 8/2011 | Lapstun et al. |
| 2003/0166277 | A1 | 9/2003 | Zauderer et al. |
| 2004/0103108 | A1 | 5/2004 | Andreev et al. |
| 2005/0102578 | A1 | 5/2005 | Bliss et al. |
| 2006/0034430 | A1 | 2/2006 | Liakis |
| 2007/0293731 | A1 | 12/2007 | Downs et al. |
| 2008/0034056 | A1 | 2/2008 | Renger et al. |
| 2008/0091515 | A1 | 4/2008 | Thieberger et al. |
| 2008/0215607 | A1 | 9/2008 | Kaushansky et al. |
| 2008/0218472 | A1 | 9/2008 | Breen et al. |
| 2009/0049154 | A1 | 2/2009 | Ge |
| 2009/0077658 | A1 | 3/2009 | King et al. |
| 2009/0132197 | A1 | 5/2009 | Rubin et al. |
| 2009/0240647 | A1 | 9/2009 | Green et al. |
| 2009/0276221 | A1 | 11/2009 | Heiman et al. |
| 2009/0326981 | A1 | 12/2009 | Karkanias et al. |
| 2010/0010866 | A1 | 1/2010 | Bal et al. |
| 2010/0088104 | A1 | 4/2010 | DeRemer et al. |
| 2010/0131504 | A1* | 5/2010 | Firminger et al. ............ 707/736 |

OTHER PUBLICATIONS

Reiss, M.; "Correlations Between Changes in Mental States and Thyroid Activity After Different Forms of Treatment"; The British Journal of Psychology—Journal of Mental Science; bearing dates of Mar. 6, 1954 and 1954; pp. 687-703 [Abstract only provided]; located at http://bjp.rcpsych.org/cgi/content/abstract/100/420/687; The Royal College of Psychiatrists.

Agger, Michael;"Every Day We Write the Book: What would happen if Facebook made its data available for research?"; Slate; bearing date of Nov. 30, 2010; printed on Dec. 10, 2010; pp. 1-3; located at: http://www.slate.com/formatdynamics/CleanPrintProxy.aspx?1292008532368.

"Self-tracking links to get you started"; The Quantified Self: self knowledge through numbers; printed on Dec. 10, 2010; pp. 1-5; located at: http://quantifiedself.com/self-tracking-links-to-get-you-started/.

U.S. Appl. No. 12/462,201, Firminger et al.
U.S. Appl. No. 12/462,128, Firminger et al.
U.S. Appl. No. 12/459,854, Firminger et al.
U.S. Appl. No. 12/459,775, Firminger et al.
U.S. Appl. No. 12/456,433, Firminger et al.
U.S. Appl. No. 12/456,249, Firminger et al.
U.S. Appl. No. 12/455,317, Firminger et al.
U.S. Appl. No. 12/455,309, Firminger et al.
U.S. Appl. No. 12/387,487, Firminger et al.
U.S. Appl. No. 12/384,779, Firminger et al.
U.S. Appl. No. 12/384,660, Firminger et al.
U.S. Appl. No. 12/383,817, Firminger et al.
U.S. Appl. No. 12/383,581, Firminger et al.
U.S. Appl. No. 12/380,573, Firminger et al.
U.S. Appl. No. 12/380,409, Firminger et al.
U.S. Appl. No. 12/378,288, Firminger et al.
U.S. Appl. No. 12/378,162, Firminger et al.

Buchanan, Matt; "Twitter Toilet Tweets Your Poo"; gizmodo.com; bearing a date of May 18, 2009; pp. 1-2; located at http://gizmodo.com/5259381/twitter-toilet-tweets-your-poo; printed on Jul. 1, 2009.

Diaz, Jesus; "One Day, This Will Be Remembered as the First Real Tricorder"; gizmodo.com; bearing a date of Nov. 12, 2009; pp. 1-2; located at http://gizmodo.com/5403126/one-day-this-will-be-remembered-as-the . . . ; printed on Nov. 25, 2009.

Fox, Stuart; "The John, 2.0"; Popular Science; bearing a date of May 18, 2009; pp. 1-2; located at http://www.popsci.com/scitech/article/2009-05/john-20; printed on Jul. 1, 2009.

Frucci, Adam; "SNIF Dog Tags Track What Your Dog Does All Day; Spoiler: Eat, Sleep, Poop"; gizmodo.com; bearing a date of Jun. 10, 2009; pp. 1-2; located at http://i.gizmodo.com/5286076/snif-dog-tags-track-what-your-dog-does-all-day-spoiler-eat-sl . . . ; printed on Jul. 1, 2009.

Gross, Daniel; "A Jewish Mother in Your Cell Phone"; Slate; bearing a date of Nov. 10, 2009; pp. 1-3; located at http://www.slate.com/formatdynamics.CleanPrintProxy.aspx?125919 . . . ; printed on Nov. 25, 2009.

"hacklab.Toilet a twitter-enabled toilet at hacklab.to"; aculei.net; bearing a date of May 18, 2009; pp. 1-8; located at http://aculei.net/-shardy/hacklabtoilet/; printed on Jul. 1, 2009.

U.S. Appl. No. 12/319,135, Firminger et al.
U.S. Appl. No. 12/319,134, Firminger et al.
U.S. Appl. No. 12/315,083, Firminger et al.
U.S. Appl. No. 12/313,659, Firminger et al.

June, Laura; "Apple patent filing shows off activity monitor for skiers, bikers"; engadget.com; bearing a date of Jun. 11, 2009; pp. 1-8; located at http://www.engadget.com/2009/06/11/apple-patent-filing-shows-off-a . . . ; printed on Jul. 1, 2009.

Kraft, Caleb; "Twittering toilet"; Hack A Day; bearing a date of May 5, 2009; pp. 1-11; located at http://hackaday.com/2009/05/05/twittering-toilet/; printed Jul. 1, 2009.

"Mobile pollution sensors deployed"; BBC News; bearing a date of Jun. 30, 2009; pp. 1-2; located at http://news.bbc.co.uk/2/hi/science/nature/8126498.stm; printed on Jul. 1, 2009; © BBC MMIX.

Morales, C. Romero et al.; "Using sequential pattern mining for links recommendation in adaptive hypermedia educational systems"; Current Developments in Technology-Assisted Education; bearing a date of 2006; pp. 1016-1020; © FORMATEX 2006.

Nesbit, J.C. et al.; "Sequential pattern analysis software for educational event data"; pp. 1-5.

Oliver, Sam; "Apple developing activity monitor for skiers, snowboarders, bikers"; AppleInsider; bearing a date of Jun. 11, 2009; pp. 1-6; located at http://www.appleinsider.com/articles/09/06/11/apple_developing_act . . . ; printed on Jul. 1, 2009; AppleInsider © 1997-2008.

Rettner, Rachael; "Cell Phones Allow Everyone to Be a Scientist"; LiveScience; bearing a date of Jun. 4, 2009; pp. 1-3; located at http://www.livescience.com/technology/090604-mobile-sensor.html printed on Jul. 1, 2009; © Imaginova Corp.

SPSS; "Find patterns in data that identify combinations of events that occur together"; SPSS Association Rule Components; bearing a date of 2002; pp. 1-5; © 2002 SPSS Inc.

SPSS; "Find sequential patterns in data to predict events more accurately"; SPSS Sequence Association™ Component; bearing a date of 2002; pp. 1-5; © 2002 SPSS Inc.

Karimi, A. et al.; "A Predictive Location Model for Location-Based Services"; *GIS'03*; Nov. 7-8, 2003; pp. 126-133; ACM.

Ulicny, B. et al.; "New Metrics for Blog Mining"; Data Mining, Intrusion Detection, Information Assurance, and Data Networks Security 2007; Proceedings of the SPIE; 2007; 12 pages; vol. 6570.

* cited by examiner

101 Objective Occurrence Data Solicitation Module

202 Requesting Module

204 User Interface Requesting Module

205 Request Indication Module

206 Network Interface Requesting Module

207 Request Transmission Module

208 Request Access Module

209 Configuration Module

210 Directing/instructing Module

212 Motivation Provision Module

214 Selection Request Module

216 Confirmation Request Module

218 Time/Temporal Element Request Module

220 Hypothesis Referencing Module

FIG. 2a

102 Subjective User State Data Acquisition Module

224 Subjective User State Data Reception Module

226 User Interface Reception Module

227 Network Interface Reception Module

228 Time Data Acquisition Module

230 Time Stamp Acquisition Module

231 Time Interval Acquisition Module

FIG. 2b

104 Objective Occurrence Data Acquisition Module

234 Objective Occurrence Data Reception Module

235 User Interface Data Reception Module

236 Network Interface Data Reception Module

FIG. 2c

101' Objective Occurrence Data Solicitation Module

- 202' Requesting Module
  - 204' User Interface Requesting Module
    - 205' Request Indication Module
  - 206' Network Interface Requesting Module
  - 207' Request Transmission Module
  - 208' Request Access Module
  - 209' Configuration Module
  - 210' Directing/instructing Module
  - 212' Motivation Provision Module
  - 214' Selection Request Module
  - 216' Confirmation Request Module
  - 218' Time/Temporal Element Request Module

- 270 Request to Solicit Reception Module

FIG. 2h

HYPOTHESIS BASED SOLICITATION OF DATA INDICATING AT LEAST ONE OBJECTIVE OCCURRENCE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of United States Patent Application No. 12/387,487, entitled HYPOTHESIS BASED SOLICITATION OF DATA INDICATING AT LEAST ONE OBJECTIVE OCCURRENCE, naming Shawn P. Firminger, Jason Garms, Edward K.Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 30 Apr. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/313,659, entitled CORRELATING SUBJECTIVE USER STATES WITH OBJECTIVE OCCURRENCES ASSOCIATED WITH A USER, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 21 Nov. 2008 now U.S. Pat. No. 8,046,455, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/315,083, entitled CORRELATING SUBJECTIVE USER STATES WITH OBJECTIVE OCCURRENCES ASSOCIATED WITH A USER, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 26 Nov. 2008 now U.S. Pat. No. 8,005,948, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/319,135, entitled CORRELATING DATA INDICATING AT LEAST ONE SUBJECTIVE USER STATE WITH DATA INDICATING AT LEAST ONE OBJECTIVE OCCURRENCE ASSOCIATED WITH A USER, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 31 Dec. 2008 now U.S. Pat. No. 7,937,465, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/319,134, entitled CORRELATING DATA INDICATING AT LEAST ONE SUBJECTIVE USER STATE WITH DATA INDICATING AT LEAST ONE OBJECTIVE OCCURRENCE ASSOCIATED WITH A USER, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 31 Dec. 2008 now U.S. Pat. No.7,945,632, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/378,162, entitled SOLICITING DATA INDICATING AT LEAST ONE OBJECTIVE OCCURRENCE IN RESPONSE TO ACQUISITION OF DATA INDICATING AT LEAST ONE SUBJECTIVE USER STATE, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 9 Feb. 2009 now U.S. Pat. No. 8,028,063, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/378,288, entitled SOLICITING DATA INDICATING AT LEAST ONE OBJECTIVE OCCURRENCE IN RESPONSE TO ACQUISITION OF DATA INDICATING AT LEAST ONE SUBJECTIVE USER STATE, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 11 Feb. 2009 now U.S. Pat. No. 8,032,628, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/380,409, entitled SOLICITING DATA INDICATING AT LEAST ONE SUBJECTIVE USER STATE IN RESPONSE TO ACQUISITION OF DATA INDICATING AT LEAST ONE OBJECTIVE OCCURRENCE, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 25 Feb. 2009 now U.S. Pat. No. 8,010,662, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/380,573, entitled SOLICITING DATA INDICATING AT LEAST ONE SUBJEC- TIVE USER STATE IN RESPONSE TO ACQUISITION OF DATA INDICATING AT LEAST ONE OBJECTIVE OCCURRENCE, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 26 Feb. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/383,581, entitled CORRELATING DATA INDICATING SUBJECTIVE USER STATES ASSOCIATED WITH MULTIPLE USERS WITH DATA INDICATING OBJECTIVE OCCURRENCES, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 24 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/383,817, entitled CORRELATING DATA INDICATING SUBJECTIVE USER STATES ASSOCIATED WITH MULTIPLE USERS WITH DATA INDICATING OBJECTIVE OCCURRENCES, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 25 Mar. 2009 now U.S. Pat. No. 8,010,663, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/384,660, entitled HYPOTHESIS BASED SOLICITATION OF DATA INDICATING AT LEAST ONE SUBJECTIVE USER STATE, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 6 Apr. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/384,779, entitled HYPOTHESIS BASED SOLICITATION OF DATA INDICATING AT LEAST ONE SUBJECTIVE USER STATE, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 7 Apr. 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

A computationally implemented method includes, but is not limited to soliciting, based at least in part on a hypothesis that links one or more objective occurrences with one or more subjective user states and in response at least in part to an incidence of at least one subjective user state associated with a user, at least a portion of objective occurrence data including data indicating incidence of at least one objective occurrence; and acquiring the objective occurrence data including the data indicating incidence of at least one objective occurrence. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

A computationally implemented system includes, but is not limited to: means for soliciting, based at least in part on a hypothesis that links one or more objective occurrences with one or more subjective user states and in response at least in part to an incidence of at least one subjective user state associated with a user, at least a portion of objective occurrence data including data indicating incidence of at least one objective occurrence; and means for acquiring the objective occurrence data including the data indicating incidence of at least one objective occurrence. In addition to the foregoing, other system aspects are described in the claims, drawings, and text forming a part of the present disclosure.

A computationally implemented system includes, but is not limited to: circuitry for soliciting, based at least in part on a hypothesis that links one or more objective occurrences with one or more subjective user states and in response at least in part to an incidence of at least one subjective user state associated with a user, at least a portion of objective occurrence data including data indicating incidence of at least one objective occurrence; and circuitry for acquiring the objective occurrence data including the data indicating incidence of at least one objective occurrence. In addition to the foregoing, other system aspects are described in the claims, drawings, and text forming a part of the present disclosure.

A computer program product including a signal-bearing medium bearing one or more instructions for soliciting, based at least in part on a hypothesis that links one or more objective occurrences with one or more subjective user states and in response at least in part to an incidence of at least one subjective user state associated with a user, at least a portion of objective occurrence data including data indicating incidence of at least one objective occurrence; and one or more instructions for acquiring the objective occurrence data including the data indicating incidence of at least one objective occurrence. In addition to the foregoing, other computer program product aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2a shows another perspective of the objective occurrence data solicitation module 101 of the computing device 10 of FIG. 1b.

FIG. 2b shows another perspective of the subjective user state data acquisition module 102 of the computing device 10 of FIG. 1b.

FIG. 2c shows another perspective of the objective occurrence data acquisition module 104 of the computing device 10 of FIG. 2b.

FIG. 2g shows another perspective of the mobile device 30 of FIG. 1a.

FIG. 2h shows another perspective of the objective occurrence data solicitation module 101' of the mobile device 30 of FIG. 2g.

DETAILED DESCRIPTION

Figure 1A:
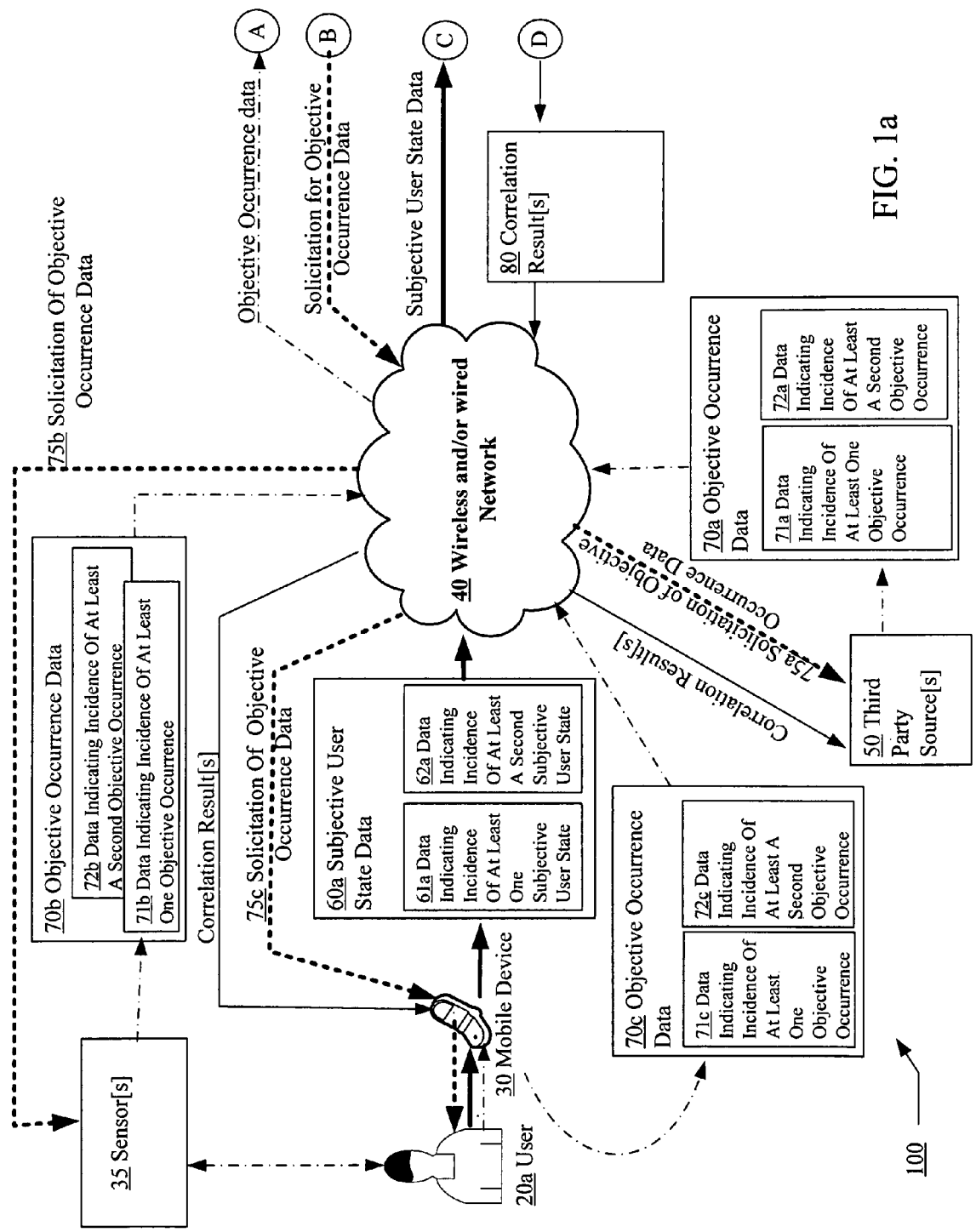
FIGS. 1a and 1b show a high-level block diagram of a mobile device 30 and a computing device 10 operating in a network environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

A recent trend that is becoming increasingly popular in the computing/communication field is to electronically record one's feelings, thoughts, and other aspects of the person's everyday life onto an open diary. One place where such open diaries are maintained are at social networking sites commonly known as "blogs" where one or more users may report or post their thoughts and opinions on various topics, latest news, current events, and various other aspects of the users' everyday life. The process of reporting or posting blog entries is commonly referred to as blogging. Other social networking sites may allow users to update their personal information via, for example, social network status reports in which a user may report or post for others to view the latest status or other aspects of the user.

A more recent development in social networking is the introduction and explosive growth of microblogs in which individuals or users (referred to as "microbloggers") maintain open diaries at microblog websites (e.g., otherwise known as "twitters") by continuously or semi-continuously posting microblog entries. A microblog entry (e.g., "tweet") is typically a short text message that is usually not more than 140 characters long. The microblog entries posted by a microblogger may report on any aspect of the microblogger's daily life.

The various things that are typically posted through microblog entries may be categorized into one of at least two possible categories. The first category of things that may be reported through microblog entries are "objective occurrences" that may or may not be associated with the microblogger. Objective occurrences that are associated with a microblogger may be any characteristic, event, happening, or any other aspects associated with or are of interest to the microblogger that can be objectively reported by the microblogger, a third party, or by a device. These things would include, for example, food, medicine, or nutraceutical intake of the microblogger, certain physical characteristics of the microblogger such as blood sugar level or blood pressure that can be objectively measured, daily activities of the microblogger observable by others or by a device, performance of the stock market (which the microblogger may have an interest in), and so forth. In some cases, objective occurrences may not be at least directly associated with a microblogger. Examples of such objective occurrences include, for example, external events that may not be directly related to the microblogger such as the local weather, activities of others (e.g., spouse or boss) that may directly or indirectly affect the microblogger, and so forth.

A second category of things that may be reported or posted through microblog entries include "subjective user states" of the microblogger. Subjective user states of a microblogger include any subjective state or status associated with the microblogger that can only be typically reported by the microblogger (e.g., generally cannot be reported by a third party or by a device). Such states including, for example, the subjective mental state of the microblogger (e.g., "I am feeling happy"), the subjective physical state of the microblogger (e.g., "my ankle is sore" or "my ankle does not hurt anymore" or "my vision is blurry"), and the subjective overall state of the microblogger (e.g., "I'm good" or "I'm well"). Note that the term "subjective overall state" as will be used herein refers to those subjective states that may not fit neatly into the other two categories of subjective user states described above (e.g., subjective mental states and subjective physical states).

Although microblogs are being used to provide a wealth of personal information, they have thus far been primarily limited to their use as a means for providing commentaries and for maintaining open diaries.

In accordance with various embodiments, methods, systems, and computer program products are provided to, among other things, solicit and acquire at least a portion of objective occurrence data including data indicating incidence of at least one objective occurrence, the solicitation being directly or indirectly prompted based, at least in part on a hypothesis that links one or more subjective user states with one or more objective occurrences and in response to an incidence of at least one subjective user state associated with a user.

In various embodiments, a "hypothesis" may define one or more relationships or links between one or more subjective user states and one or more objective occurrences. In some embodiments, a hypothesis may be defined by a sequential pattern that indicates or suggests a temporal or specific time sequencing relationship between one or more subjective user states and one or more objective occurrences. In some cases, the one or more subjective user states associated with the hypothesis may be based on past incidences of one or more subjective user states that are associated with a user, that are associated with multiple users, that are associated with a sub-group of the general population, or that are associated with the general population. Similarly, the one or more objective occurrences associated with the hypothesis may be based on past incidences of objective occurrences.

In some cases, a hypothesis may be formulated when it is determined that a particular pattern of events (e.g., incidences of one or more subjective user states and one or more objective occurrences) occurs repeatedly with respect to a particular user, a group of users, a subset of the general population, or the general population. For example, a hypothesis may be formulated that suggests or predicts that a person will likely have an upset stomach after eating a hot fudge sundae when it is determined that multiple users had reported having an upset stomach after eating a hot fudge sundae. In other cases, a hypothesis may be formulated based, at least in part, on a single pattern of events and historical data related to such events. For instance, a hypothesis may be formulated when a person reports that he had a stomach ache after eating a hot fudge sundae, and historical data suggests that a segment of the population may not be able to digest certain nutrients included in a hot fudge sundae (e.g., the hypothesis would suggest or indicate that the person may get stomach aches whenever the person eats a hot fudge sundae).

The subjective user state data to be acquired by the methods, systems, and the computer program products may include data indicating the incidence of at least one subjective user state associated with a user. Such subjective user state data together with objective occurrence data including data indicating incidence of at least one objective occurrence may then be correlated. The results of the correlation may be presented in a variety of different forms and may, in some cases, confirm the veracity of the hypothesis. The results of the correlation, in various embodiments, may be presented to the user, to other users, or to one or more third parties as will be further described herein.

In some embodiments, the correlation of the acquired subjective user state data with the objective occurrence data may facilitate in determining a causal relationship between at least one objective occurrence (e.g., cause) and at least one subjective user state (e.g., result). For example, determining whenever a user eats a banana the user always or sometimes feels good. Note that an objective occurrence does not need to occur prior to a corresponding subjective user state but instead, may occur subsequent or at least partially concurrently with the incidence of the subjective user state. For example, a person may become "gloomy" (e.g., subjective user state) whenever it is about to rain (e.g., objective occurrence) or a person may become gloomy while (e.g., concurrently) it is raining. Further, in some cases, subjective user states may actually be the "cause" while an objective occurrence may be the "result." For instance, when a user is angry (e.g., subjective user state), the user's angry state may cause his blood pressure (e.g., objective occurrence) to rise. Thus, a more relevant point to determine between subjective user states and objective occurrences is whether there are any links or relationships between the two types of events (e.g., subjective user states and objective occurrences).

An "objective occurrence data," as will be described herein, may include data that indicate incidence of at least one objective occurrence. In some embodiments, an objective occurrence may be any physical characteristic, event, happenings, or any other aspect that may be associated with, is of interest to, or may somehow impact a user that can be objectively reported by at least a third party or a sensor device. Note, however, that an objective occurrence does not have to be actually reported by a sensor device or by a third party, but instead, may be reported by the user himself or herself (e.g., via microblog entries). Examples of objectively reported occurrences that could be indicated by the objective occurrence data include, for example, a user's food, medicine, or nutraceutical intake, the user's location at any given point in time, a user's exercise routine, a user's physiological characteristics such as blood pressure, social or professional activities, the weather at a user's location, activities associated with third parties, occurrence of external events such as the performance of the stock market, and so forth.

As briefly described earlier, the objective occurrence data to be acquired may include data that indicate the incidence or occurrence of at least one objective occurrence. In situations where the objective occurrence data to be acquired indicates multiple objective occurrences, each of the objective occurrences indicated by the acquired objective occurrence data may be solicited, while in other embodiments, only one or a subset of the objective occurrences indicated by the acquired objective occurrence data may be solicited.

A "subjective user state," in contrast, is in reference to any subjective user state or status associated with a user (e.g., a blogger or microblogger) at any moment or interval in time that only the user can typically indicate or describe. Such states include, for example, the subjective mental state of the user (e.g., user is feeling sad), the subjective physical state (e.g., physical characteristic) of the user that only the user can typically indicate (e.g., a backache or an easing of a backache as opposed to blood pressure which can be reported by a blood pressure device and/or a third party), and the subjective overall state of the user (e.g., user is "good").

Examples of subjective mental states include, for example, happiness, sadness, depression, anger, frustration, elation, fear, alertness, sleepiness, and so forth. Examples of subjective physical states include, for example, the presence, easing, or absence of pain, blurry vision, hearing loss, upset stomach, physical exhaustion, and so forth. Subjective overall states may include any subjective user states that cannot be easily categorized as a subjective mental state or as a subjective physical state. Examples of subjective overall states include, for example, the user "being good," "bad," "exhausted," "lack of rest," "wellness," and so forth.

The term "correlating" as will be used herein may be in reference to a determination of one or more relationships between at least two variables. Alternatively, the term "correlating" may merely be in reference to the linking or associating of the at least two variables. In the following exemplary embodiments, the first variable is subjective user state data that indicates at least one subjective user state and the second variable is objective occurrence data that indicates at least one objective occurrence. In embodiments where the subjective user state data indicates multiple subjective user states, each of the subjective user states indicated by the subjective user state data may represent different incidences of the same or similar type of subjective user state (e.g., happiness). Alternatively, the subjective user state data may indicate multiple subjective user states that represent different incidences of different types of subjective user states (e.g., happiness and sadness).

Similarly, in some embodiments where the objective occurrence data may indicate multiple objective occurrences, each of the objective occurrences indicated by the objective occurrence data may represent different incidences of the same or similar type of objective occurrence (e.g., exercising). In alternative embodiments, however, each of the objective occurrences indicated by the objective occurrence data may represent different incidences of different types of objective occurrence (e.g., user exercising and user resting).

Various techniques may be employed for correlating subjective user state data with objective occurrence data in various alternative embodiments. For example, in some embodiments, the correlation of the objective occurrence data with the subjective user state data may be accomplished by determining a sequential pattern associated with at least one subjective user state indicated by the subjective user state data and at least one objective occurrence indicated by the objective occurrence data. In other embodiments, the correlation of the objective occurrence data with the subjective user state data may involve determining multiple sequential patterns associated with multiple subjective user states and multiple objective occurrences.

A sequential pattern, as will be described herein, may define time and/or temporal relationships between two or more events (e.g., one or more subjective user states and one or more objective occurrences). In order to determine a sequential pattern, at least a portion of objective occurrence data including data indicating incidence of at least one objective occurrence may be solicited, the solicitation being prompted based, at least in part, on a hypothesis linking one or more subjective user states with one or more objective occurrences and in response, at least in part, to an incidence of at least one subjective user state associated with a user.

For example, suppose a hypothesis suggests that a user or a group of users tend to be depressed whenever the weather is bad (e.g., cloudy or overcast weather). In some implementations, such a hypothesis may have been derived based on, for example, reported past events (e.g., reported past subjective user states of a user or a group of users and reported past objective occurrences). Based at least in part on the hypothesis and upon a user reporting being emotionally depressed, objective occurrence data including data indicating incidence of at least one objective occurrence may be solicited from, for example, the user or from one or more third party sources such as a weather reporting service. If the solicitation for the objective occurrence data is successful then the objective occurrence data may be acquired from the source (e.g., a user, one or more third party sources, or one or more sensors). If the acquired objective occurrence data indicates that the weather was indeed bad when the user felt depressed, then this may confirm the veracity of the hypothesis. On the other hand, if the data that is acquired after the solicitation indicates that the weather was good when the user was depressed, this may indicate that there is a weaker correlation or link between depression and bad weather.

As briefly described above, a hypothesis may be represented by a sequential pattern that may merely indicate or represent the temporal relationship or relationships between at least one subjective user state and at least one objective occurrence (e.g., whether the incidence or occurrence of at least one subjective user state occurred before, after, or at least partially concurrently with the incidence of the at least one objective occurrence). In alternative implementations, and as will be further described herein, a sequential pattern may indicate a more specific time relationship between the incidences of one or more subjective user states and the incidences of one or more objective occurrences. For example, a sequential pattern may represent the specific pattern of events (e.g., one or more objective occurrences and one or more subjective user states) that occurs along a timeline.

The following illustrative example is provided to describe how a sequential pattern associated with at least one subjective user state and at least one objective occurrence may be determined based, at least in part, on the temporal relationship between the incidence of at least one subjective user state and the incidence of at least one objective occurrence in accordance with some embodiments. For these embodiments, the determination of a sequential pattern may initially involve determining whether the incidence of the at least one subjective user state occurred within some predefined time increment from the incidence of the one objective occurrence. That is, it may be possible to infer that those subjective user states that did not occur within a certain time period from the incidence of an objective occurrence are not related or are unlikely related to the incidence of that objective occurrence.

For example, suppose a user during the course of a day eats a banana and also has a stomach ache sometime during the course of the day. If the consumption of the banana occurred in the early morning hours but the stomach ache did not occur until late that night, then the stomach ache may be unrelated to the consumption of the banana and may be disregarded. On the other hand, if the stomach ache had occurred within some predefined time increment, such as within 2 hours of consumption of the banana, then it may be concluded that there is a link between the stomach ache and the consumption of the banana. If so, a temporal relationship between the consumption of the banana and the occurrence of the stomach ache may be established. Such a temporal relationship may be represented by a sequential pattern. Such a sequential pattern may simply indicate that the stomach ache (e.g., a subjective user state) occurred after (rather than before or concurrently) the consumption of banana (e.g., an objective occurrence).

Other factors may also be referenced and examined in order to determine a sequential pattern and whether there is a relationship (e.g., causal relationship) between an incidence of an objective occurrence and an incidence of a subjective user state. These factors may include, for example, historical data (e.g., historical medical data such as genetic data or past history of the user or historical data related to the general population regarding, for example, stomach aches and bananas) as briefly described above.

In some implementations, a sequential pattern may be determined for multiple subjective user states and multiple objective occurrences. Such a sequential pattern may particularly map the exact temporal or time sequencing of the various events (e.g., subjective user states and objective occurrences). The determined sequential pattern may then be used to provide useful information to the user and/or third parties.

The following is another illustrative example of how subjective user state data may be correlated with objective occurrence data by determining multiple sequential patterns and comparing the sequential patterns with each other. Suppose, for example, a user such as a microblogger reports that the user ate a banana on a Monday. The consumption of the banana, in this example, is a reported incidence of a first objective occurrence associated with the user. The user then reports that 15 minutes after eating the banana, the user felt very happy. The reporting of the emotional state (e.g., felt very happy) is, in this example, a reported incidence of a first subjective user state. Thus, the reported incidence of the first objective occurrence (e.g., eating the banana) and the reported incidence of the first subjective user state (user felt very happy) on Monday may be represented by a first sequential pattern.

On Tuesday, the user reports that the user ate another banana (e.g., a second objective occurrence associated with the user). The user then reports that 20 minutes after eating the second banana, the user felt somewhat happy (e.g., a second subjective user state). Thus, the reported incidence of the second objective occurrence (e.g., eating the second banana) and the reported incidence of the second subjective user state (user felt somewhat happy) on Tuesday may be represented by a second sequential pattern. Under this scenario, the first sequential pattern may represent a hypothesis that links feeling happy or very happy (e.g., a subjective user state) with eating a banana (e.g., an objective occurrence). Alternatively, the first sequential pattern may merely represent historical data (e.g., historical sequential pattern). Note that in this example, the occurrences of the first subjective user state and the second subjective user state may be indicated by subjective user state data while the occurrences of the first objective occurrence and the second objective occurrence may be indicated by objective occurrence data.

In a slight variation of the above example, suppose the user had forgotten to report the consumption of the second banana on Tuesday but does report feeling somewhat happy on Tuesday. This may result in the user being asked, based at least in part on the reporting of the user feeling somewhat happy on Tuesday, and based at least in part on the hypothesis, as to whether the user ate anything around the time that the user felt happy on Tuesday. Upon the user indicating that the user ate a banana on Tuesday, a second sequential pattern may be determined based on the reported events of Tuesday.

In any event, by comparing the first sequential pattern with the second sequential pattern, the subjective user state data may be correlated with the objective occurrence data. Such a comparison may confirm the veracity of the hypothesis. In some implementations, the comparison of the first sequential pattern with the second sequential pattern may involve trying to match the first sequential pattern with the second sequential pattern by examining certain attributes and/or metrics. For example, comparing the first subjective user state (e.g., user felt very happy) of the first sequential pattern with the second subjective user state (e.g., user felt somewhat happy) of the second sequential pattern to see if they at least substantially match or are contrasting (e.g., being very happy in contrast to being slightly happy or being happy in contrast to being sad). Similarly, comparing the first objective occurrence (e.g., eating a banana) of the first sequential pattern may be compared to the second objective occurrence (e.g., eating of another banana) of the second sequential pattern to determine whether they at least substantially match or are contrasting.

A comparison may also be made to determine if the extent of time difference (e.g., 15 minutes) between the first subjective user state (e.g., user being very happy) and the first objective occurrence (e.g., user eating a banana) matches or are at least similar to the extent of time difference (e.g., 20 minutes) between the second subjective user state (e.g., user being somewhat happy) and the second objective occurrence (e.g., user eating another banana). These comparisons may be made in order to determine whether the first sequential pattern matches the second sequential pattern. A match or substantial match would suggest, for example, that a subjective user state (e.g., happiness) is linked to a particular objective occurrence (e.g., consumption of banana). In other words, confirming the hypothesis that happiness may be linked to the consumption of bananas.

As briefly described above, the comparison of the first sequential pattern with the second sequential pattern may include a determination as to whether, for example, the respective subjective user states and the respective objective occurrences of the sequential patterns are contrasting subjective user states and/or contrasting objective occurrences. For example, suppose in the above example the user had reported that the user had eaten a whole banana on Monday and felt very energetic (e.g., first subjective user state) after eating the whole banana (e.g., first objective occurrence). Suppose that the user also reported that on Tuesday he ate a half a banana instead of a whole banana and only felt slightly energetic (e.g., second subjective user state) after eating the half banana (e.g., second objective occurrence). In this scenario, the first sequential pattern (e.g., feeling very energetic after eating a whole banana) may be compared to the second sequential pattern (e.g., feeling slightly energetic after eating only a half of a banana) to at least determine whether the first subjective user state (e.g., being very energetic) and the second subjective user state (e.g., being slightly energetic) are contrasting subjective user states. Another determination may also be made during the comparison to determine whether the first objective occurrence (eating a whole banana) is in contrast with the second objective occurrence (e.g., eating a half of a banana).

In doing so, an inference may be made that eating a whole banana instead of eating only a half of a banana makes the user happier or eating more banana makes the user happier. Thus, the word "contrasting" as used here with respect to subjective user states refers to subjective user states that are the same type of subjective user states (e.g., the subjective user states being variations of a particular type of subjective user states such as variations of subjective mental states). Thus, for example, the first subjective user state and the second subjective user state in the previous illustrative example are merely variations of subjective mental states (e.g., happiness). Similarly, the use of the word "contrasting" as used here with respect to objective occurrences refers to objective states that are the same type of objective occurrences (e.g., consumption of food such as banana).

As those skilled in the art will recognize, a stronger correlation between the subjective user state data and the objective occurrence data could be obtained if a greater number of sequential patterns (e.g., if there was a third sequential pattern, a fourth sequential pattern, and so forth, that indicated that the user became happy or happier whenever the user ate bananas) are used as a basis for the correlation. Note that for ease of explanation and illustration, each of the exemplary sequential patterns to be described herein will be depicted as a sequential pattern of an incidence of a single subjective user state and an incidence of a single objective occurrence. However, those skilled in the art will recognize that a sequential pattern, as will be described herein, may also be associated with incidences or occurrences of multiple objective occurrences and/or multiple subjective user states. For example, suppose the user had reported that after eating a banana, he had gulped down a can of soda. The user then reported that he became happy but had an upset stomach. In this example, the sequential pattern associated with this scenario will be associated with two objective occurrences (e.g., eating a banana and drinking a can of soda) and two subjective user states (e.g., user having an upset stomach and feeling happy).

In some embodiments, and as briefly described earlier, the sequential patterns derived from subjective user state data and objective occurrence data may be based on temporal relationships between objective occurrences and subjective user states. For example, whether a subjective user state occurred before, after, or at least partially concurrently with an objective occurrence. For instance, a plurality of sequential patterns derived from subjective user state data and objective occurrence data may indicate that a user always has a stomach ache (e.g., subjective user state) after eating a banana (e.g., first objective occurrence).

Figure 1B:
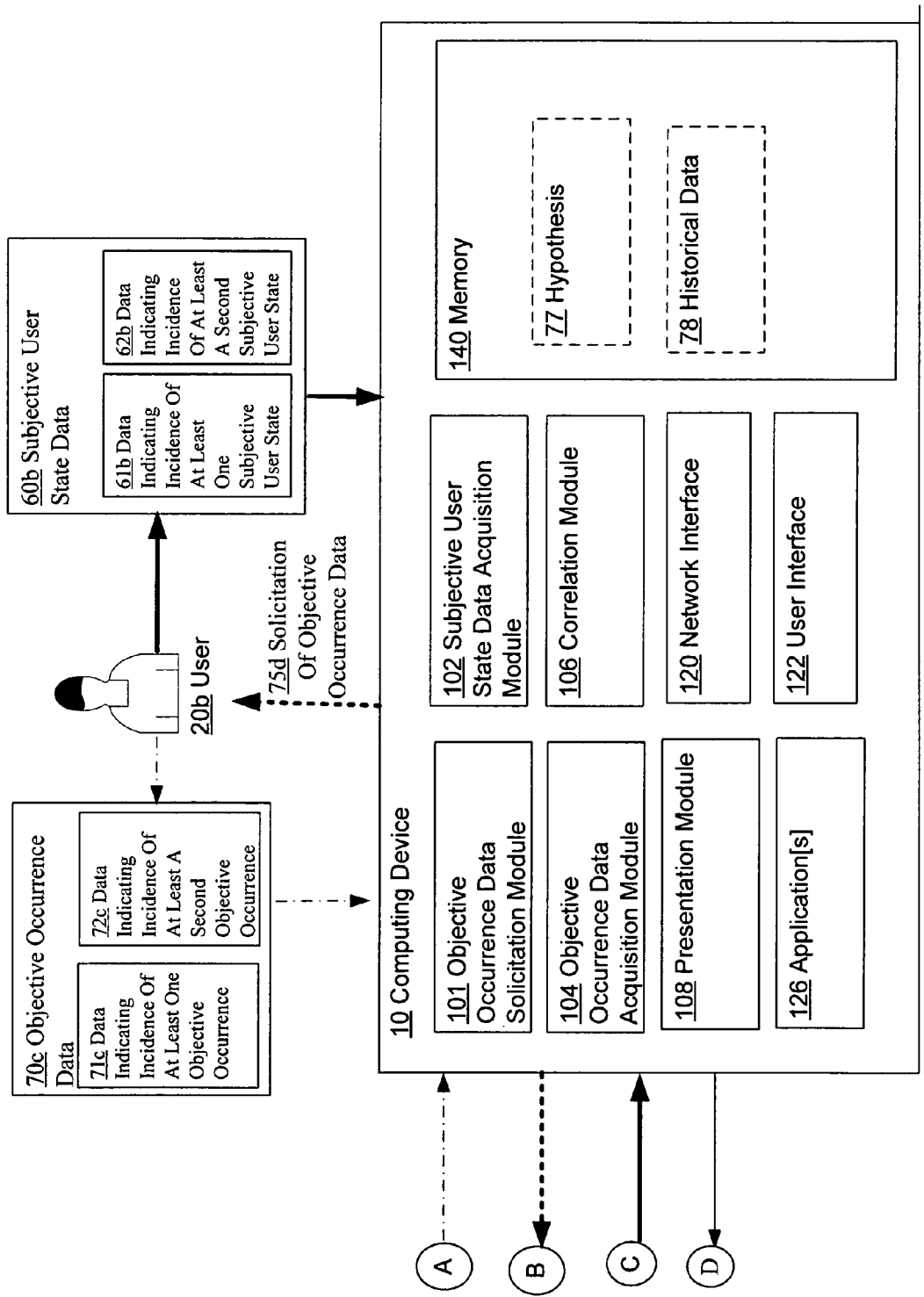

FIGS. 1a and 1b illustrate an example environment in accordance with various embodiments. In the illustrated environment, an exemplary system 100 may include at least a computing device 10 (see FIG. 1b). The computing device 10, which may be a server (e.g., network server) or a standalone device, may be employed in order to, among other things, solicit and acquire at least a portion of objective occurrence data 70* including data indicating occurrence of at least one objective occurrence 71*, to acquire subjective user state data 60* including data indicating incidence of at least one subjective user state 61* associated with a user 20*, and to correlate the subjective user state data 60* with the objective occurrence data 70*. In embodiments in which the computing device 10 is a server, the exemplary system 100 may also include a mobile device 30 to at least solicit and acquire at least a portion of the objective occurrence data 70* including the data indicating incidence of at least one objective occurrence 71* in response to, for example, a request made by the computing device 10 for objective occurrence data 70*. Note that in the following, "*" indicates a wildcard. Thus, user 20* may indicate a user 20a or a user 20b of FIGS. 1a and 1b.

The term "standalone device" as referred to herein may be in reference to a device or system that is configured to acquire the subjective user state data 60* and the objective occurrence data 70* and performs a correlation operation to at least substantially correlate the subjective user state data 60* with the objective occurrence data 70*. In contrast, a mobile device 30, although may acquire both the subjective user state data 60* and the objective occurrence data 70* like a standalone device, the mobile device 30 does not perform a correlation operation in order to substantially correlate the subjective user state data 60* with the objective occurrence data 70*.

As previously indicated, in some embodiments, the computing device 10 may be a network server in which case the computing device 10 may communicate with a user 20a via a mobile device 30 and through a wireless and/or wired network 40. A network server, as will be described herein, may be in reference to a server located at a single network site or located across multiple network sites or a conglomeration of servers located at multiple network sites. The mobile device 30 may be a variety of computing/communication devices including, for example, a cellular phone, a personal digital assistant (PDA), a laptop, a desktop, or other types of computing/communication device that can communicate with the computing device 10. In some embodiments, the mobile device 30 may be a handheld device such as a cellular telephone, a smartphone, a Mobile Internet Device (MID), an Ultra Mobile Personal Computer (UMPC), a convergent device such as a personal digital assistant (PDA), and so forth.

In alternative embodiments, the computing device 10 may be a standalone computing device 10 (or simply "standalone device") that communicates directly with a user 20b. For these embodiments, the computing device 10 may be any type of handheld device. In various embodiments, the computing device 10 (as well as the mobile device 30) may be a peer-to-peer network component device. In some embodiments, the computing device 10 and/or the mobile device 30 may operate via a Web 2.0 construct (e.g., Web 2.0 application 268).

In embodiments where the computing device 10 is a server, the computing device 10 may acquire the subjective user state data 60* indirectly from a user 20a via a network interface 120 and via mobile device 30. In alternative embodiments in which the computing device 10 is a standalone device such as a handheld device (e.g., cellular telephone, a smartphone, a MID, a UMPC, a PDA, and so forth), the subjective user state data 60* may be directly obtained from a user 20b via a user interface 122. As will be further described, the computing device 10 may solicit and acquire at least a portion of the objective occurrence data 70* (e.g., objective occurrence data 70a, objective occurrence data 70b, and/or objective occurrence data 70c) from one or more alternative sources. For example, in some situations, the computing device 10 may obtain objective occurrence data 70a from one or more third party sources 50 (e.g., content providers, other users, health care entities, businesses such as retail businesses, health fitness centers, social organizations, and so forth). In some situations, the computing device 10 may obtain objective occurrence data 70b from one or more sensors 35 (e.g., blood pressure sensors, glucometers, global positioning system (GPS), heart rate monitor, and so forth). In other situations, the computing device 10 (in the case where the computing device 10 is a server) may obtain objective occurrence data 70c from a user 20a via the mobile device 30 and through the wireless and/or wired network 40 or from a user 20b via user interface 122 (when the computing device 10 is a standalone device).

Note that in embodiments where the computing device 10 is a server, the computing device 10 may acquire the objective occurrence data 70a (e.g., from the one or more third party sources 50) and the objective occurrence data 70b (e.g. from the one or more sensors 35) via the mobile device 30. That is, in certain scenarios, only the user 20a (and the mobile device 30) may have access to such data in which case the computing device 10 may have to rely on the user 20a via the mobile device 30 in order to acquire the objective occurrence data 70a and 70b.

In order to acquire the objective occurrence data 70*, the computing device 10 may solicit at least a portion of the objective occurrence data 70* from one or more of the sources (e.g., user 20*, one or more third party sources 50, and/or one or more remote devices including one or more sensors 35). For example, in order to solicit at least a portion of the objective occurrence data 70a including soliciting data indicating incidence of at least one objective occurrence 71a, the computing device 10 may transmit a solicitation for objective occurrence data 75a to the one or more third party sources 50 via wireless and/or wired networks 40. In order to solicit at least a portion of the objective occurrence data 70b including soliciting data indicating incidence of at least one objective occurrence 71b, the computing device 10 may transmit a solicitation for objective occurrence data 75b to the one or more sensors 35. Finally, in order to solicit at least a portion of the objective occurrence data 70c including soliciting data indicating incidence of at least one objective occurrence 71c, the computing device 10 may transmit or indicate a solicitation for objective occurrence data 75c to a user 20*.

Note that an objective occurrence data 70* (e.g., objective occurrence data 70a, 70b, or 70c) may include data that indicates multiple incidences of objective occurrences. For ease of understanding and simplicity, however, each of the objective occurrence data 70* illustrated in FIG. 1a have been depicted as including only data indicating incidence of at least one objective occurrence 71* and data indicating incidence of at least a second objective occurrence 72*. However, in alternative implementations, each of the objective occurrence data 70* may also include data indicating incidence of at least a third objective occurrence, data indicating incidence of at least a fourth objective occurrence, and so forth. In various implementations, only a portion of the objective occurrence data 70* may need to be solicited. For example, in some implementations, only the data indicating incidence of at least one objective occurrence 71* may be solicited while the data indicating incidence of at least a second objective occurrence 72* may have be provided without any solicitation of such data.

In various embodiments, and regardless of whether the computing device 10 is a server or a standalone device, the computing device 10 may have access to at least one hypothesis 77. For example, in some situations, a hypothesis 77 may have been generated based on reported past events including past incidences of one or more subjective user states (which may be associated with a user 20*, a group of users 20*, a portion of the general population, or the general population) and past incidences of one or more objective occurrences. Such a hypothesis 77, in some instances, may be stored in a memory 140 to be easily accessible.

For ease of illustration and explanation, the following systems and operations to be described herein will be generally described in the context of the computing device 10 being a network server. However, those skilled in the art will recognize that these systems and operations may also be implemented when the computing device 10 is a standalone device such as a handheld device that may communicate directly with a user 20b.

The computing device 10, in various implementations, may be configured to solicit at least a portion of objective occurrence data 70* including soliciting data indicating incidence of at least one objective occurrence 71*. The solicitation of the data indicating incidence of at least one objective occurrence 71* may be based, at least in part, on a hypothesis 77 that links one or more subjective user states with one or more objective occurrences and in response, at least in part, to an incidence of at least one subjective user state associated with a user 20*. In the case where the computing device 10 is a server, the computing device 10, based at least in part, on the hypothesis 77 and in response to the incidence of the at least one subjective user state associated with a user 20a, may transmit a solicitation or a request for the data indicating incidence of at least one objective occurrence 71* to the user 20a via a mobile device 30, to one or more remote devices including one or more sensors 35, and/or to one or more third party sources 50. Note that in some situations, the mobile device 30 may be solicited for the data indicating incidence of at least one objective occurrence 71c rather than soliciting from the user 20a. That is, in some situations, the solicited data may already have been provided to the mobile device 30 by the user 20a.

In the case where the computing device 10 is a standalone device, the computing device 10, may be configured to solicit objective occurrence data 70* including soliciting data indicating incidence of at least one objective occurrence 70c directly from a user 20b via a user interface 122, from one or more remote devices (e.g., one or more remote network servers or one or more sensors 35), and/or from one or more third party sources 50 via at least one of a wireless or wired network 40. After soliciting for the data indicating incidence of at least one objective occurrence 71*, the computing device 10 (e.g., either in the case where the computing device 10 is a server or in the case where the computing device 10 is a standalone device) may be further designed to acquire the data indicating incidence of at least one objective occurrence 71* as well as to acquire other data indicating other incidences of objective occurrences (e.g., data indicating incidence of at least a second objective occurrence 72*, and so forth). Examples of the types of objective occurrences that may be indicated by the objective occurrence data 70* include, for example, ingestions of food items, medicines, or nutraceutical by a user 20*, exercise routines executed a user 20*, social or recreational activities of a user 20*, activities performed by third parties, geographical locations of a user 20*, external events, physical characteristics of a user 20* at any given moment in time, and so forth.

In some embodiments, the computing device 10 may be configured to acquire subjective user state data 60* including data indicating incidence of at least one subjective user state 61* associated with a user 20*. For example, in embodiments where the computing device 10 is a server, the computing device 10 may acquire subjective user state data 60a including data indicating incidence of at least one subjective user state 61a associated with a user 20a. Such data may be acquired from the user 20a via a mobile device 30 or from other sources such as other network servers that may have previously stored such data and through at least one of a wireless network or a wired network 40. In embodiments where the computing device 10 is a standalone device, the computing device 10 may acquire subjective user state data 60b including data indicating incidence of at least one subjective user state 61b associated with a user 20b. Such data may be acquired from the user 20b via a user interface 122.

Note that in various alternative implementations, the subjective user state data 60* may include data that indicates multiple subjective user states associated with a user 20*. For ease of illustration and explanation, each of the subjective user state data 60a and the subjective user state data 60b illustrated in FIGS. 1a and 1b have been depicted as having only data indicating incidence of at least one subjective user state 61* (e.g., 61a or 61b) and data indicating incidence of at least a second subjective user state 62* (e.g., 62a or 62b). However, in alternate implementations, the subjective user state data 60* may further include data indicating incidences of at least a third, a fourth, a fifth, and so forth, subjective user states associated with a user 20*.

Examples of subjective user states that may be indicated by the subjective user state data 60* include, for example, subjective mental states of a user 20* (e.g., user 20* is sad or angry), subjective physical states of the user 20* (e.g., physical or physiological characteristic of the user 20* such as the presence, absence, elevating, or easing of a pain), subjective overall states of the user 20* (e.g., user 20* is "well"), and/or other subjective user states that only the user 20* can typically indicate.

The one or more sensors 35 illustrated in FIG. 1a may be designed for sensing or monitoring various aspects associated with the user 20a (or user 20b). For example, in some implementations, the one or more sensors 35 may include a global positioning system (GPS) device for determining the one or more locations of the user 20a and/or a physical activity sensor for measuring physical activities of the user 20a.

Examples of a physical activity sensor include, for example, a pedometer for measuring physical activities of the user 20a. In certain implementations, the one or more sensors 35 may include one or more physiological sensor devices for measuring physiological characteristics of the user 20a. Examples of physiological sensor devices include, for example, a blood pressure monitor, a heart rate monitor, a glucometer, and so forth. In some implementations, the one or more sensors 35 may include one or more image capturing devices such as a video or digital camera.

In some embodiments, objective occurrence data 70c that may be acquired from a user 20a via the mobile device 30 (or from user 20b via user interface 122) may be acquired in various forms. For these embodiments, the objective occurrence data 70c may be in the form of blog entries (e.g., microblog entries), status reports, or other types of electronic entries (e.g., diary or calendar entries) or messages. In various implementations, the objective occurrence data 70c acquired from a user 20* may indicate, for example, activities (e.g., exercise or food or medicine intake) performed by the user 20*, certain physical characteristics (e.g., blood pressure or location) associated with the user 20*, or other aspects associated with the user 20* that the user 20* can report objectively. The objective occurrence data 70c may be in the form of a text data, audio or voice data, or image data.

In various embodiments, after acquiring the subjective user state data 60* including data indicating incidence of at least one subjective user state 61* and the objective occurrence data 70* including data indicating incidence of at least one objective occurrence 71*, the computing device 10 may be configured to correlate the acquired subjective user state data 60* with the acquired objective occurrence data 70* by, for example, determining whether there is a sequential relationship between the one or more subjective user states as indicated by the acquired subjective user state data 60* and the one or more objective occurrences indicated by the acquired objective occurrence data 70*.

In some embodiments, and as will be further explained in the operations and processes to be described herein, the computing device 10 may be further configured to present one or more results of the correlation. In various embodiments, the one or more correlation results 80 may be presented to a user 20* and/or to one or more third parties in various forms (e.g., in the form of an advisory, a warning, a prediction, and so forth). The one or more third parties may be other users 20* (e.g., microbloggers), health care providers, advertisers, and/or content providers.

As illustrated in FIG. 1b, computing device 10 may include one or more components and/or sub-modules. As those skilled in the art will recognize, these components and sub-modules may be implemented by employing hardware (e.g., in the form of circuitry such as application specific integrated circuit or ASIC, field programmable gate array or FPGA, or other types of circuitry), software, a combination of both hardware and software, or a general purpose computing device executing instructions included in a signal-bearing medium. In various embodiments, computing device 10 may include an objective occurrence data solicitation module 101, a subjective user state data acquisition module 102, an objective occurrence data acquisition module 104, a correlation module 106, a presentation module 108, a network interface 120 (e.g., network interface card or NIC), a user interface 122 (e.g., a display monitor, a touchscreen, a keypad or keyboard, a mouse, an audio system including a microphone and/or speakers, an image capturing system including digital and/or video camera, and/or other types of interface devices), one or more applications 126 (e.g., a web 2.0 application, a voice recognition application, and/or other applications), and/or memory 140, which may include at least one hypothesis 77 and historical data 78.

FIG. 2a illustrates particular implementations of the objective occurrence data solicitation module 101 of the computing device 10 of FIG. 1b. The objective occurrence data solicitation module 101 may be configured to solicit at least a portion of objective occurrence data 70* including soliciting data indicating incidence of at least one objective occurrence 71*. In various implementations, the solicitation of the data indicating incidence of at least one objective occurrence 71* by the objective occurrence data solicitation module 101 may be prompted based, at least in part, on a hypothesis 77 that links one or more objective occurrences with one or more subjective user states and in response, at least in part, to incidence of at least one subjective user state associated with a user 20*. For example, if an occurrence or incidence of a subjective user state (e.g., a hangover by a user 20*) has been reported, and if the hypothesis 77 links the same type of subjective user state (e.g., a hangover) to an objective occurrence (e.g., consumption of alcohol), then the solicitation of the data indicating incidence of at least one objective occurrence 71* may be to solicit data that would indicate an objective occurrence associated with the user 20* (e.g., consumption of alcohol) that occurred prior to the reported hangover by the user 20*.

The objective occurrence data solicitation module 101 may include one or more sub-modules in various alternative implementations. For example, in various implementations, the objective occurrence data solicitation module 101 may include a requesting module 202 configured to request for at least a portion of objective occurrence data 70* including requesting for data indicating incidence of at least one objective occurrence 71*. The requesting module 202 may further include one or more sub-modules. For example, in some implementations, such as when the computing device 10 is a standalone device, the requesting module 202 may include a user interface requesting module 204 configured to request for data indicating incidence of at least one objective occurrence 71* via a user interface 122. The user interface requesting module 204, in some cases, may further include a request indication module 205 configured to indicate a request for data indicating incidence of at least one objective occurrence 71* via the user interface 122 (e.g., indicating through at least a display system including a display monitor or touchscreen, or indicating via an audio system including a speaker).

In some implementations, such as when the computing device 10 is a server, the requesting module 202 may include a network interface requesting module 206 configured to request for at least data indicating incidence of at least one objective occurrence 71* via a network interface 120. The requesting module 202 may include other sub-modules in various alternative implementations. For example, in some implementations, the requesting module 202 may include a request transmission module 207 configured to transmit a request to be provided with at least data indicating incidence of at least one objective occurrence 71*. Alternatively or in the same implementations, the requesting module 202 may include a request access module 208 configured to transmit a request to have access to at least data indicating incidence of at least one objective occurrence 71*.

In the same or different implementations, the network interface requesting module 206 may include a configuration module 209 designed to configure (e.g., remotely configure) one or more remote devices (e.g., a remote network server, a mobile device 30, or some other network device) to provide at least data indicating incidence of at least one objective occurrence 71*. In the same or different implementations, the requesting module 202 may include a directing/instructing module 210 configured to direct or instruct a remote device (e.g., transmitting directions or instructions to the remote device such as a remote network server or the mobile device 30) to provide at least data indicating incidence of at least one objective occurrence 71*.

The requesting module 202 may include other sub-modules in various alternative implementations. These sub-modules may be included with the requesting module 202 regardless of whether the computing device 10 is a server or a standalone device. For example, in some implementations, the requesting module 202 may include a motivation provision module 212 configured to provide, among other things, a motivation for requesting for the data indicating incidence of at least one objective occurrence 71*. In the same or different implementations, the requesting module 202 may include a selection request module 214 configured to, among other things, request a user 20* for a selection of an objective occurrence from a plurality of indicated alternative objective occurrences (e.g., asking the user 20* through the user interface 122* to select from alternative choices of "bad weather," "good weather," "consumed alcohol," "jogging for one hour," and so forth).

In the same or different implementations, the requesting module 202 may include a confirmation request module 216 configured to request confirmation of an incidence of at least one objective occurrence (e.g., asking a user 20* through the user interface 122* whether the user 20* ate spicy foods for dinner). In the same or different implementations, the requesting module 202 may include a time/temporal element request module 218 configured to, among other things, request for an indication of a time or temporal element associated with an incidence of at least one objective occurrence (e.g., asking the user 20* via the user interface 122* whether the user 20* ate lunch before, after, or during when the user 20* felt tired?).

In various implementations, the objective occurrence data solicitation module 101 of FIG. 2a may include a hypothesis referencing module 220 configured to, among other things, reference at least one hypothesis 77, which in some cases, may be stored in memory 140.

FIG. 2b illustrates particular implementations of the subjective user state data acquisition module 102 of the computing device 10 of FIG. 1b. In brief, the subjective user state data acquisition module 102 may be designed to, among other things, acquire subjective user state data 60* including data indicating at least one subjective user state 61* associated with a user 20*. In various embodiments, the subjective user state data acquisition module 102 may be further designed to acquire data indicating at least a second subjective user state 62* associated with the user 20*, data indicating at least a third subjective user state associated with the user 20*, and so forth. In some embodiments, the subjective user state data acquisition module 102 may include a subjective user state data reception module 224 configured to receive the subjective user state data 60* including the data indicating incidence of the at least one subjective user state 61* associated with the user 20*, the data indicating incidence of the at least a second subjective user state 62* associated with the user 20*, and so forth. In some implementations, the subjective user state data reception module 224 may further include a user interface reception module 226 configured to receive, via a user interface 122, subjective user state data 60* including at least the data indicating incidence of at least one subjective user state 61* associated with a user 20*. In the same or different implementations, the subjective user state data reception module 224 may include a network interface reception module 227 configured to receive, via a network interface 120, subjective user state data 60* including at least the data indicating incidence of at least one subjective user state 61* associated with a user 20*.

The subjective user state data acquisition module 102, in various implementations, may include a time data acquisition module 228 configured to acquire (e.g., receive or generate) time and/or temporal elements associated with one or more objective occurrences. In some implementations, the time data acquisition module 228 may include a time stamp acquisition module 230 for acquiring (e.g., acquiring either by receiving or by generating) one or more time stamps associated with one or more objective occurrences In the same or different implementations, the time data acquisition module 228 may include a time interval acquisition module 231 for acquiring (e.g., either by receiving or generating) indications of one or more time intervals associated with one or more objective occurrences.

FIG. 2c illustrates particular implementations of the objective occurrence data acquisition module 104 of the computing device 10 of FIG. 1b. In brief, the objective occurrence data acquisition module 104 may be configured to, among other things, acquire objective occurrence data 70* including data indicating incidence of at least one objective occurrence 71*, data indicating incidence of at least a second objective occurrence 72*, and so forth. As further illustrated, in some implementations, the objective occurrence data acquisition module 104 may include an objective occurrence data reception module 234 configured to, among other things, receive objective occurrence data 70* from a user 20*, from one or more third party sources 50 (e.g., one or more third parties), or from one or more remote devices such as one or more sensors 35 or one or more remote network servers.

The objective occurrence data reception module 234, in turn, may further include one or more sub-modules. For example, in some implementations, such as when the computing device 10 is a standalone device, the objective occurrence data reception module 234 may include a user interface data reception module 235 configured to receive objective occurrence data 70* via a user interface 122 (e.g., a keyboard, a mouse, a touchscreen, a microphone, an image capturing device such as a digital camera, and so forth). In some cases, the objective occurrence data 70* (e.g., objective occurrence data 70c) to be received via the user interface 122 may have been provided by and originate from a user 20b. In other cases, the objective occurrence data 70* to be received via the user interface 122 may have originated from one or more third party sources 50 or from one or more remote sensors 35 and provided by user 20b. In some implementations, such as when the computing device 10 is a server, the objective occurrence data reception module 234 may include a network interface data reception module 236 configured to, among other things, receive objective occurrence data 70* from at least one of a wireless network or a wired network 40. The network interface data reception module 236 may directly or indirectly receive the objective occurrence data 70* from a user 20a, from one or more third party sources 50, or from one or more remote devices such as one or more sensors 35.

Figure 2D:
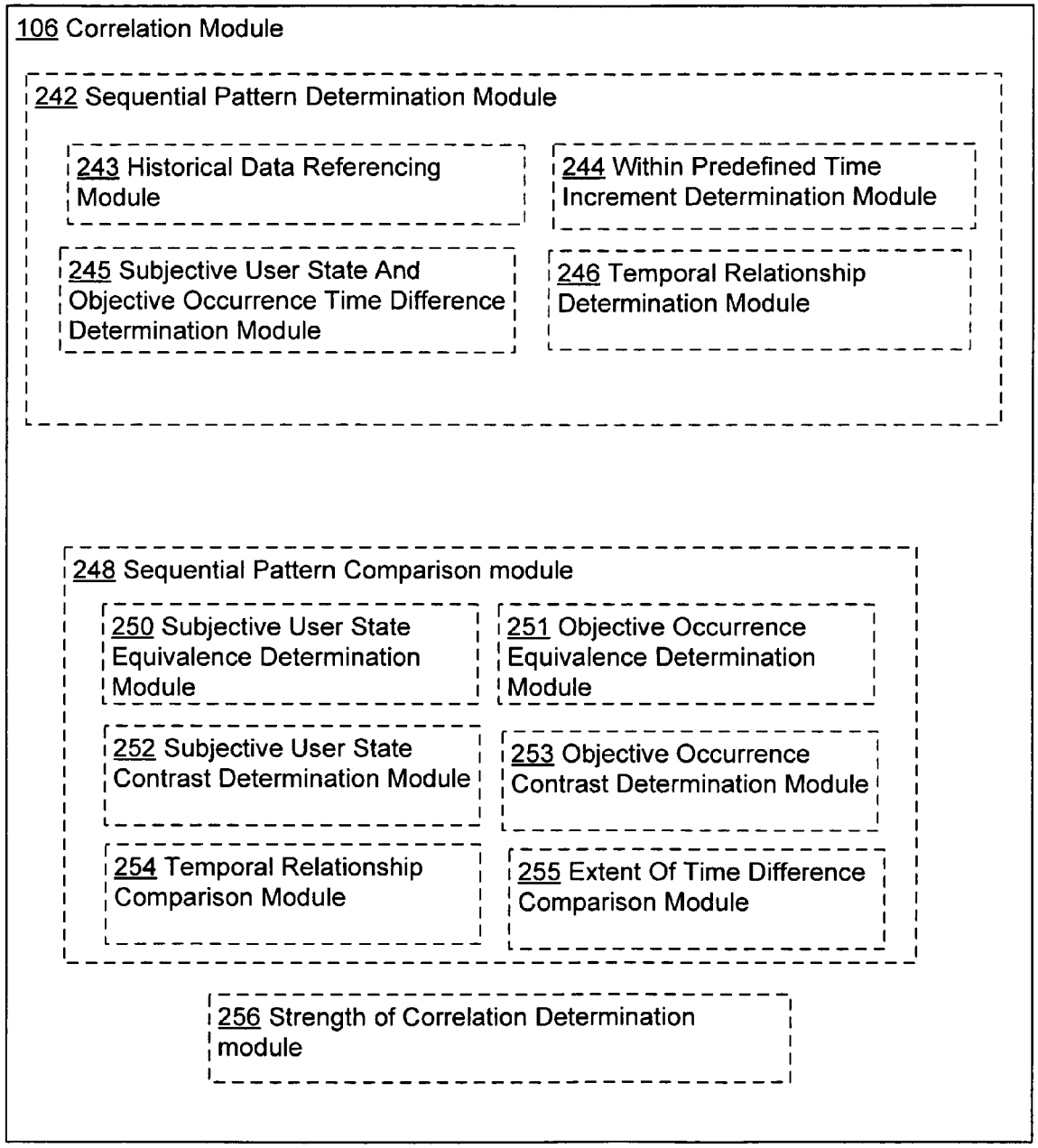
FIG. 2d shows another perspective of the correlation module 106 of the computing device 10 of FIG. 1b.

Turning now to FIG. 2d illustrating particular implementations of the correlation module 106 of the computing device 10 of FIG. 1b. The correlation module 106 may be configured to, among other things, correlate subjective user state data 60* with objective occurrence data 70* based, at least in part, on a determination of at least one sequential pattern of at least one objective occurrence and at least one subjective user state. In various embodiments, the correlation module 106 may include a sequential pattern determination module 242 configured to determine one or more sequential patterns of one or more incidences of subjective user states and one or more incidences of objective occurrences.

The sequential pattern determination module 242, in various implementations, may include one or more sub-modules that may facilitate in the determination of one or more sequential patterns. As depicted, the one or more sub-modules that may be included in the sequential pattern determination module 242 may include, for example, a "within predefined time increment determination" module 244, a temporal relationship determination module 246, a subjective user state and objective occurrence time difference determination module 245, and/or a historical data referencing module 243. In brief, the within predefined time increment determination module 244 may be configured to determine whether an incidence of at least one subjective user state associated with a user 20* occurred within a predefined time increment from an incidence of at least one objective occurrence. For example, determining whether a user 20* "feeling bad" (i.e., a subjective user state) occurred within ten hours (i.e., predefined time increment) of eating a large chocolate sundae (i.e., an objective occurrence). Such a process may be used in order to filter out events that are likely not related or to facilitate in determining the strength of correlation between subjective user state data 60* and objective occurrence data 70*. For example, if the user 20* "feeling bad" occurred more than 10 hours after eating the chocolate sundae, then this may indicate a weaker correlation between a subjective user state (e.g., feeling bad) and an objective occurrence (e.g., eating a chocolate sundae).

The temporal relationship determination module 246 of the sequential pattern determination module 242 may be configured to determine the temporal relationships between one or more incidences of subjective user states associated with a user 20* and one or more incidences of objective occurrences. For example, this determination may entail determining whether an incidence of a particular subjective user state (e.g., sore back) occurred before, after, or at least partially concurrently with an incidence of a particular objective occurrence (e.g., sub-freezing temperature).

The subjective user state and objective occurrence time difference determination module 245 of the sequential pattern determination module 242 may be configured to determine the extent of time difference between an incidence of at least one subjective user state associated with a user 20* and an incidence of at least one objective occurrence. For example, determining how long after taking a particular brand of medication (e.g., objective occurrence) did a user 20* feel "good" (e.g., subjective user state).

The historical data referencing module 243 of the sequential pattern determination module 242 may be configured to reference historical data 78 in order to facilitate in determining sequential patterns. For example, in various implementations, the historical data 78 that may be referenced may include, for example, general population trends (e.g., people having a tendency to have a hangover after drinking or ibuprofen being more effective than aspirin for toothaches in the general population), medical information such as genetic, metabolome, or proteome information related to the user 20* (e.g., genetic information of the user 20* indicating that the user 20* is susceptible to a particular subjective user state in response to occurrence of a particular objective occurrence), or historical sequential patterns such as known sequential patterns of the general population or of the user 20* (e.g., people tending to have difficulty sleeping within five hours after consumption of coffee). In some instances, such historical data 78 may be useful in associating one or more incidences of subjective user states associated with a user 20* with one or more incidences of objective occurrences.

In some embodiments, the correlation module 106 may include a sequential pattern comparison module 248. As will be further described herein, the sequential pattern comparison module 248 may be configured to compare two or more sequential patterns with respect to each other to determine, for example, whether the sequential patterns at least substantially match each other or to determine whether the sequential patterns are contrasting sequential patterns.

As depicted in FIG. 2d, in various implementations, the sequential pattern comparison module 248 may further include one or more sub-modules that may be employed in order to, for example, facilitate in the comparison of different sequential patterns. For example, in various implementations, the sequential pattern comparison module 248 may include one or more of a subjective user state equivalence determination module 250, an objective occurrence equivalence determination module 251, a subjective user state contrast determination module 252, an objective occurrence contrast determination module 253, a temporal relationship comparison module 254, and/or an extent of time difference comparison module 255. In some implementations, the sequential pattern comparison module 248 may be employed in order to, for example, confirm the veracity of a hypothesis 77.

The subjective user state equivalence determination module 250 of the sequential pattern comparison module 248 may be configured to determine whether subjective user states associated with different sequential patterns are at least substantially equivalent. For example, the subjective user state equivalence determination module 250 may determine whether a first subjective user state of a first sequential pattern is equivalent to a second subjective user state of a second sequential pattern. For instance, suppose a user 20* reports that on Monday he had a stomach ache (e.g., first subjective user state) after eating at a particular restaurant (e.g., a first objective occurrence), and suppose further that the user 20* again reports having a stomach ache (e.g., a second subjective user state) after eating at the same restaurant (e.g., a second objective occurrence) on Tuesday, then the subjective user state equivalence determination module 250 may be employed in order to compare the first subjective user state (e.g., stomach ache) with the second subjective user state (e.g., stomach ache) to determine whether they are equivalent. Note that in this example, the first sequential pattern may represent a hypothesis 77 linking a subjective user state (e.g., stomach ache) to an objective occurrence (e.g., eating at a particular restaurant).

In contrast, the objective occurrence equivalence determination module 251 of the sequential pattern comparison module 248 may be configured to determine whether objective occurrences of different sequential patterns are at least substantially equivalent. For example, the objective occurrence equivalence determination module 251 may determine whether a first objective occurrence of a first sequential pattern is equivalent to a second objective occurrence of a second sequential pattern. For instance, in the above example, the objective occurrence equivalence determination module 251 may compare eating at the particular restaurant on Monday (e.g., first objective occurrence) with eating at the same restaurant on Tuesday (e.g., second objective occurrence) in order to determine whether the first objective occurrence is equivalent to the second objective occurrence.

In some implementations, the sequential pattern comparison module 248 may include a subjective user state contrast determination module 252 that may be configured to determine whether subjective user states associated with different sequential patterns are contrasting subjective user states. For example, the subjective user state contrast determination module 252 may determine whether a first subjective user state of a first sequential pattern is a contrasting subjective user state from a second subjective user state of a second sequential pattern. To illustrate, suppose a user 20* reports that he felt very "good" (e.g., first subjective user state) after jogging for an hour (e.g., first objective occurrence) on Monday, but reports that he felt "bad" (e.g., second subjective user state) when he did not exercise (e.g., second objective occurrence) on Tuesday, then the subjective user state contrast determination module 252 may compare the first subjective user state (e.g., feeling good) with the second subjective user state (e.g., feeling bad) to determine that they are contrasting subjective user states.

In some implementations, the sequential pattern comparison module 248 may include an objective occurrence contrast determination module 253 that may be configured to determine whether objective occurrences of different sequential patterns are contrasting objective occurrences. For example, the objective occurrence contrast determination module 253 may determine whether a first objective occurrence of a first sequential pattern is a contrasting objective occurrence from a second objective occurrence of a second sequential pattern. For instance, in the previous example, the objective occurrence contrast determination module 253 may compare the "jogging" on Monday (e.g., first objective occurrence) with the "no jogging" on Tuesday (e.g., second objective occurrence) in order to determine whether the first objective occurrence is a contrasting objective occurrence from the second objective occurrence. Based on the contrast determination, an inference may be made that the user 20* may feel better by jogging rather than by not jogging at all.

In some embodiments, the sequential pattern comparison module 248 may include a temporal relationship comparison module 254 that may be configured to make comparisons between different temporal relationships of different sequential patterns. For example, the temporal relationship comparison module 254 may compare a first temporal relationship between a first subjective user state and a first objective occurrence of a first sequential pattern with a second temporal relationship between a second subjective user state and a second objective occurrence of a second sequential pattern in order to determine whether the first temporal relationship at least substantially matches the second temporal relationship.

For example, referring back to the earlier restaurant example, suppose the user 20* eating at the particular restaurant (e.g., first objective occurrence) and the subsequent stomach ache (e.g., first subjective user state) on Monday represents a first sequential pattern while the user 20* eating at the same restaurant (e.g., second objective occurrence) and the subsequent stomach ache (e.g., second subjective user state) on Tuesday represents a second sequential pattern. In this example, the occurrence of the stomach ache after (rather than before or concurrently) eating at the particular restaurant on Monday represents a first temporal relationship associated with the first sequential pattern while the occurrence of a second stomach ache after (rather than before or concurrently) eating at the same restaurant on Tuesday represents a second temporal relationship associated with the second sequential pattern.

Under such circumstances, the temporal relationship comparison module 254 may compare the first temporal relationship to the second temporal relationship in order to determine whether the first temporal relationship and the second temporal relationship at least substantially match (e.g., stomach aches in both temporal relationships occurring after eating at the restaurant). Such a match may result in the inference that a stomach ache is associated with eating at the particular restaurant and may, in some instances, confirm the veracity of a hypothesis 77.

In some implementations, the sequential pattern comparison module 248 may include an extent of time difference comparison module 255 that may be configured to compare the extent of time differences between incidences of subjective user states and incidences of objective occurrences of different sequential patterns. For example, the extent of time difference comparison module 255 may compare the extent of time difference between incidence of a first subjective user state and incidence of a first objective occurrence of a first sequential pattern with the extent of time difference between incidence of a second subjective user state and incidence of a second objective occurrence of a second sequential pattern. In some implementations, the comparisons may be made in order to determine that the extent of time differences of the different sequential patterns at least substantially or proximately match.

In some embodiments, the correlation module 106 may include a strength of correlation determination module 256 for determining a strength of correlation between subjective user state data 60* and objective occurrence data 70*. In some implementations, the strength of correlation may be determined based, at least in part, on the results provided by the other sub-modules of the correlation module 106 (e.g., the sequential pattern determination module 242, the sequential pattern comparison module 248, and their sub-modules).

Figure 2E:
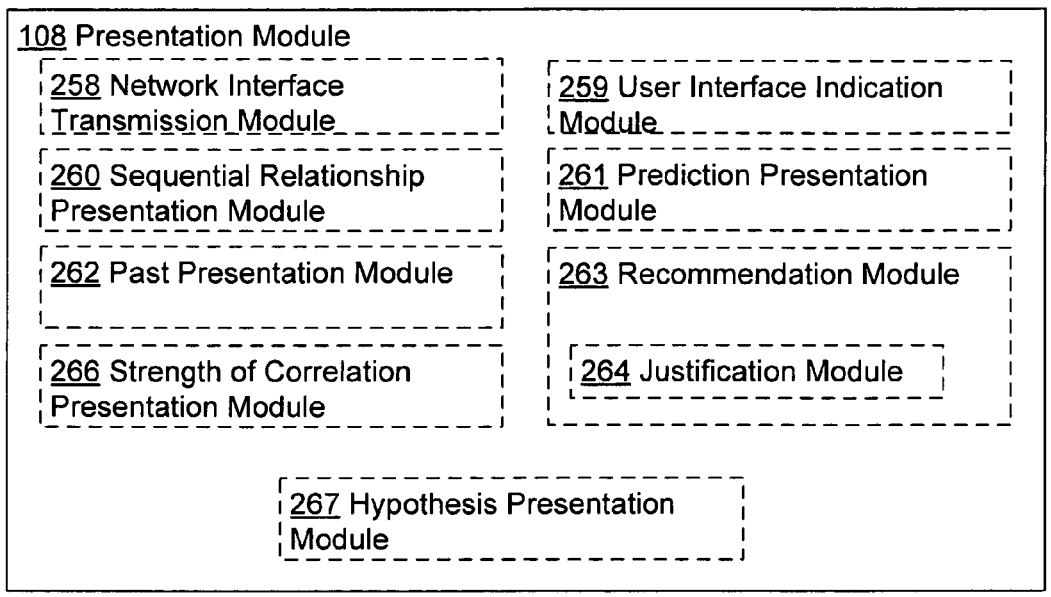
FIG. 2e shows another perspective of the presentation module 108 of the computing device 10 of FIG. 1b.

FIG. 2e illustrates particular implementations of the presentation module 108 of the computing device 10 of FIG. 1b. In various implementations, the presentation module 108 may be configured to present, for example, one or more results of the correlation operations performed by the correlation module 106. In some implementations, the presentation module 108 may include a network interface transmission module 258 configured to transmit one or more results of a correlation operation performed by the correlation module 106 via a network interface 120 (e.g., NIC). In the same or different implementations, the presentation module 108 may include a user interface indication module 259 configured to indicate one or more results of a correlation operation performed by the correlation module 106 via a user interface 122 (e.g., display monitor or audio system including a speaker).

The presentation module 108 may be particularly designed to present one or more results of a correlation operation performed by the correlation module 106 in a variety of different forms in various alternative embodiments. For example, in some implementations, the presentation of the one or more results may entail the presentation module 108 presenting to the user 20* (or some other third party) an indication of a sequential relationship between a subjective user state and an objective occurrence associated with the user 20* (e.g., "whenever you eat a banana, you have a stomach ache"). In alternative implementations, other ways of presenting the results of the correlation may be employed. For example, in various alternative implementations, a notification may be provided to notify past tendencies or patterns associated with a user 20*. In some implementations, a notification of a possible future outcome may be provided. In other implementations, a recommendation for a future course of action based on past patterns may be provided. These and other ways of presenting the correlation results will be described in the processes and operations to be described herein.

In order to present the one or more results of a correlation operation performed by the correlation module 106, the presentation module 108 may include one or more sub-modules. For example, in some implementations, the presentation module 108 may include a sequential relationship presentation module 260 configured to present an indication of a sequential relationship between at least one subjective user state of a user 20* and at least one objective occurrence. In the same or different implementations, the presentation module 108 may include a prediction presentation module 261 configured to present a prediction of a future subjective user state of a user 20* resulting from a future objective occurrence associated with the user 20*. In the same or different implementations, the prediction presentation module 261 may also be designed to present a prediction of a future subjective user state of a user 20* resulting from a past objective occurrence associated with the user 20*. In some implementations, the presentation module 108 may include a past presentation module 262 that is designed to present a past subjective user state of a user 20* in connection with a past objective occurrence associated with the user 20*.

In some implementations, the presentation module 108 may include a recommendation module 263 configured to present a recommendation for a future action based, at least in part, on the results of a correlation of subjective user state data 60* with objective occurrence data 70* as performed by the correlation module 106. In certain implementations, the recommendation module 263 may further include a justification module 264 for presenting a justification for the recommendation presented by the recommendation module 263. In some implementations, the presentation module 108 may include a strength of correlation presentation module 266 for presenting an indication of a strength of correlation between subjective user state data 60* and objective occurrence data 70*.

In various embodiments, the computing device 10 of FIG. 1b may include a network interface 120 that may facilitate in communicating with a user 20a, with one or more sensors 35, and/or with one or more third party sources 50 via a wireless and/or wired network 40. For example, in embodiments where the computing device 10 is a server, the computing device 10 may include a network interface 120 that may be configured to receive from the user 20a subjective user state data 60a. In some embodiments, objective occurrence data 70a, 70b, and/or 70c may also be received through the network interface 120. Examples of a network interface 120 includes, for example, a network interface card (NIC) or other devices or systems for communicating through at least one of a wireless network or wired network 40.

The computing device 10 may also include a memory 140 for storing various data. For example, in some embodiments, memory 140 may be employed in order to store a hypothesis 77 and/or historical data 78. In some implementations, the historical data 78 may include historical subjective user state data of a user 20* that may indicate one or more past subjective user states of the user 20*, and historical objective occurrence data that may indicate one or more past objective occurrences. In the same or different implementations, the historical data 78 may include historical medical data of a user 20* (e.g., genetic, metoblome, proteome information), population trends, historical sequential patterns derived from general population, and so forth. Examples of a memory 140 include, for example, a mass storage device, read only memory (ROM), programmable read only memory (PROM), erasable programmable read-only memory (EPROM), random access memory (RAM), flash memory, synchronous random access memory (SRAM), dynamic random access memory (DRAM), and so forth.

In various embodiments, the computing device 10 may include a user interface 122 to communicate directly with a user 20b. For example, in embodiments in which the computing device 10 is a standalone device such as a handheld device (e.g., cellular telephone, smartphone, PDA, and so forth), the user interface 122 may be configured to directly receive from the user 20b subjective user state data 60* and/or objective occurrence data 70*. In some implementations, the user interface 122 may also be designed to visually or audiably present the results of correlating subjective user state data 60* with objective occurrence data 70*. The user interface 122 may include, for example, one or more of a display monitor, a touch screen, a key board, a key pad, a mouse, an audio system including a microphone and/or one or more speakers, an imaging system including a digital or video camera, and/or other user interface devices.

Figure 2F:
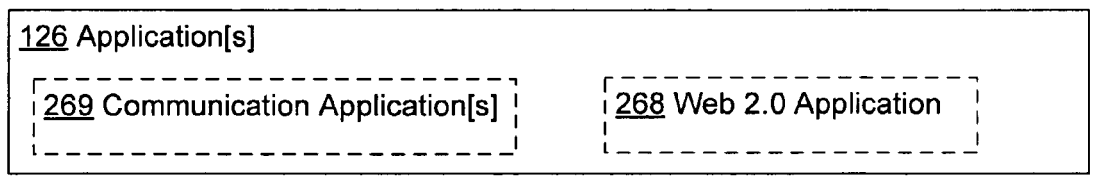
FIG. 2f shows another perspective of the one or more applications 126 of the computing device 10 of FIG. 1b.

FIG. 2f illustrates particular implementations of the one or more applications 126 of FIG. 1b. For these implementations, the one or more applications 126 may include, for example, one or more communication applications 269 such as a text messaging application and/or an audio messaging application including a voice recognition system application. In some implementations, the one or more applications 126 may include a web 2.0 application 268 to facilitate communication via, for example, the World Wide Web.

The various features and characteristics of the components, modules, and sub-modules of the computing device 10 presented thus far will be described in greater detail with respect to the processes and operations to be described herein. Note that the subjective user state data 60* may be in a variety of forms including, for example, text messages (e.g., blog entries, microblog entries, instant messages, text email messages, and so forth), audio messages, and/or images (e.g., an image capturing user's facial expression or gestures).

Figure 2G:
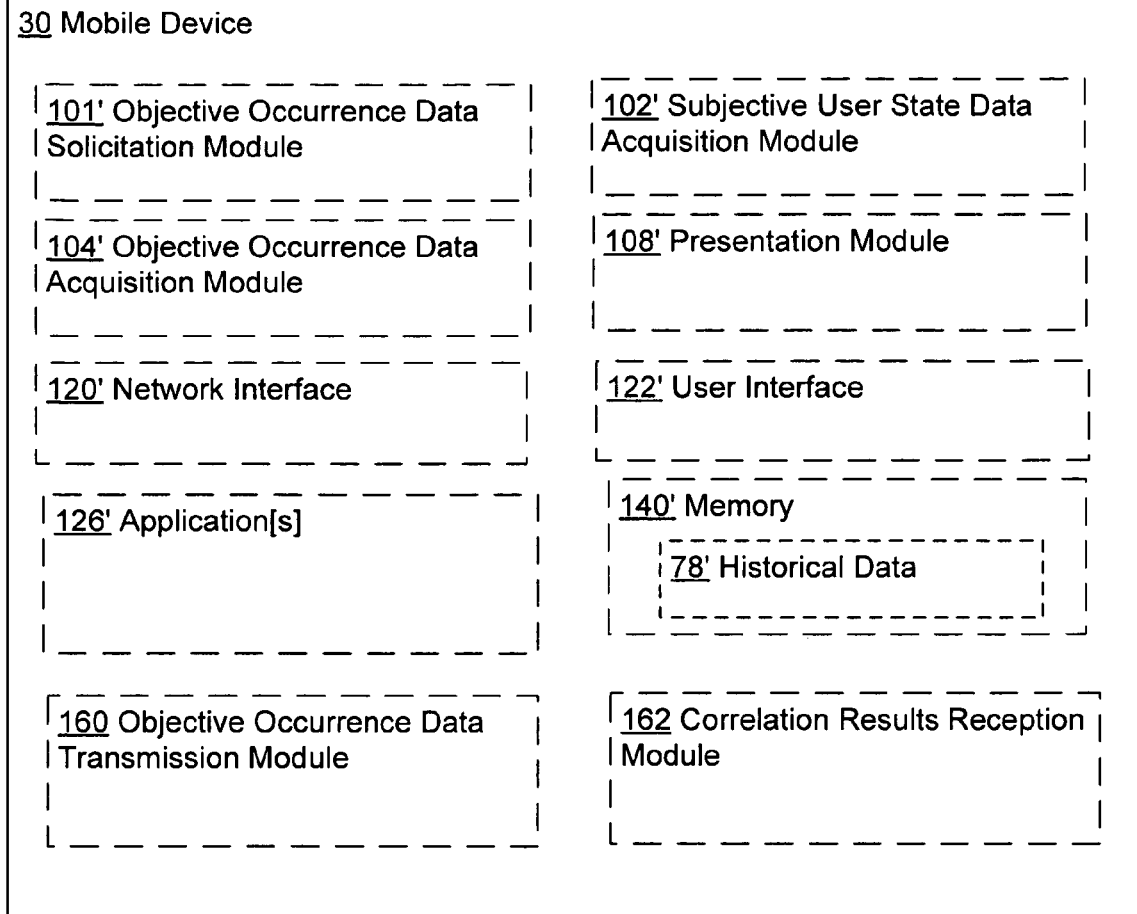

Referring to FIG. 2g illustrating particular implementations of the mobile device 30 of FIG. 1a. The mobile device 30 includes some modules that are the same as some of the modules that may be included in the computing device 10. These components may have the same features and perform the same or similar types of functions as those of their corresponding counterparts in the computing device 10. For example, and just like the computing device 10, the mobile device 30 may include an objective occurrence data solicitation module 101', a subjective user state data acquisition module 102', an objective occurrence data acquisition module 104', a presentation module 108', a network interface 120', a user interface 122', one or more application [s] 126' (e.g., including a Web 2.0 application), and/or memory 140' (including historical data 78').

In various implementations, in addition to these components, the mobile device 30 may include an objective occurrence data transmission module 160 that is configured to transmit (e.g., transmit via a wireless and/or wired network 40) at least a portion of objective occurrence data 70* including data indicating incidence of at least one objective occurrence 71*. In some implementations, the subjective user state data 60a and/or at least a portion of the objective occurrence data 70* may be transmitted to a network server such as computing device 10. In the same or different implementations, the mobile device 30 may include a correlation results reception module 162 that may be configured to receive, via a wireless and/or wired network 40, results of correlation of subjective user state data 60* with objective occurrence data 70*. In some implementations, such a correlation may have been performed at a network server (e.g., computing device 10).

FIG. 2h illustrates particular implementations of the objective occurrence data solicitation module 101' of the mobile device 30 of FIG. 2g. As depicted, the objective occurrence data solicitation module 101' may include some components that are the same or similar to some of the components that may be included in the objective occurrence data solicitation module 101 of the computing device 10 as illustrated in FIG. 2a. For example, the objective occurrence data solicitation module 101' may include a requesting module 202' that further includes a user interface requesting module 204' (and a request indication module 205' included with the user interface requesting module 204'), a network interface requesting module 206', a request transmission module 207', a request access module 208', a configuration module 209', a directing/instructing module 210', a motivation provision module 212', a selection request module 214', a confirmation request module 216' and a time/temporal element request module 218'. As will be further described herein, these components may have the same features and perform the same functions as their counterparts in the computing device 10.

In addition, and unlike the computing device 10, the objective occurrence data solicitation module 101' of the mobile device 30 may include a request to solicit reception module 270 that may be configured to receive a request to solicit data indicating incidence of at least one objective occurrence 71*. Such a request, in some implementations, may be remotely generated (e.g. remotely generated at the computing device 10) based, at least in part, on a hypothesis 77 and, in some cases, in response, at least in part, to an incidence of at least one objective occurrence.

Figure 2I:
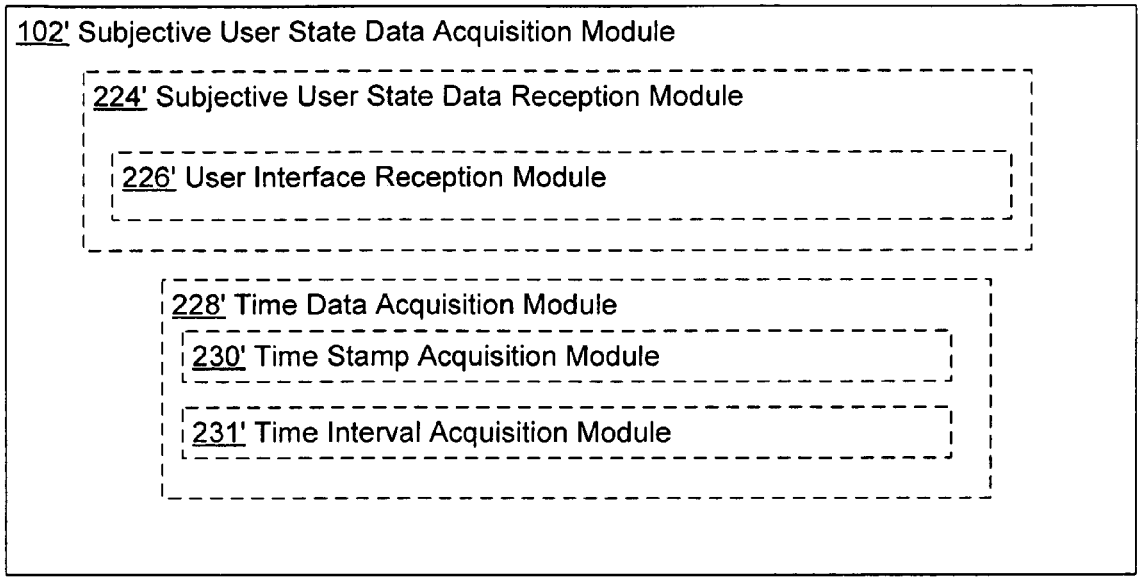
FIG. 2i shows another perspective of the subjective user state data acquisition module 102' of the mobile device 30 of FIG. 2g.

FIG. 2i illustrates particular implementations of the subjective user state data acquisition module 102' of the mobile device 30 of FIG. 2g. The subjective user state data acquisition module 102' may include some components that are the same or similar to some of the components that may be included in the subjective user state data acquisition module 102 (see FIG. 2b) of the computing device 10. These components may perform the same or similar functions as their counterparts in the subjective user state data acquisition module 102 of the computing device 10. For example, the subjective user state data acquisition module 102' may include a subjective user state data reception module 224' and a time data acquisition module 228'. Similar to their counterparts in the computing device 10 and performing similar roles, the subjective user state data reception module 224' may include a user interface reception module 226' while the time data acquisition module 228' may include a time stamp acquisition module 230' and a time interval acquisition module 231'.

Figure 2J:
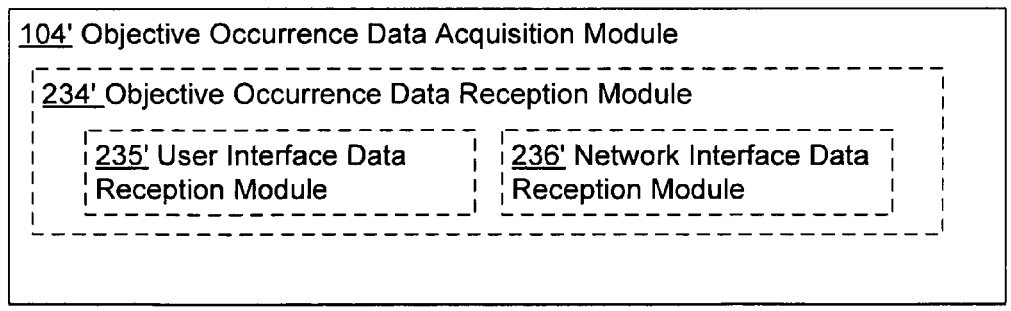
FIG. 2j shows another perspective of the objective occurrence data acquisition module 104' of the mobile device 30 of FIG. 2g.

Referring to FIG. 2j illustrating particular implementations of the objective occurrence data acquisition module 104' of the mobile device 30 of FIG. 2g. The objective occurrence data acquisition module 104' may include the same or similar type of components that may be included in the objective occurrence data acquisition module 104 (see FIG. 2c) of the computing device 10. For example, the objective occurrence data acquisition module 104' may include an objective occurrence data reception module 234' (which may further include a user interface data reception module 235' and/or a network interface data reception module 236').

Figure 2K:
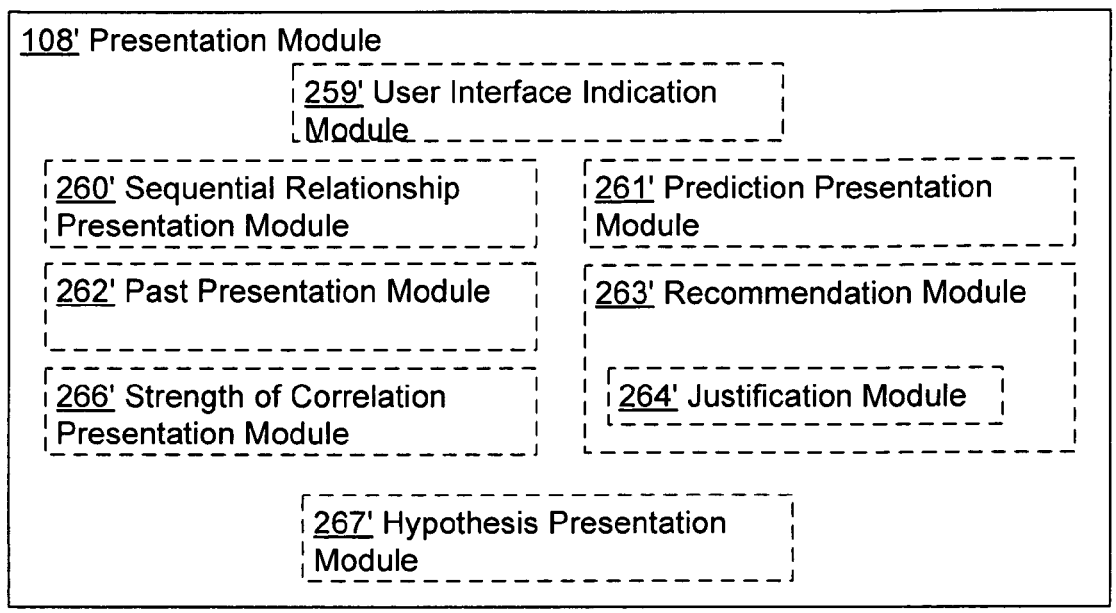
FIG. 2k shows another perspective of the presentation module 108' of the mobile device 30 of FIG. 2g.
Figure 2L:
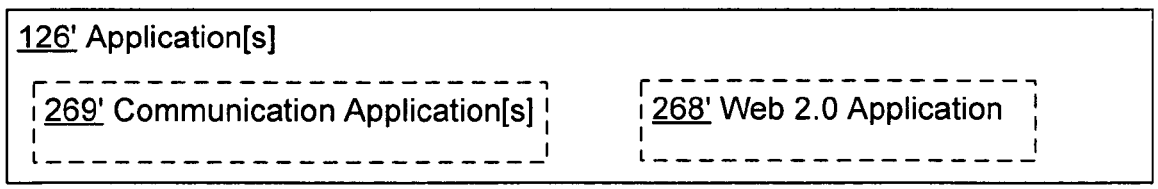
FIG. 2l shows another perspective of the one or more applications 126' of the mobile device 30 of FIG. 2g.

FIG. 2k illustrates particular implementations of the presentation module 108' of the mobile device 30 of FIG. 2g. In various implementations, the presentation module 108' may include some of the same components that may be included in the presentation module 108 (see FIG. 2e) of the computing device 10. For example, the presentation module 108' may include a user interface indication module 259', a sequential relationship presentation module 260', a prediction presentation module 261', a past presentation module 262', a recommendation module 263' (which may further include a justification module 264'), and/or a strength of correlation presentation module 266'.

FIG. 21 illustrates particular implementations of the one or more applications 126' of the mobile device 30 of FIG. 2g. In various implementations, the one or more applications 126' may include the same or similar applications included in the one or more applications 126 of the computing device 10 (see FIG. 2f). For example, the one or more applications 126' may include one or more communication applications 269' and a web 2.0 application 268' performing similar functions as their counterparts in the computing device 10.

A more detailed discussion of these components (e.g., modules and interfaces) that may be included in the mobile device 30 and those that may be included in the computing device 10 will be provided with respect to the processes and operations to be described herein.

Figure 3:
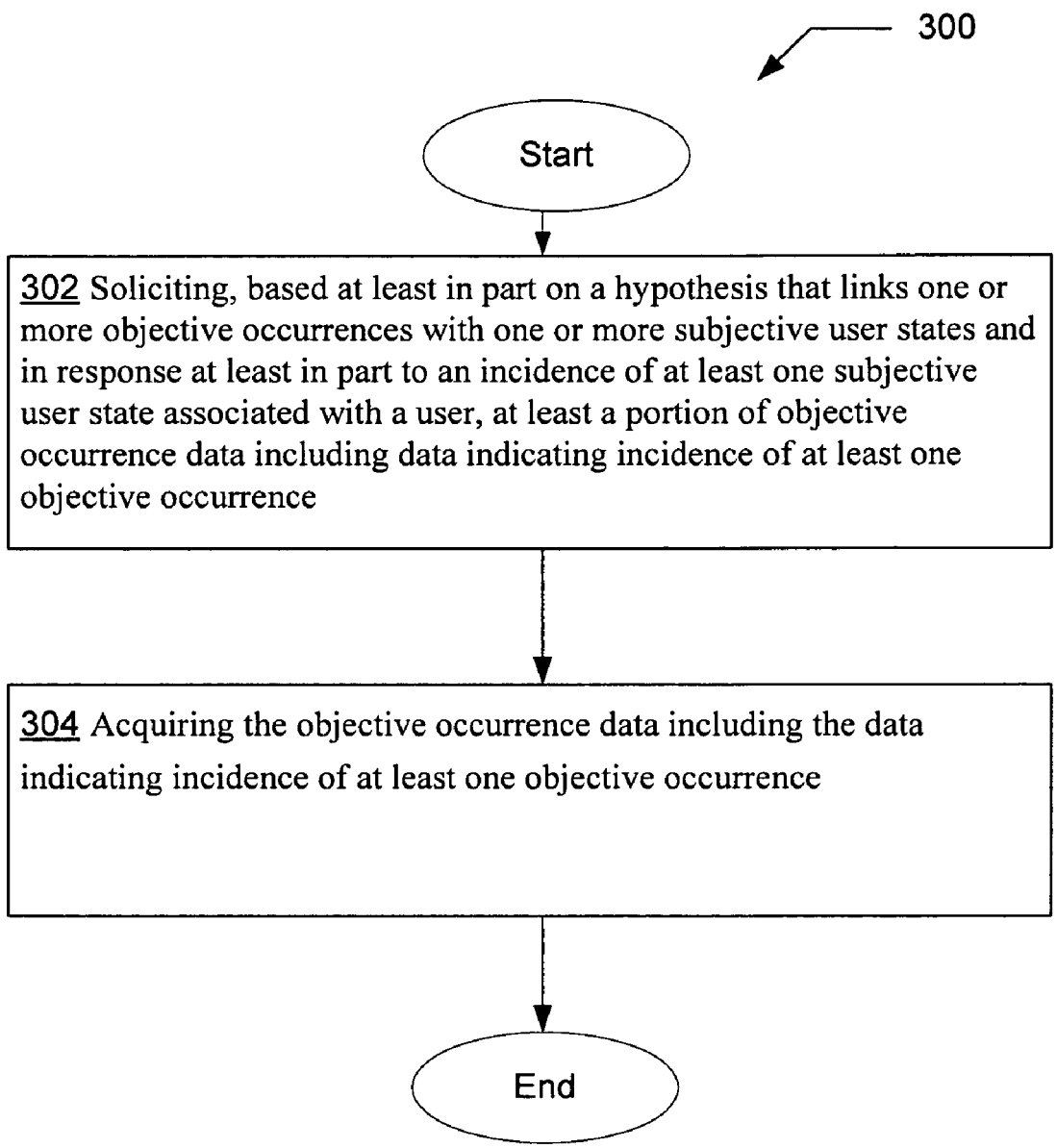
FIG. 3 is a high-level logic flowchart of a process.

FIG. 3 illustrates an operational flow 300 representing example operations related to, among other things, hypothesis based solicitation and acquisition of at least a portion of objective occurrence data 70* including data indicating incidence of at least one objective occurrence 71*. In some embodiments, the operational flow 300 may be executed by, for example, the computing device 10 of FIG. 1b, which may be a server or a standalone device. Alternatively, the operation flow 300 may be executed by, for example, the mobile device 30 of FIG. 1a.

In FIG. 3 and in the following figures that include various examples of operational flows, discussions and explanations may be provided with respect to the above-described exemplary environment of FIGS. 1a and 1b, and/or with respect to other examples (e.g., as provided in FIGS. 2a-2l) and contexts. However, it should be understood that the operational flows may be executed in a number of other environments and contexts, and/or in modified versions of FIGS. 1a, 1b, and 2a-2l. Also, although the various operational flows are presented in the sequence(s) illustrated, it should be understood that the various operations may be performed in other orders other than those which are illustrated, or may be performed concurrently.

Further, in FIG. 3 and in following figures, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

In any event, after a start operation, the operational flow 300 may move to an objective occurrence data solicitation operation 302 for soliciting, based at least in part on a hypothesis that links one or more objective occurrences with one or more subjective user states and in response at least in part to an incidence of at least one subjective user state associated with a user, at least a portion of objective occurrence data including data indicating incidence of at least one objective occurrence. For instance, the objective occurrence data solicitation module 101 of the computing device 10 or the objective occurrence data solicitation module 101' of the mobile device 30 soliciting, based at least in part on a hypothesis 77 (e.g., the computing device 10 referencing a hypothesis 77, or the mobile device 30 receiving a request for soliciting at least a portion of objective occurrence data from the computing device 10, the request being remotely generated by the computing device 10 and sent to the mobile device 30 based at least in part on a hypothesis 77) that links one or more objective occurrences with one or more subjective user states (e.g., a group of users 20* ingesting a particular type of medicine such as aspirin, and the subsequent subjective physical states, such as pain relief, associated with the group of users 20*) and in response at least in part to an incidence of at least one subjective user state (e.g., pain relief by a user 20*) associated with a user 20*, at least a portion of objective occurrence data 70* including data indicating incidence of at least one objective occurrence 71* (e.g., ingestion of aspirin by user 20*).

Note that the solicitation of at least a portion of the objective occurrence data 70*, as described above, may or may not be in reference to solicitation of particular data that indicates an incidence or occurrence of a particular or particular type of objective occurrence. That is, in some embodiments, the solicitation of at least a portion of the objective occurrence data 70* may be in reference to solicitation for objective occurrence data 70* including data indicating incidence of any objective occurrence with respect to, for example, a particular point in time or time interval or with respect to a incidence of a particular subjective user state associated with the user 20*. While in other embodiments, the solicitation of at least a portion of the objective occurrence data 70* may involve soliciting for data indicating occurrence of a particular or particular type of objective occurrence.

The term "soliciting," as will be used herein, may be in reference to direct or indirect solicitation of (e.g., requesting to be provided with, requesting to access, gathering of, or other methods of being provided with or being allowed access to) at least a portion of objective occurrence data 70* from one or more sources. The sources for at least a portion of the objective occurrence data 70* may be a user 20* (e.g., providing objective occurrence data 70c via mobile device 30), a mobile device 30 (e.g., mobile device 30 may have previously obtained the objective occurrence data 70c from the user 20a or from other sources), one or more network servers (not depicted), one or more third party sources 50 (e.g., providing objective occurrence data 70a), or one or more sensors 35 (e.g., providing objective occurrence data 70b).

For example, if the computing device 10 is a server, then the computing device 10 may indirectly solicit at least a portion of objective occurrence data 70c from a user 20a by transmitting, for example, a request for at least the portion of the objective occurrence data 70c to the mobile device 30, which in turn may solicit at least the portion of the objective occurrence data 70c from the user 20a. Alternatively, such data may have already been provided to the mobile device 30, in which case the mobile device 30 merely provides for or allows access to such data. Note that the objective occurrence data 70c that may be provided by the mobile device 30 may have originally been obtained from the user 20a, from one or more third party sources 50, and/or from one or more remote network devices (e.g., sensors 35 or network servers).

In some situations, at least a portion of objective occurrence data 70* may be stored in a network server (not depicted), and such a network server may be solicited for at least portion of the objective occurrence data 70*. In other implementations, objective occurrence data 70a or 70b may be solicited from one or more third party sources 50 (e.g., one or more third parties or one or more network devices such as servers that are associated with one or more third parties) or from one or more sensors 35. In yet other implementations in which the computing device 10 is a standalone device, such as a handheld device to be used directly by a user 20b, the computing device 10 may directly solicit, for example, the objective occurrence data 70c from the user 20b.

Operational flow 300 may further include an objective occurrence data acquisition operation 304 for acquiring the objective occurrence data including the data indicating incidence of at least one objective occurrence. For instance, the objective occurrence data acquisition module 104* of the computing device 10 or the mobile device 30 acquiring (e.g., receiving or accessing by the computing device 10 or by the mobile device 30) the objective occurrence data 70* including the data indicating incidence of at least one objective occurrence 71*.

Figure 4A:
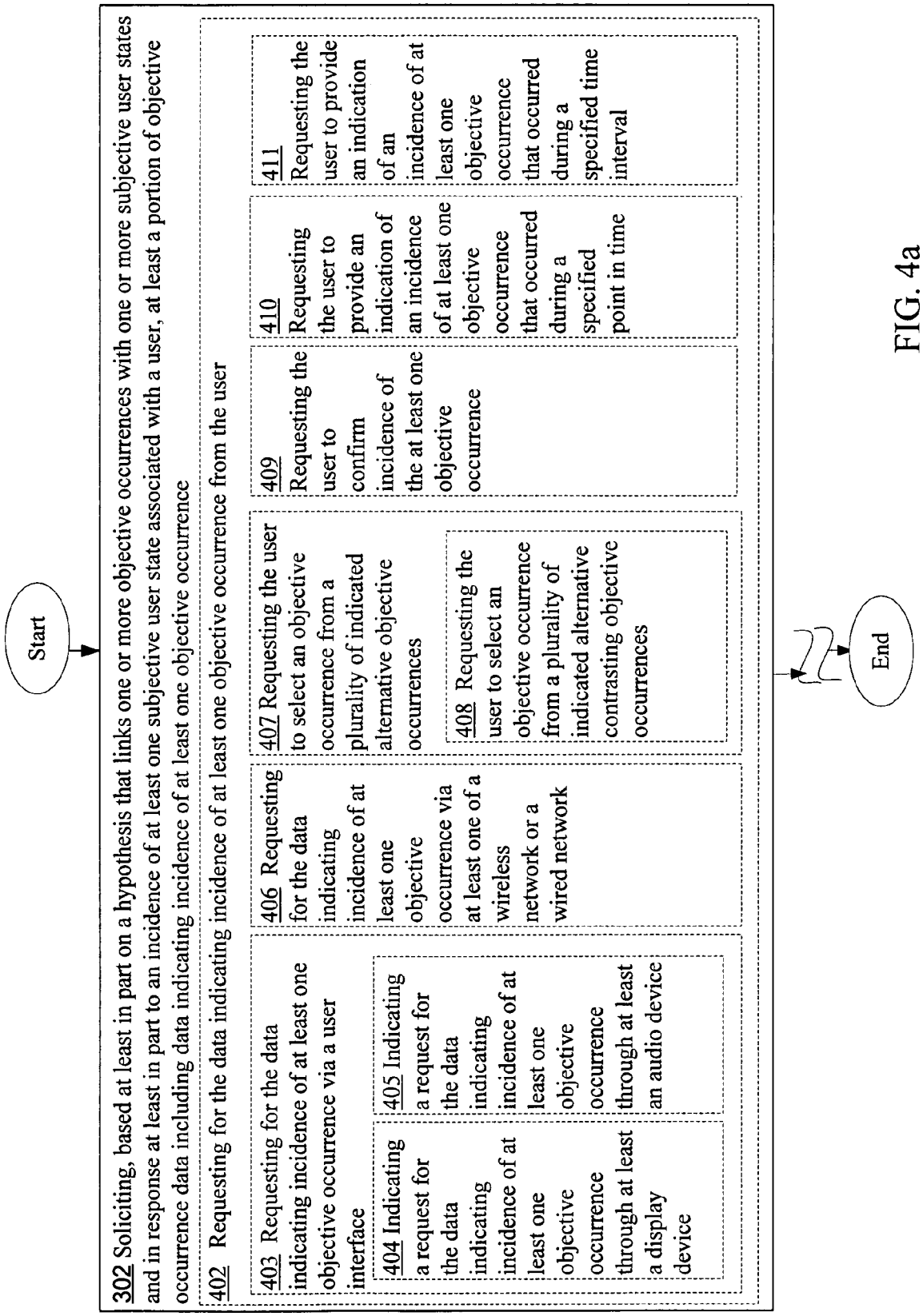
FIG. 4a is a high-level logic flowchart of a process depicting alternate implementations of the objective occurrence data solicitation operation 302 of FIG. 3.

In various implementations, the objective occurrence data solicitation operation 302 of FIG. 3 may include one or more additional operations as illustrated in FIGS. 4a, 4b, 4c, 4d, 4e, 4f, 4g, 4h, 4i, and 4j. For example, in some implementations the objective occurrence data solicitation operation 302 may include a requesting operation 402 for requesting for the data indicating incidence of at least one objective occurrence from the user as depicted in FIG. 4a. For instance, the requesting module 202* of the computing device 10 or the mobile device 30 (e.g., the requesting module 202 of the computing device 10 or the requesting module 202' of the mobile device 30) requesting (e.g., transmitting or indicating a request by the computing device 10 or by the mobile device 30) for the data indicating incidence of at least one objective occurrence 71* (e.g., 71a, 71b, or 71c) from the user 20* (e.g., user 20a or user 20b).

In various implementations, the requesting operation 402 may further include one or more additional operations. For example, in some implementations, the requesting operation 402 may include an operation 403 for requesting for the data indicating incidence of at least one objective occurrence via a user interface as depicted in FIG. 4a. For example, the user interface requesting module 204* of the computing device 10 (e.g., when the computing device 10 is a standalone device) or the mobile device 30 requesting for the data indicating incidence of at least one objective occurrence 71c via a user interface 122* (e.g. an audio device including one or more speakers or a display device such as a display monitor or a touchscreen).

Operation 403, in turn, may further include an operation 404 for indicating a request for the data indicating incidence of at least one objective occurrence through at least a display device as depicted in FIG. 4a. For example, the request indication module 205* of the computing device 10 or the mobile device 30 indicating (e.g., displaying) a request for the data indicating incidence of at least one objective occurrence 71c (e.g., what was consumed for dinner today by the user 20* or whether the user 20* exercised today?) through at least a display device (e.g., a display monitor such as a liquid crystal display or a touchscreen).

In the same or different implementations, operation 403 may include an operation 405 for indicating a request for the data indicating incidence of at least one objective occurrence through at least an audio device as depicted in FIG. 4a. For example, the request indication module 205* of the computing device 10 or the mobile device 30 indicating a request for the data indicating incidence of at least one objective occurrence 70* (e.g., what was the humidity today or was a hot fudge sundae consumed today?) through at least an audio device (e.g., an audio system including one or more speakers).

In some implementations, the requesting operation 402 may include an operation 406 for requesting for the data indicating incidence of at least one objective occurrence via at least one of a wireless network or a wired network as depicted in FIG. 4a. For example, the network interface requesting module 206* of the computing device 10 or the mobile device 30 requesting for the data indicating incidence of at least one objective occurrence 71* (e.g., data indicating blood pressure of the user 20* or data indicating an exercise routine executed by the user 20*) via at least one of a wireless network or a wired network 40. Note that in the case where the computing device 10 is executing operation 406, the data indicating incidence of at least one objective occurrence 71* may be requested from the user 20*, from one or more third party sources 50, from one or more sensors 35, or from other network devices (e.g., network servers). In the case where the mobile device 30 is executing operation 406, the data indicating incidence of at least one objective occurrence 71* may be requested from a user 20a, from one or more third party sources 50, from one or more sensors 35, or from other network devices (e.g., network servers).

In various implementations, the requesting operation 402 may include an operation 407 for requesting the user to select an objective occurrence from a plurality of indicated alternative objective occurrences as depicted in FIG. 4a. For example, the selection request module 214* of the computing device 10 or the mobile device 30 requesting the user 20* to select an objective occurrence from a plurality of indicating alternative objective occurrences (e.g., as indicated via a user interface 122*). For example, requesting a user 20* to select one objective occurrence from a list that includes cloudy weather, sunny weather, high humidity, low humidity, high or low blood pressure, ingestion of a medicine such as aspirin, ingestion of a particular type of food item such as beer, an exercise routine such as jogging, and so forth.

In some implementations, operation 407 may further include an operation 408 for requesting the user to select an objective occurrence from a plurality of indicated alternative contrasting objective occurrences as depicted in FIG. 4a. For example, the selection request module 214* of the computing device 10 or the mobile device 30 requesting the user 20* (e.g., either user 20a or user 20b) to select an objective occurrence from a plurality of indicated alternative contrasting objective occurrences (e.g., as indicated via a user interface 122*). For example, requesting a user 20* to select one objective occurrence from a list of indicated alternative contrasting objective occurrences such as running for 1 hour, running for 30 minutes, running for 15 minutes, walking for 1 hour, walking for 30 minutes, sitting for 1 hour, sitting for 30 minutes, and so forth.

In some implementations, the requesting operation 402 may include an operation 409 for requesting the user to confirm incidence of the at least one objective occurrence as depicted in FIG. 4a. For example, the confirmation request module 216* of the computing device 10 or the mobile device 30 requesting the user 20* to confirm incidence of the at least one objective occurrence (e.g., did user 20* have a salad for lunch today?).

In some implementations, the requesting operation 402 may include an operation 410 for requesting the user to provide an indication of an incidence of at least one objective occurrence that occurred during a specified point in time as depicted in FIG. 4a. For example, the requesting module 202* of the computing device 10 or the mobile device 30 requesting the user 20* (e.g., either user 20a or user 20b) to provide an indication of an incidence of at least one objective occurrence that occurred during a specified point in time (e.g., asking the user 20* whether the user 20* ate dinner at a particular Mexican restaurant at 8 PM?).

In some implementations, the requesting operation 402 may include an operation 411 for requesting the user to provide an indication of an incidence of at least one objective occurrence that occurred during a specified time interval as depicted in FIG. 4a. For example, the requesting module 202* of the computing device 10 or the mobile device 30 requesting the user 20* to provide an indication of an incidence of at least one objective occurrence that occurred during a specified time interval (e.g., asking the user 20* whether the user 20* slept between 11 PM to 7 AM?).

Figure 4B:
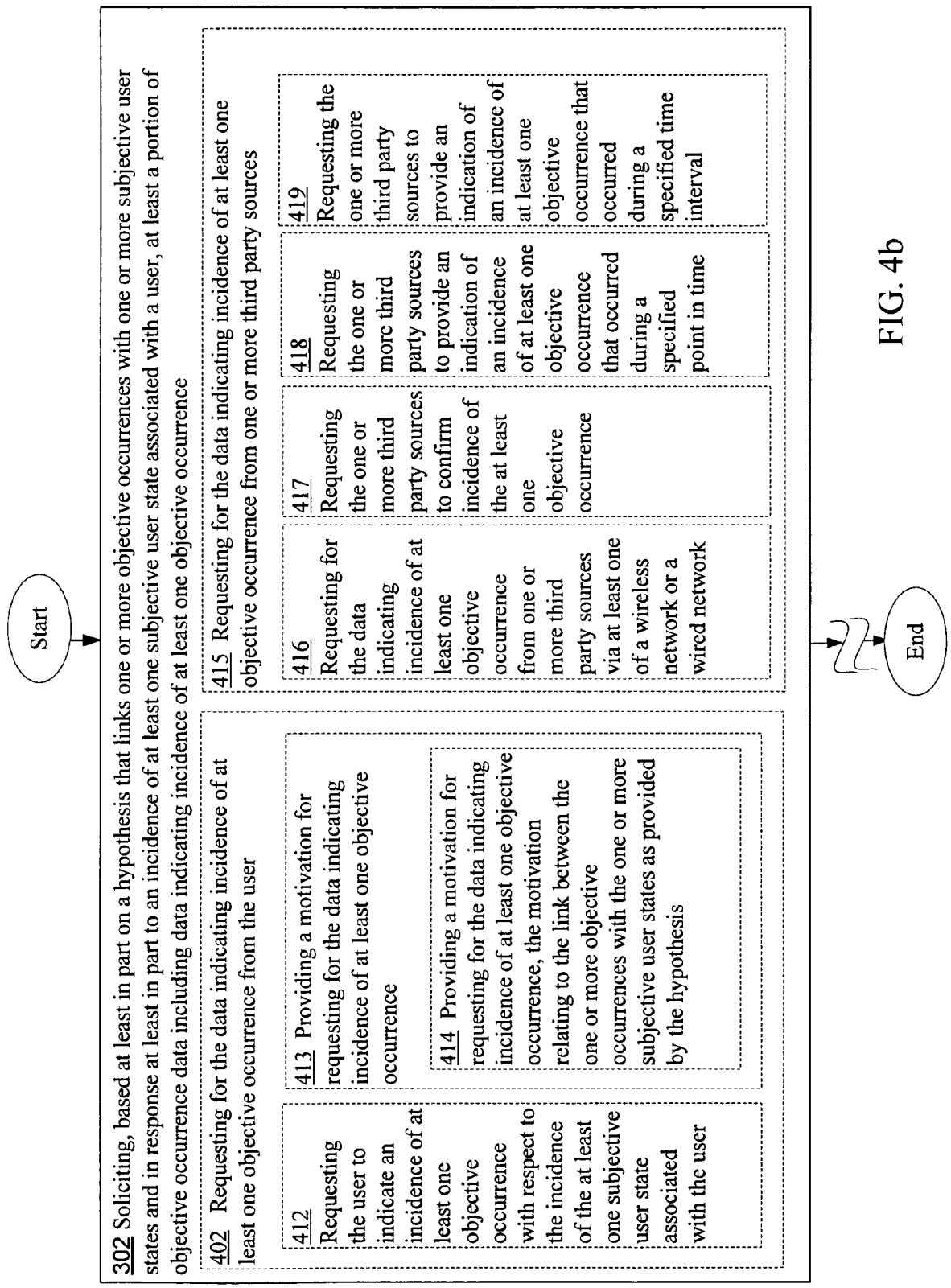
FIG. 4b is a high-level logic flowchart of a process depicting alternate implementations of the objective occurrence data solicitation operation 302 of FIG. 3.

In some implementations, the requesting operation 402 may include an operation 412 for requesting the user to indicate an incidence of at least one objective occurrence with respect to the incidence of the at least one subjective user state associated with the user as depicted in FIG. 4b. For instance, the requesting module 202* of the computing device 10 or the mobile device 30 requesting the user 20* (e.g., either user 20a or user 20b) to indicate an incidence of at least one objective occurrence with respect to the incidence of the at least one subjective user state associated with the user 20*. For example, asking the user 20* to indicate what the weather was like when the user 20* felt depressed.

In various implementations, the requesting operation 402 may include an operation 413 for providing a motivation for requesting for the data indicating incidence of at least one objective occurrence as depicted in FIG. 4b. For instance, the motivation provision module 212* of the computing device 10 or the mobile device 30 providing a motivation for requesting for the data indicating incidence of at least one objective occurrence 71c (e.g., last time the user 20* was depressed, the weather was very bad).

In some implementations, operation 413 may include an operation 414 for providing a motivation for requesting for the data indicating incidence of at least one objective occurrence, the motivation relating to the link between the one or more objective occurrences with the one or more subjective user states as provided by the hypothesis as depicted in FIG. 4b. For instance, the motivation provision module 212* of the computing device 10 or the mobile device 30 providing a motivation for requesting for the data indicating incidence of at least one objective occurrence 71c, the motivation relating to the link between the one or more objective occurrences with the one or more subjective user states as provided by the hypothesis 77 (e.g., hypothesis linking depression with bad weather).

In various implementations, the solicitation operation 302 of FIG. 3 may include a requesting operation 415 for requesting for the data indicating incidence of at least one objective occurrence from one or more third party sources as depicted in FIG. 4b. For instance, the requesting module 202* of the computing device 10 or the mobile device 30 requesting (e.g., via at least one of a wireless network or a wired network 40) for the data indicating incidence of at least one objective occurrence 71a from one or more third party sources 50.

In various implementations, the requesting operation 415 may include one or more additional operations. For example, in some implementations, the requesting operation 415 may include an operation 416 for requesting for the data indicating incidence of at least one objective occurrence from one or more third party sources via at least one of a wireless network or a wired network as depicted in FIG. 4b. For instance, the network interface requesting module 206* of the computing device 10 or the mobile device 30 requesting for the data indicating incidence of at least one objective occurrence 71a from one or more third party sources 50 via at least one of a wireless network or a wired network 40.

In some implementations, the requesting operation 415 may include an operation 417 for requesting the one or more third party sources to confirm incidence of the at least one objective occurrence as depicted in FIG. 4b. For instance, the confirmation request module 216* of the computing device 10 or the mobile device 30 requesting the one or more third party sources 50* to confirm incidence of the at least one objective occurrence (e.g., asking a fitness center or a network device associated with the fitness center whether the user 20* exercised on the treadmill for 30 minutes on Tuesday).

In some implementations, the requesting operation 415 may include an operation 418 for requesting the one or more third party sources to provide an indication of an incidence of at least one objective occurrence that occurred during a specified point in time as depicted in FIG. 4b. For instance, the requesting module 202* of the computing device 10 or the mobile device 30 requesting the one or more third party sources 50 to provide an indication of an incidence of at least one objective occurrence that occurred during a specified point in time. For example, requesting from a content provider an indication of the local weather for 10 AM Tuesday).

In some implementations, the requesting operation 415 may include an operation 419 for requesting the one or more third party sources to provide an indication of an incidence of at least one objective occurrence that occurred during a specified time interval as depicted in FIG. 4b. For instance, the requesting module 202* of the computing device 10 or the mobile device 30 requesting the one or more third party sources 50 to provide an indication of an incidence of at least one objective occurrence that occurred during a specified time interval. For example, requesting from a content provider for an indication of the performance of the stock market between 9 AM and 1 PM on Tuesday.

Figure 4C:
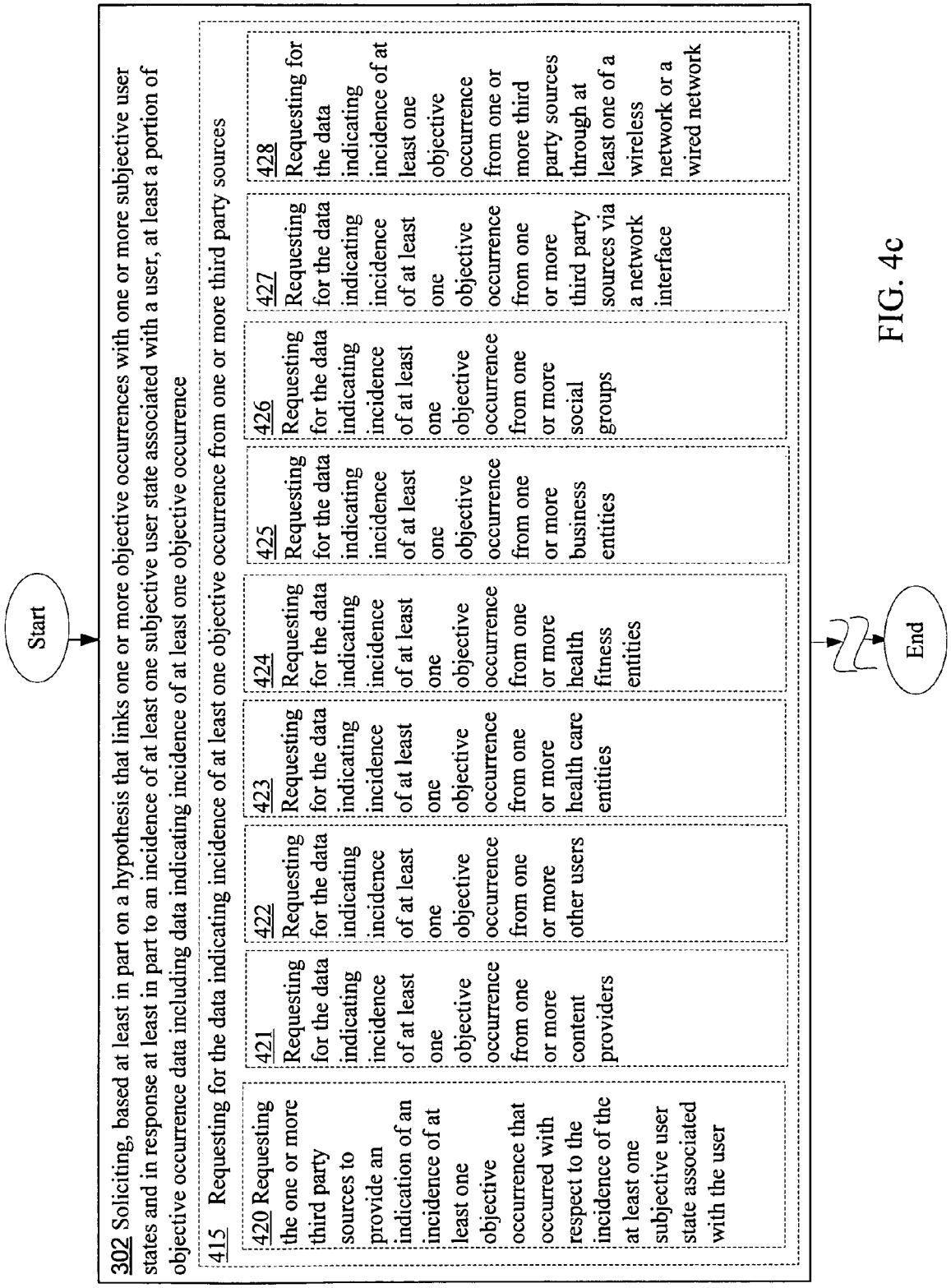
FIG. 4c is a high-level logic flowchart of a process depicting alternate implementations of the objective occurrence data solicitation operation 302 of FIG. 3.

In some implementations, the requesting operation 415 may include an operation 420 for requesting the one or more third party sources to provide an indication of an incidence of at least one objective occurrence that occurred with respect to the incidence of the at least one subjective user state associated with the user as depicted in FIG. 4c. For instance, the requesting module 202* of the computing device 10 or the mobile device 30 requesting the one or more third party sources 50 (e.g., spouse of user 20*) to provide an indication of an incidence of at least one objective occurrence (e.g., excessive snoring while sleeping) that occurred with respect to the incidence of the at least one subjective user state (e.g., sleepiness or fatigue) associated with the user 20*.

In some implementations, the requesting operation 415 may include an operation 421 for requesting for the data indicating incidence of at least one objective occurrence from one or more content providers as depicted in FIG. 4c. For instance, the requesting module 202* of the computing device 10 or the mobile device 30 requesting for the data indicating incidence of at least one objective occurrence 71a from one or more content providers (e.g., weather channel, internet news service, and so forth).

In some implementations, the requesting operation 415 may include an operation 422 for requesting for the data indicating incidence of at least one objective occurrence from one or more other users as depicted in FIG. 4c. For instance, the requesting module 202* of the computing device 10 or the mobile device 30 requesting for the data indicating incidence of at least one objective occurrence 71a from one or more other users (e.g., spouse, relatives, friends, or co-workers of user 20*).

In some implementations, the requesting operation 415 may include an operation 423 for requesting for the data indicating incidence of at least one objective occurrence from one or more health care entities as depicted in FIG. 4c. For instance, the requesting module 202* of the computing device 10 or the mobile device 30 requesting for the data indicating incidence of at least one objective occurrence 71a from one or more health care entities (e.g., medical doctors, dentists, health care facilities, clinics, hospitals, and so forth).

In some implementations, the requesting operation 415 may include an operation 424 for requesting for the data indicating incidence of at least one objective occurrence from one or more health fitness entities as depicted in FIG. 4c. For instance, the requesting module 202* of the computing device 10 or the mobile device 30 requesting for the data indicating incidence of at least one objective occurrence 71a from one or more health fitness entities (e.g., fitness gyms or fitness instructors).

In some implementations, the requesting operation 415 may include an operation 425 for requesting for the data indicating incidence of at least one objective occurrence from one or more business entities as depicted in FIG. 4c. For instance, the requesting module 202* of the computing device 10 or the mobile device 30 requesting for the data indicating incidence of at least one objective occurrence 71a from one or more business entities (e.g., user 20* place of employment, merchandiser, airlines, and so forth).

In some implementations, the requesting operation 415 may include an operation 426 for requesting for the data indicating incidence of at least one objective occurrence from one or more social groups as depicted in FIG. 4c. For instance, the requesting module 202* of the computing device 10 or the mobile device 30 requesting for the data indicating incidence of at least one objective occurrence 71a from one or more social groups (e.g., PTA, social networking groups, societies, clubs, and so forth).

In some implementations, the requesting operation 415 may include an operation 427 for requesting for the data indicating incidence of at least one objective occurrence from one or more third party sources via a network interface as depicted in FIG. 4c. For instance, the requesting module 202* of the computing device 10 or the mobile device 30 requesting for the data indicating incidence of at least one objective occurrence 71a from one or more third party sources 50 via a network interface 120*.

In some implementations, the requesting operation 415 may include an operation 428 for requesting for the data indicating incidence of at least one objective occurrence from one or more third party sources through at least one of a wireless network or a wired network as depicted in FIG. 4c. For instance, the requesting module 202* of the computing device 10 or the mobile device 30 requesting for the data indicating incidence of at least one objective occurrence 71a from one or more third party sources 50 through at least one of a wireless network or a wired network 40.

Figure 4D:
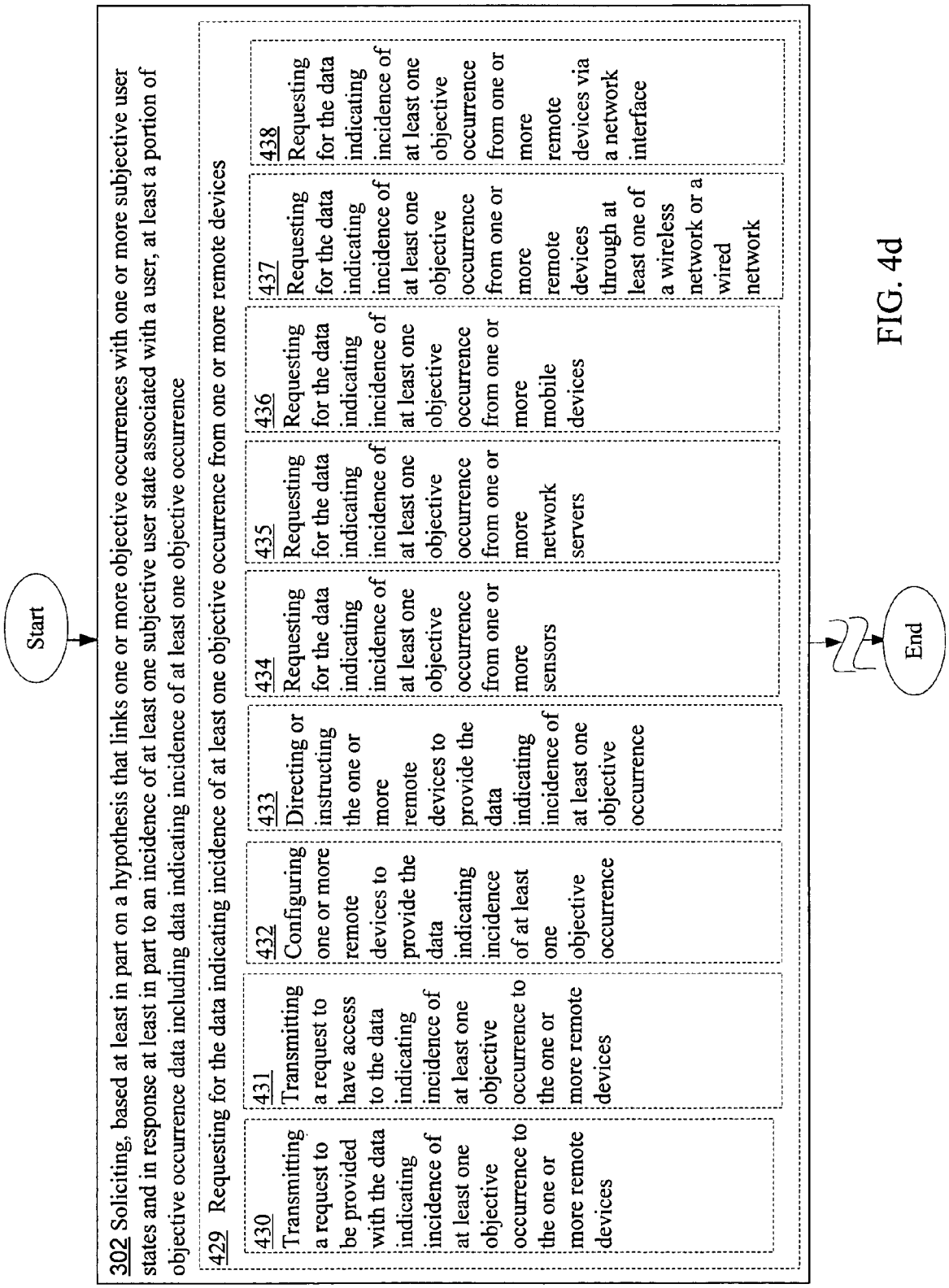
FIG. 4d is a high-level logic flowchart of a process depicting alternate implementations of the objective occurrence data solicitation operation 302 of FIG. 3.

In various implementations, the solicitation operation 302 of FIG. 3 may include an operation 429 for requesting for the data indicating incidence of at least one objective occurrence from one or more remote devices as depicted in FIG. 4d. For instance, the network interface requesting module 206* of the computing device 10 or the mobile device 30 requesting for the data indicating incidence of at least one objective occurrence 71b from one or more remote devices (e.g., network servers, sensors 35, mobile devices including mobile device 30, and/or other network devices).

Operation 429, in turn, may include one or more additional operations in various alternative implementations. For example, in some implementations, operation 429 may include an operation 430 for transmitting a request to be provided with the data indicating incidence of at least one objective occurrence to the one or more remote devices as depicted in FIG. 4d. For instance, the request transmission module 207* of the computing device 10 or the mobile device 30 transmitting a request to be provided with the data indicating incidence of at least one objective occurrence 71b to one or more remote devices (e.g., network servers, sensors 35, mobile devices including mobile device 30, and/or other network devices).

In some implementations, operation 429 may include an operation 431 for transmitting a request to have access to the data indicating incidence of at least one objective occurrence to the one or more remote devices as depicted in FIG. 4d. For instance, the request access module 208* of the computing device 10 or the mobile device 30 transmitting a request to have access to the data indicating incidence of at least one objective occurrence 71b to the one or more remote devices (e.g., network servers, sensors 35, mobile devices including mobile device 30 in the case where operation 431 is performed by the computing device 10 and the computing device 10 is a server, and/or other network devices).

In some implementations, operation 429 may include an operation 432 for configuring one or more remote devices to provide the data indicating incidence of at least one objective occurrence as depicted in FIG. 4d. For instance, the configuration module 209* of the computing device 10 or the mobile device 30 configuring, via at least one of a wireless network or wired network 40, one or more remote devices (e.g., network servers, mobile devices including mobile device 30, sensors 35, or other network devices) to provide the data indicating incidence of at least one objective occurrence 71b.

In some implementations, operation 429 may include an operation 433 for directing or instructing the one or more remote devices to provide the data indicating incidence of at least one objective occurrence as depicted in FIG. 4d. For instance, the directing/instructing module 210* of the computing device 10 or the mobile device 30 directing or instructing, via at least one of a wireless network or wired network 40, the one or more remote devices (e.g., network servers, mobile devices including mobile device 35, sensors 35, or other network devices) to provide the data indicating incidence of at least one objective occurrence 71b.

In some implementations, operation 429 may include an operation 434 for requesting for the data indicating incidence of at least one objective occurrence from one or more sensors as depicted in FIG. 4d. For instance, the network interface requesting module 206* of the computing device 10 or the mobile device 30 requesting for the data indicating incidence of at least one objective occurrence 71b from one or more sensors 35 (e.g., GPS, physiological measuring device such as a blood pressure device or glucometer).

In some implementations, operation 429 may include an operation 435 for requesting for the data indicating incidence of at least one objective occurrence from one or more network servers as depicted in FIG. 4d. For instance, the network interface requesting module 206* of the computing device 10 or the mobile device 30 requesting for the data indicating incidence of at least one objective occurrence 71b from one or more network servers, which may have previously obtained such data.

In some implementations, operation 429 may include an operation 436 for requesting for the data indicating incidence of at least one objective occurrence from one or more mobile devices as depicted in FIG. 4d. For instance, the network interface requesting module 206* of the computing device 10 or the mobile device 30 requesting for the data indicating incidence of at least one objective occurrence 71b from one or more mobile devices (e.g., cellular telephone, PDA, laptop or notebook, and so forth) including, for example, mobile device 30.

In some implementations, operation 429 may include an operation 437 for requesting for the data indicating incidence of at least one objective occurrence from one or more remote devices through at least one of a wireless network or a wired network as depicted in FIG. 4d. For instance, the network interface requesting module 206* of the computing device 10 or the mobile device 30 requesting for the data indicating incidence of at least one objective occurrence 71b from one or more remote network devices through at least one of a wireless network or a wired network 40.

In some implementations, operation 429 may include an operation 438 for requesting for the data indicating incidence of at least one objective occurrence from one or more remote devices via a network interface as depicted in FIG. 4d. For instance, the network interface requesting module 206* of the computing device 10 or the mobile device 30 requesting for the data indicating incidence of at least one objective occurrence 71b from one or more remote network devices via a network interface 120*.

Figure 4E:
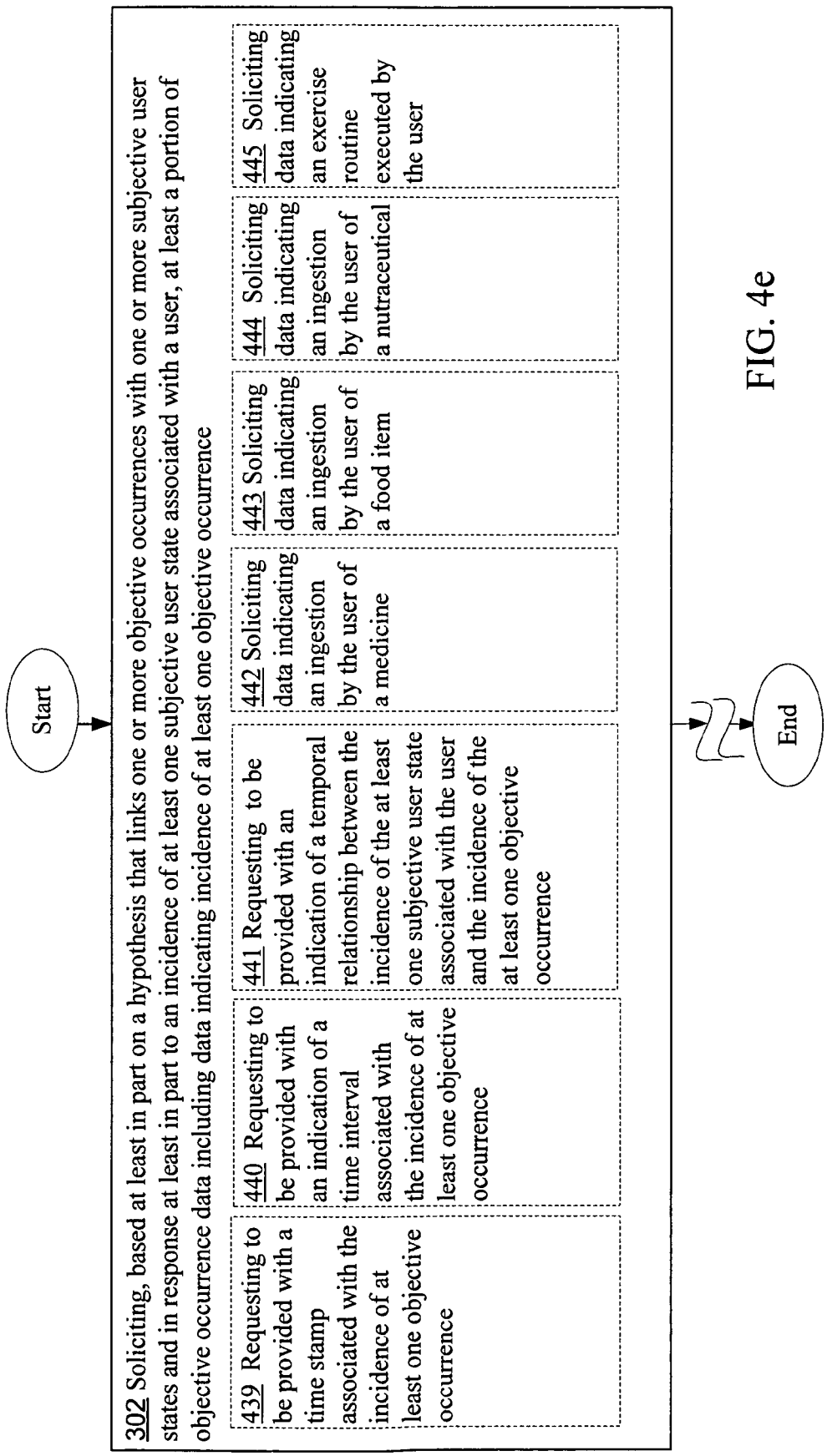
FIG. 4e is a high-level logic flowchart of a process depicting alternate implementations of the objective occurrence data solicitation operation 302 of FIG. 3.

In various implementations, the solicitation operation 302 of FIG. 3 may include an operation 439 for requesting to be provided with a time stamp associated with the incidence of at least one objective occurrence as depicted in FIG. 4e. For instance, the time/temporal element request module 218* of the computing device 10 or the mobile device 30 requesting to be provided with a time stamp associated with the incidence of at least one objective occurrence (e.g., requesting a time stamp associated with the user 20* consuming a particular medication).

In some implementations, the solicitation operation 302 may include an operation 440 for requesting to be provided with an indication of a time interval associated with the incidence of at least one objective occurrence as depicted in FIG. 4e. For instance, the time/temporal element request module 218* of the computing device 10 or the mobile device 30 requesting to be provided with an indication of a time interval associated with the incidence of at least one objective occurrence (e.g., requesting to be provided with an indication that indicates the time interval in which the user 20* exercised on the treadmill).

In some implementations, the solicitation operation 302 may include an operation 441 for requesting to be provided with an indication of a temporal relationship between the incidence of the at least one subjective user state associated with the user and the incidence of the at least one objective occurrence as depicted in FIG. 4e. For instance, the time/temporal element request module 218* of the computing device 10 or the mobile device 30 requesting to be provided with an indication of a temporal relationship between the incidence of the at least one subjective user state associated with the user 20* and the incidence of the at least one objective occurrence (e.g., did user 20* eat at the Mexican restaurant before, after, or as the user 20* was having the upset stomach?).

In some implementations, the solicitation operation 302 may include an operation 442 for soliciting data indicating an ingestion by the user of a medicine as depicted in FIG. 4e. For instance, the objective occurrence data solicitation module 101* of the computing device 10 or the mobile device 30 soliciting (e.g., via a network interface 120* or via a user interface 122*) data indicating an ingestion by the user 20* of a medicine (e.g., what type of medicine was ingested on Wednesday morning?).

In some implementations, the solicitation operation 302 may include an operation 443 for soliciting data indicating an ingestion by the user of a food item as depicted in FIG. 4e. For instance, the objective occurrence data solicitation module 101* of the computing device 10 or the mobile device 30 soliciting (e.g., via a network interface 120* or via a user interface 122*) data indicating an ingestion by the user 20* of a food item (e.g., what did the user 20* eat for lunch?).

In some implementations, the solicitation operation 302 may include an operation 444 for soliciting data indicating an ingestion by the user of a nutraceutical as depicted in FIG. 4e. For instance, the objective occurrence data solicitation module 101* of the computing device 10 or the mobile device 30 soliciting (e.g., via a network interface 120* or via a user interface 122*) data indicating an ingestion by the user 20* of a nutraceutical (e.g., what type of nutraceutical did the user 20* eat on Tuesday?).

In some implementations, the solicitation operation 302 may include an operation 445 for soliciting data indicating an exercise routine executed by the user as depicted in FIG. 4e. For instance, the objective occurrence data solicitation module 101* of the computing device 10 or the mobile device 30 soliciting (e.g., via a network interface 120* or via a user interface 122*) data indicating an exercise routine executed by the user 20* (e.g., what type of exercise did the user 20* do today?).

Figure 4F:
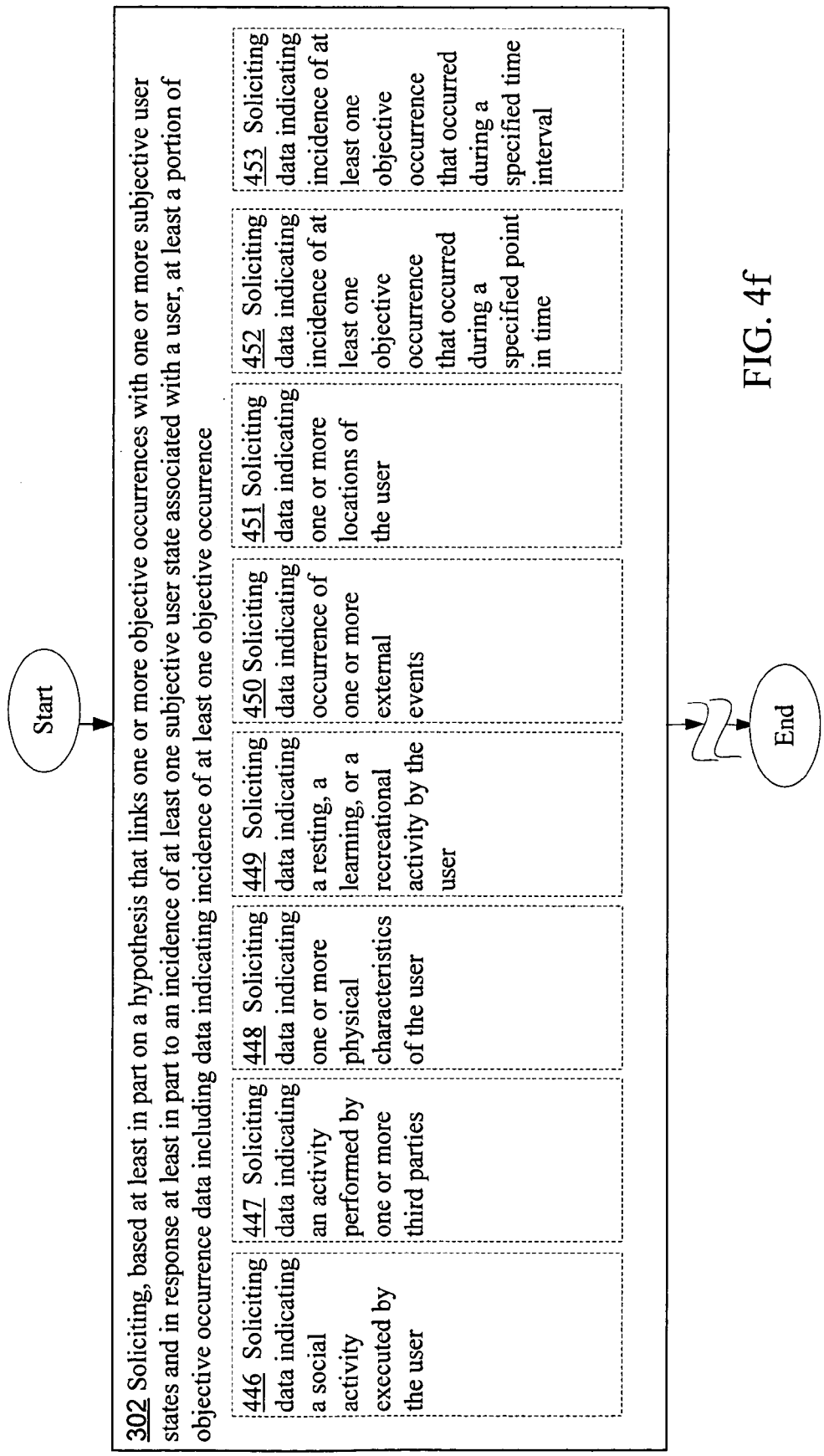
FIG. 4f is a high-level logic flowchart of a process depicting alternate implementations of the objective occurrence data solicitation operation 302 of FIG. 3.

In some implementations, the solicitation operation 302 may include an operation 446 for soliciting data indicating a social activity executed by the user as depicted in FIG. 4f. For instance, the objective occurrence data solicitation module 101* of the computing device 10 or the mobile device 30 soliciting (e.g., via a network interface 120* or via a user interface 122*) data indicating a social activity executed by the user 20*. For example, asking the user 20* or a third party (e.g., another user) whether the user 20* went with friends to a nightclub.

In some implementations, the solicitation operation 302 may include an operation 447 for soliciting data indicating an activity performed by one or more third parties as depicted in FIG. 4f. For instance, the objective occurrence data solicitation module 101* of the computing device 10 or the mobile device 30 soliciting (e.g., via a network interface 120* or via a user interface 122*) data indicating an activity performed by one or more third parties (e.g., boss going on vacation). For example, asking the user 20* or a third party (e.g., another user) whether the user 20* went on a vacation.

In some implementations, the solicitation operation 302 may include an operation 448 for soliciting data indicating one or more physical characteristics of the user as depicted in FIG. 4f. For instance, the objective occurrence data solicitation module 101* of the computing device 10 or the mobile device 30 soliciting (e.g., via a network interface 120* or via a user interface 122*) data indicating one or more physical characteristics (e.g., blood pressure) of the user 20*. For example, requesting the user 20*, a third party source 50 (e.g., a physician), or a sensor 35 to provide data indicating blood pressure of the user 20*.

In some implementations, the solicitation operation 302 may include an operation 449 for soliciting data indicating a resting, a learning, or a recreational activity by the user as depicted in FIG. 4f. For instance, the objective occurrence data solicitation module 101* of the computing device 10 or the mobile device 30 soliciting (e.g., via a network interface 120* or via a user interface 122*) data indicating a resting (e.g., sleeping), a learning (e.g., attending a class or reading a book), or a recreational activity (e.g., playing golf or fishing) by the user 20*.

In some implementations, the solicitation operation 302 may include an operation 450 for soliciting data indicating occurrence of one or more external events as depicted in FIG. 4f. For instance, the objective occurrence data solicitation module 101* of the computing device 10 or the mobile device 30 soliciting (e.g., via a network interface 120* or via a user interface 122*) data indicating occurrence of one or more external events (e.g., poor weather or poor stock market performance). For example requesting the user 20* or one or more third party sources 50 such as content providers to provide indications of the local weather or performance of the stock market.

In some implementations, the solicitation operation 302 may include an operation 451 for soliciting data indicating one or more locations of the user as depicted in FIG. 4f. For instance, the objective occurrence data solicitation module 101* of the computing device 10 or the mobile device 30 soliciting (e.g., via a network interface 120* or via a user interface 122*) data indicating one or more locations of the user 20*. For example requesting the user 20* or a sensor 35 such as a GPS to provide one or more locations of the user 20*.

In some implementations, the solicitation operation 302 may include an operation 452 for soliciting data indicating incidence of at least one objective occurrence that occurred during a specified point in time as depicted in FIG. 4f. For instance, the objective occurrence data solicitation module 101* of the computing device 10 or the mobile device 30 soliciting (e.g., via a network interface 120* or via a user interface 122*) data indicating incidence of at least one objective occurrence that occurred during a specified point in time (e.g., asking what the user 20* ate at noon).

In some implementations, the solicitation operation 302 may include an operation 453 for soliciting data indicating incidence of at least one objective occurrence that occurred during a specified time interval as depicted in FIG. 4f. For instance, the objective occurrence data solicitation module 101* of the computing device 10 or the mobile device 30 soliciting (e.g., via a network interface 120* or via a user interface 122*) data indicating incidence of at least one objective occurrence 71* that occurred during a specified time interval (e.g., asking whether the user 20* consumed any medication between 8 PM and midnight).

Figure 4G:
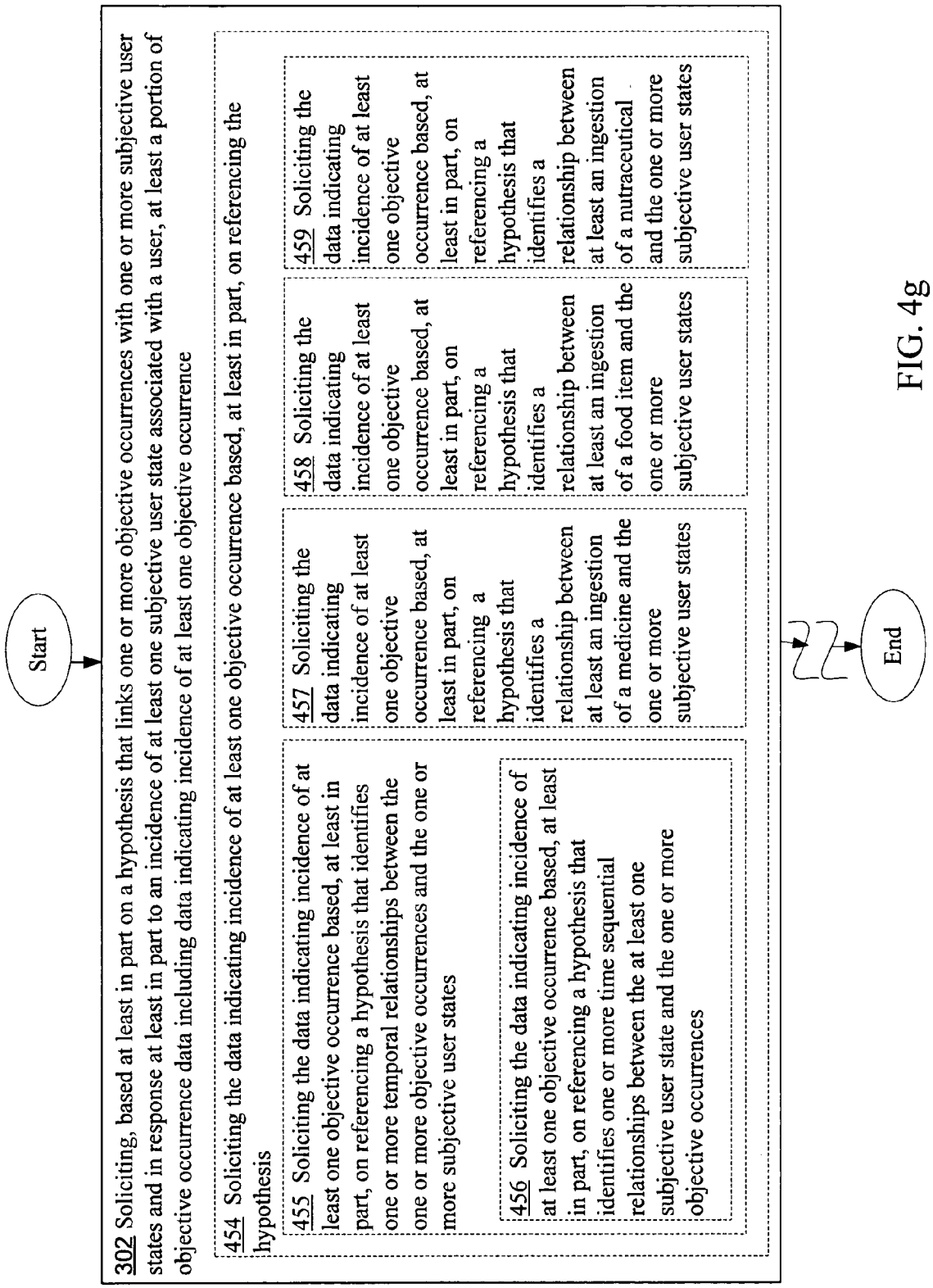
FIG. 4g is a high-level logic flowchart of a process depicting alternate implementations of the objective occurrence data solicitation operation 302 of FIG. 3.

In various implementations, the solicitation operation 302 of FIG. 3 may include operations that may be particularly performed by the computing device 10. For example, in some implementations, the solicitation operation 302 may include an operation 454 for soliciting the data indicating incidence of at least one objective occurrence based, at least in part, on referencing the hypothesis as depicted in FIG. 4g. For instance, the objective occurrence data solicitation module 101 of the computing device 10 soliciting the data indicating incidence of at least one objective occurrence 71* based, at least in part, on the hypothesis referencing module 220 referencing the hypothesis 77.

Operation 454, in various implementations, may further include one or more additional operations. For example, in some implementations, operation 454 may include an operation 455 for soliciting the data indicating incidence of at least one objective occurrence based, at least in part, on referencing a hypothesis that identifies one or more temporal relationships between the one or more objective occurrences and the one or more subjective user states as depicted in FIG. 4g. For instance, the objective occurrence data solicitation module 101 of the computing device 10 soliciting the data indicating incidence of at least one objective occurrence 71* based, at least in part, on the hypothesis referencing module 220 referencing a hypothesis 77 that identifies one or more temporal relationships between the one or more objective occurrences and the one or more subjective user states. For example, the hypothesis 77 may indicate that a person may feel more alert after exercising vigorously for one hour.

In some cases, operation 455 may further include an operation 456 for soliciting the data indicating incidence of at least one objective occurrence based, at least in part, on referencing a hypothesis that identifies one or more time sequential relationships between the at least one subjective user state and the one or more objective occurrences as depicted in FIG. 4g. For instance, the objective occurrence data solicitation module 101 of the computing device 10 soliciting the data indicating incidence of at least one objective occurrence 71* based, at least in part, on the hypothesis referencing module 220 referencing a hypothesis 77 that identifies one or more time sequential relationships between the at least one subjective user state and the one or more objective occurrences. For example, the hypothesis 77 may indicate that a person may develop a stomach ache two hours after eating a hot fudge sundae.

In some implementations, operation 454 may include an operation 457 for soliciting the data indicating incidence of at least one objective occurrence based, at least in part, on referencing a hypothesis that identifies a relationship between at least an ingestion of a medicine and the one or more subjective user states as depicted in FIG. 4g. For instance, the objective occurrence data solicitation module 101 of the computing device 10 soliciting the data indicating incidence of at least one objective occurrence 71* based, at least in part, on the hypothesis referencing module 220 referencing a hypothesis 77 that identifies a relationship between at least an ingestion of a medicine (e.g., aspirin) and the one or more subjective user states (e.g., pain relief).

In some implementations, operation 454 may include an operation 458 for soliciting the data indicating incidence of at least one objective occurrence based, at least in part, on referencing a hypothesis that identifies a relationship between at least an ingestion of a food item and the one or more subjective user states as depicted in FIG. 4g. For instance, the objective occurrence data solicitation module 101 of the computing device 10 soliciting the data indicating incidence of at least one objective occurrence 71* based, at least in part, on the hypothesis referencing module 220 referencing a hypothesis 77 that identifies a relationship between at least an ingestion of a food item (e.g., papaya) and the one or more subjective user states (e.g., bowel movement).

In some implementations, operation 454 may include an operation 459 for soliciting the data indicating incidence of at least one objective occurrence based, at least in part, on referencing a hypothesis that identifies a relationship between at least an ingestion of a nutraceutical and the one or more subjective user states as depicted in FIG. 4g. For instance, the objective occurrence data solicitation module 101 of the computing device 10 soliciting the data indicating incidence of at least one objective occurrence 71* based, at least in part, on the hypothesis referencing module 220 referencing a hypothesis 77 that identifies a relationship between at least an ingestion of a nutraceutical and the one or more subjective user states.

Figure 4H:
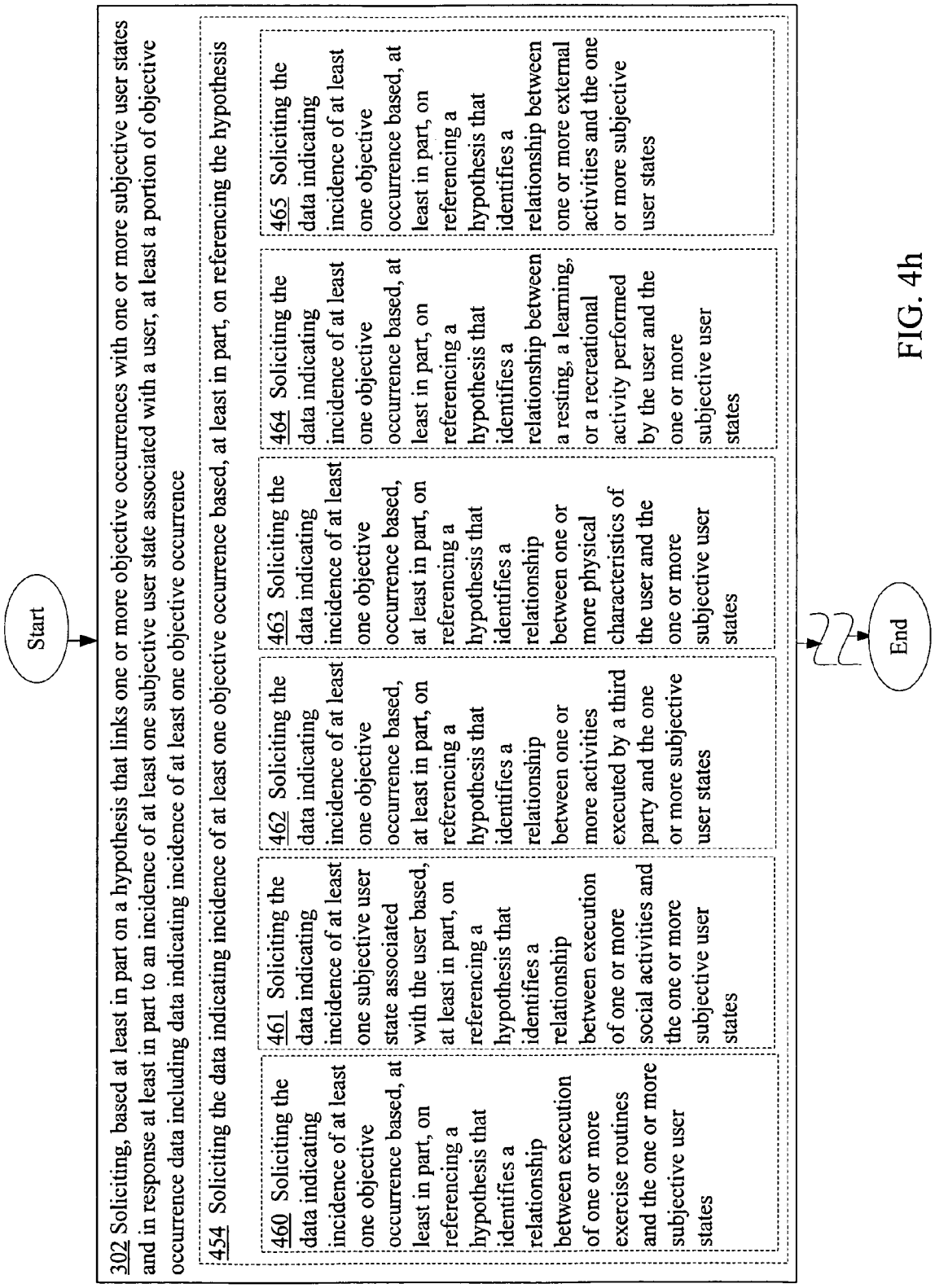
FIG. 4h is a high-level logic flowchart of a process depicting alternate implementations of the objective occurrence data solicitation operation 302 of FIG. 3.

In some implementations, operation 454 may include an operation 460 for soliciting the data indicating incidence of at least one objective occurrence based, at least in part, on referencing a hypothesis that identifies a relationship between execution of one or more exercise routines and the one or more subjective user states as depicted in FIG. 4h. For instance, the objective occurrence data solicitation module 101 of the computing device 10 soliciting the data indicating incidence of at least one objective occurrence 71* based, at least in part, on the hypothesis referencing module 220 referencing a hypothesis 77 that identifies a relationship between execution of one or more exercise routines (e.g., playing basketball) and the one or more subjective user states (e.g., painful ankles).

In some implementations, operation 454 may include an operation 461 for soliciting the data indicating incidence of at least one subjective user state associated with the user based, at least in part, on referencing a hypothesis that identifies a relationship between execution of one or more social activities and the one or more subjective user states as depicted in FIG. 4h. For instance, the objective occurrence data solicitation module 101 of the computing device 10 soliciting the data indicating incidence of at least one objective occurrence 71* based, at least in part, on the hypothesis referencing module 220 referencing a hypothesis 77 that identifies a relationship between execution of one or more social activities (e.g., playing with offspring) and the one or more subjective user states (e.g., happiness).

In some implementations, operation 454 may include an operation 462 for soliciting the data indicating incidence of at least one objective occurrence based, at least in part, on referencing a hypothesis that identifies a relationship between one or more activities executed by a third party and the one or more subjective user states as depicted in FIG. 4h. For instance, the objective occurrence data solicitation module 101 of the computing device 10 soliciting the data indicating incidence of at least one objective occurrence 71* based, at least in part, on the hypothesis referencing module 220 referencing a hypothesis 77 that identifies a relationship between one or more activities executed by a third party (in-laws visiting) and the one or more subjective user states (e.g., tension).

In some implementations, operation 454 may include an operation 463 for soliciting the data indicating incidence of at least one objective occurrence based, at least in part, on referencing a hypothesis that identifies a relationship between one or more physical characteristics of the user and the one or more subjective user states as depicted in FIG. 4h. For instance, the objective occurrence data solicitation module 101 of the computing device 10 soliciting the data indicating incidence of at least one objective occurrence 71* based, at least in part, on the hypothesis referencing module 220 referencing a hypothesis 77 that identifies a relationship between one or more physical characteristics (e.g., low blood sugar level) of the user 20* and the one or more subjective user states (e.g., lack of alertness).

In some implementations, operation 454 may include an operation 464 for soliciting the data indicating incidence of at least one objective occurrence based, at least in part, on referencing a hypothesis that identifies a relationship between a resting, a learning, or a recreational activity performed by the user and the one or more subjective user states as depicted in FIG. 4h. For instance, the objective occurrence data solicitation module 101 of the computing device 10 soliciting the data indicating incidence of at least one objective occurrence 71* based, at least in part, on the hypothesis referencing module 220 referencing a hypothesis 77 that identifies a relationship between a resting, a learning, or a recreational activity performed by the user 20* and the one or more subjective user states.

In some implementations, operation 454 may include an operation 465 for soliciting the data indicating incidence of at least one objective occurrence based, at least in part, on referencing a hypothesis that identifies a relationship between one or more external activities and the one or more subjective user states as depicted in FIG. 4h. For instance, the objective occurrence data solicitation module 101 of the computing device 10 soliciting the data indicating incidence of at least one objective occurrence 71* based, at least in part, on the hypothesis referencing module 220 referencing a hypothesis 77 that identifies a relationship between one or more external activities (e.g., poor performance of a sports team) and the one or more subjective user states (e.g., depression).

Figure 4I:
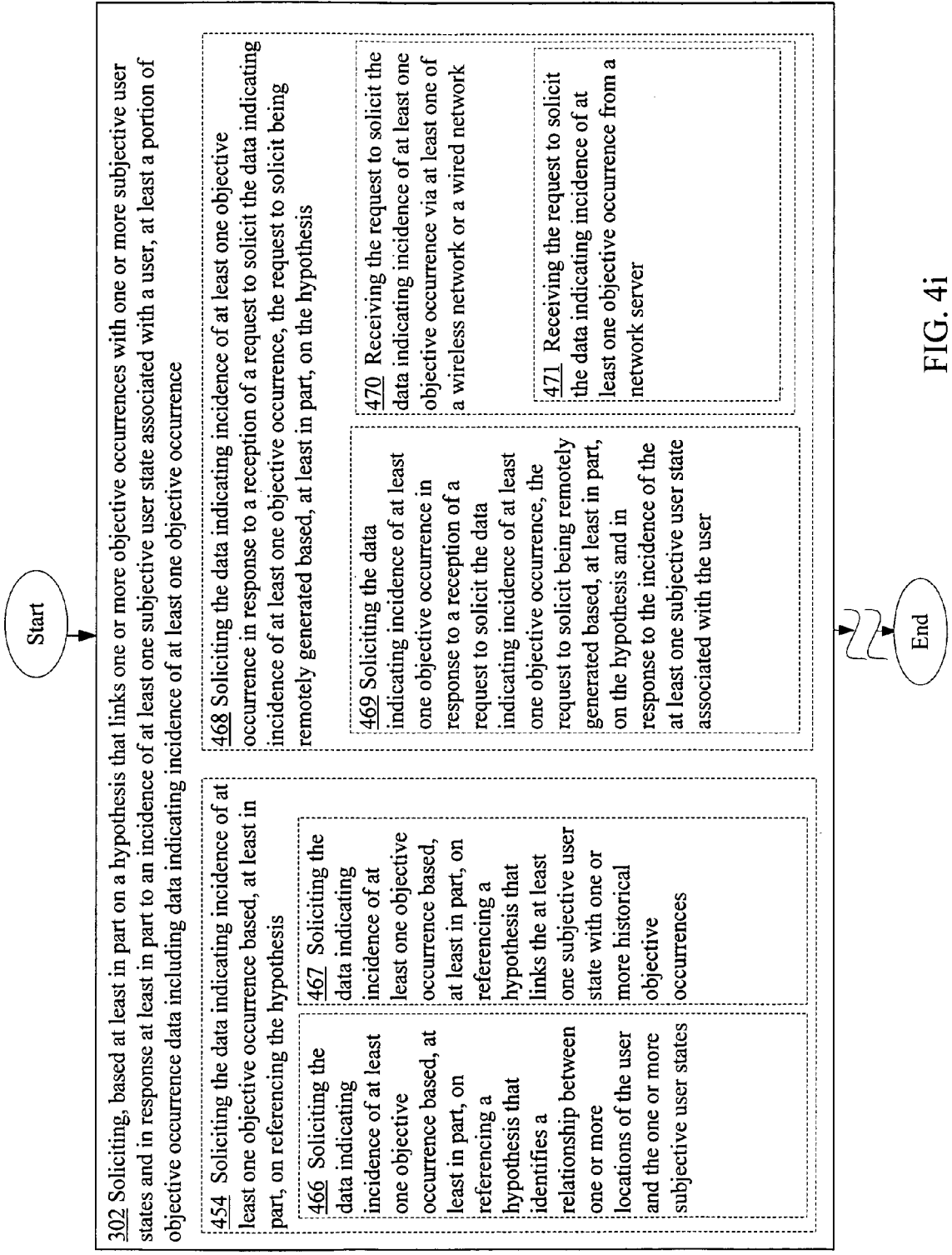
FIG. 4i is a high-level logic flowchart of a process depicting alternate implementations of the objective occurrence data solicitation operation 302 of FIG. 3.

In some implementations, operation 454 may include an operation 466 for soliciting the data indicating incidence of at least one objective occurrence based, at least in part, on referencing a hypothesis that identifies a relationship between one or more locations of the user and the one or more subjective user states as depicted in FIG. 4i. For instance, the objective occurrence data solicitation module 101 of the computing device 10 soliciting the data indicating incidence of at least one objective occurrence 71* based, at least in part, on the hypothesis referencing module 220 referencing a hypothesis 77 that identifies a relationship between one or more locations (e.g., Hawaii) of the user 20* and the one or more subjective user states (e.g., relaxation).

In some implementations, operation 454 may include an operation 467 for soliciting the data indicating incidence of at least one objective occurrence based, at least in part, on referencing a hypothesis that links the at least one subjective user state with one or more historical objective occurrences as depicted in FIG. 4i. For instance, the objective occurrence data solicitation module 101 of the computing device 10 soliciting the data indicating incidence of at least one objective occurrence 71* based, at least in part, on the hypothesis referencing module 220 referencing a hypothesis 77 that links the at least one subjective user state (e.g., hangover) with one or more historical objective occurrences (e.g., alcohol consumption).

In various implementations, the solicitation operation 302 of FIG. 3 may include operations that may be particularly suited to be executed by the mobile device 30 of FIG. 1a rather than by, for example, the computing device 10 of FIG. 1b. For instance, in some implementations the solicitation operation 302 of FIG. 3 may include an operation 468 for soliciting the data indicating incidence of at least one objective occurrence in response to a reception of a request to solicit the data indicating incidence of at least one objective occurrence, the request to solicit being remotely generated based, at least in part, on the hypothesis as depicted in FIG. 4i. For instance, the objective occurrence data solicitation module 101' of the mobile device 30 soliciting the data indicating incidence of at least one objective occurrence 71* in response to the request to solicit reception module 270 receiving a request to solicit the data indicating incidence of at least one objective occurrence 71*, the request to solicit being remotely generated (e.g., remotely generated by the computing device 10) based, at least in part, on the hypothesis 77. In various alternative implementations, the objective occurrence data solicitation module 101' of the mobile device 30 may solicit the data indicating incidence of at least one objective occurrence 71* from a user 20a, from one or more sensors 35, or from one or more third party sources 50.

Operation 468, in turn, may further include one or more additional operations. For example, in some implementations, operation 468 may include an operation 469 for soliciting the data indicating incidence of at least one objective occurrence in response to a reception of a request to solicit the data indicating incidence of at least one objective occurrence, the request to solicit being remotely generated based, at least in part, on the hypothesis and in response to the incidence of the at least one subjective user state associated with the user as depicted in FIG. 4i. For instance, the objective occurrence data solicitation module 101 ' of the mobile device 30 soliciting the data indicating incidence of at least one objective occurrence 71* in response to the request to solicit reception module 270 receiving a request to solicit the data indicating incidence of at least one objective occurrence 71*, the request to solicit being remotely generated based, at least in part, on the hypothesis 77 (e.g., a hypothesis linking upset stomach to ingestion of Mexican cuisine) and in response to the incidence of the at least one subjective user state (upset stomach) associated with the user 20a. In some implementations, such an incidence may have been initially reported by the user 20a via, for example, user interface 122'.

In some implementations, operation 468 may include an operation 470 for receiving the request to solicit the data indicating incidence of at least one objective occurrence via at least one of a wireless network or a wired network as depicted by FIG. 4i. For instance, the request to solicit reception module 270 of the mobile device 30 receiving the request to solicit the data indicating incidence of at least one objective occurrence 71* via at least one of a wireless network or a wired network 40.

Operation 470, in turn, may include an operation 471 for receiving the request to solicit the data indicating incidence of at least one objective occurrence from a network server as depicted by FIG. 4i. For instance, the request to solicit reception module 270 of the mobile device 30 receiving the request to solicit the data indicating incidence of at least one objective occurrence 71* from a network server (e.g., computing device 10).

Figure 4J:
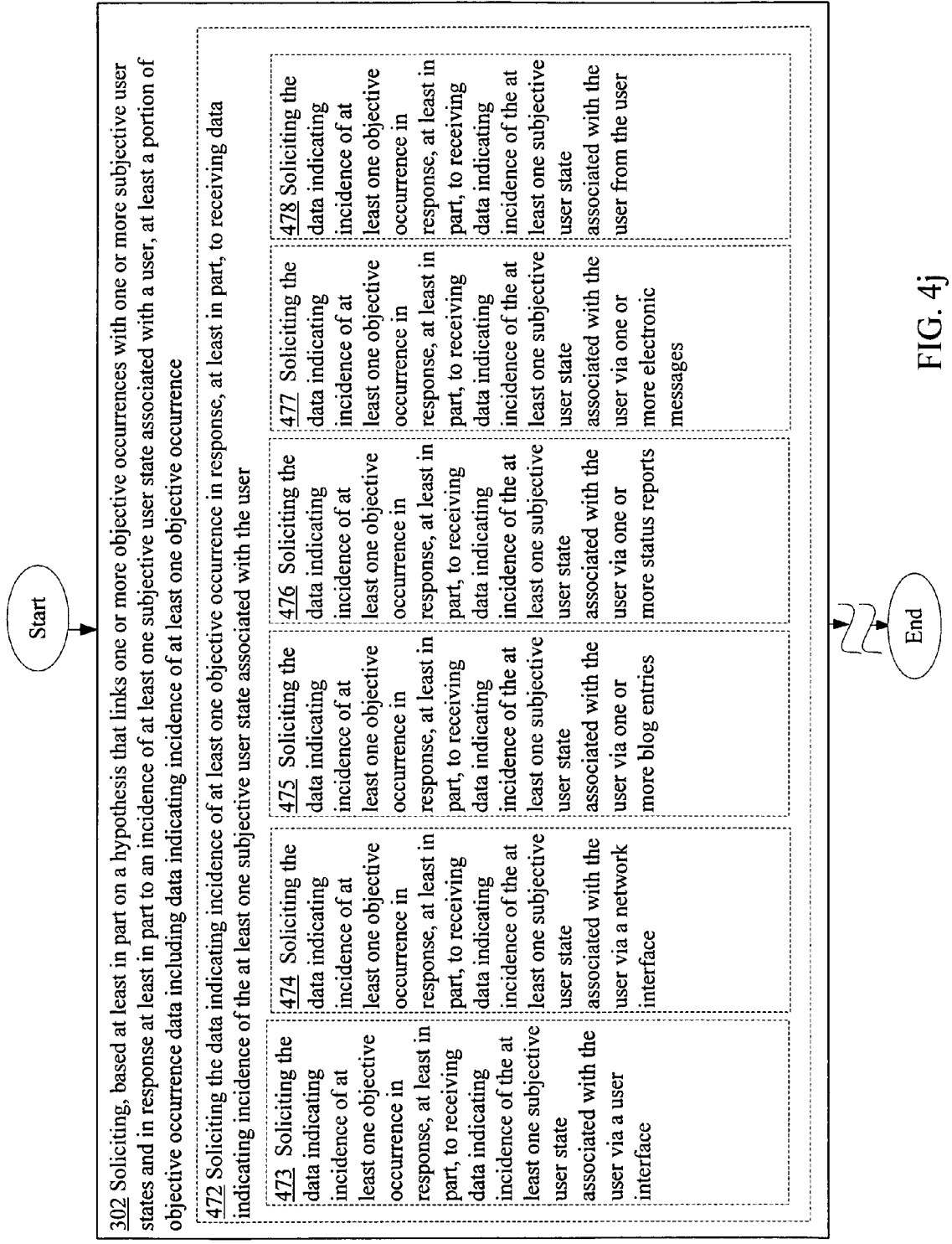
FIG. 4j is a high-level logic flowchart of a process depicting alternate implementations of the objective occurrence data solicitation operation 302 of FIG. 3.

In various implementations, the solicitation operation 302 of FIG. 3 may include an operation 472 for soliciting the data indicating incidence of at least one objective occurrence in response, at least in part, to receiving data indicating incidence of the at least one subjective user state associated with the user as depicted in FIG. 4j. For instance, the objective occurrence data solicitation module 101* of the computing device 10 or the mobile device 3 0 soliciting the data indicating incidence of at least one objective occurrence 71* in response, at least in part, to the subjective user state data reception module 224* receiving (e.g., via the network interface 120* or via the user interface 122*) data indicating incidence of the at least one subjective user state 61* associated with the user 20*.

In some implementations, operation 472 may farther include an operation 473 for soliciting the data indicating incidence of at least one objective occurrence in response, at least in part, to receiving data indicating incidence of the at least one subjective user state associated with the user via a user interface as depicted in FIG. 4j. For instance, the objective occurrence data solicitation module 101* of the computing device 10 or the mobile device 30 soliciting the data indicating incidence of at least one objective occurrence 71* in response, at least in part, to the subjective user state data reception module 224* receiving data indicating incidence of the at least one subjective user state 61* associated with the user 20* via a user interface 122*.

In some implementations, operation 472 may include an operation 474 for soliciting the data indicating incidence of at least one objective occurrence in response, at least in part, to receiving data indicating incidence of the at least one subjective user state associated with the user via a network interface as depicted in FIG. 4j. For instance, the objective occurrence data solicitation module 101 of the computing device 10 soliciting the data indicating incidence of at least one objective occurrence 71* in response, at least in part, to the subjective user state data reception module 224 receiving data indicating incidence of the at least one subjective user state 61a associated with the user 20a via a network interface 120.

In some implementations, operation 472 may include an operation 475 for soliciting the data indicating incidence of at least one objective occurrence in response, at least in part, to receiving data indicating incidence of the at least one subjective user state associated with the user via one or more blog entries as depicted in FIG. 4j. For instance, the objective occurrence data solicitation module 101 of the computing device 10 soliciting the data indicating incidence of at least one objective occurrence 71* in response, at least in part, to receiving data indicating incidence of the at least one subjective user state 61 a associated with the user 20a via one or more blog entries.

In some implementations, operation 472 may include an operation 476 for soliciting the data indicating incidence of at least one objective occurrence in response, at least in part, to receiving data indicating incidence of the at least one subjective user state associated with the user via one or more status reports as depicted in FIG. 4j. For instance, the objective occurrence data solicitation module 101 of the computing device 10 soliciting the data indicating incidence of at least one objective occurrence 71* in response, at least in part, to receiving data indicating incidence of the at least one subjective user state 61a associated with the user 20a via one or more status reports.

In some implementations, operation 472 may include an operation 477 for soliciting the data indicating incidence of at least one objective occurrence in response, at least in part, to receiving data indicating incidence of the at least one subjective user state associated with the user via one or more electronic messages as depicted in FIG. 4j. For instance, the objective occurrence data solicitation module 101 of the computing device 10 soliciting the data indicating incidence of at least one objective occurrence 71* in response, at least in part, to receiving data indicating incidence of the at least one subjective user state 61a associated with the user 20a via one or more electronic messages.

In some implementations, operation 472 may include an operation 478 for soliciting the data indicating incidence of at least one objective occurrence in response, at least in part, to receiving data indicating incidence of the at least one subjective user state associated with the user from the user as depicted in FIG. 4j. For instance, the objective occurrence data solicitation module 101* of the computing device 10 or the mobile device 30 soliciting the data indicating incidence of at least one objective occurrence 71* in response, at least in part, to receiving data indicating incidence of the at least one subjective user state 61* associated with the user 20* from the user 20*.

Figure 5A:
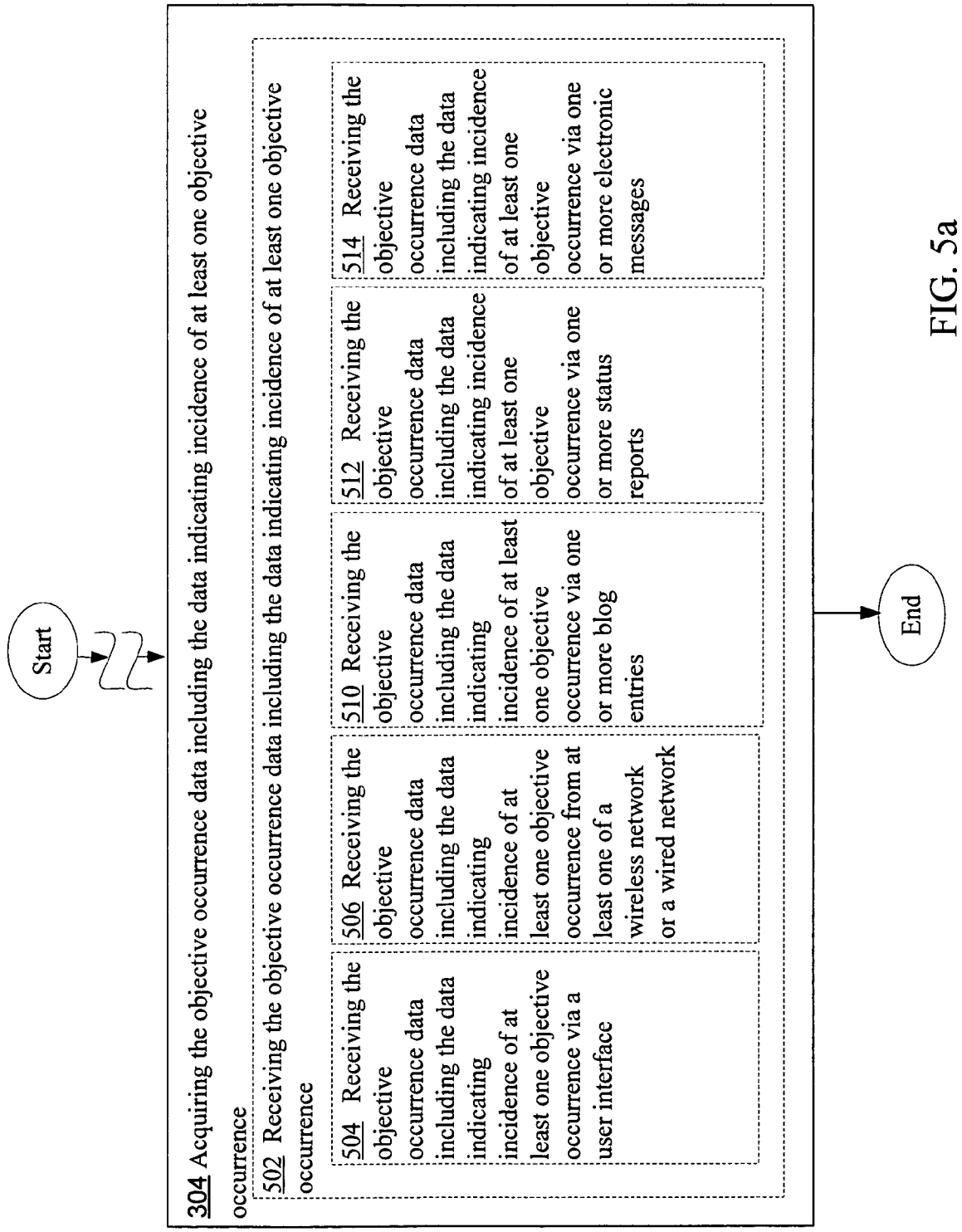
FIG. 5a is a high-level logic flowchart of a process depicting alternate implementations of the objective occurrence data acquisition operation 304 of FIG. 3.

Referring back to FIG. 3, the objective occurrence data acquisition operation 304 may include one or more additional operations in various alternative implementations. For example, in various implementations, the objective occurrence data acquisition operation 304 may include a reception operation 502 for receiving the objective occurrence data including the data indicating incidence of at least one objective occurrence as depicted in FIG. 5a. For instance, the objective occurrence data reception module 234* of the computing device 10 or the mobile device 30 receiving (e.g., via the user interface 122* or via at least one of a wireless network or wired network 40) the objective occurrence data 70* including the data indicating incidence of at least one objective occurrence 71*.

In various alternative implementations, the reception module 502 may include one or more additional operations. For example, in some implementations, the reception operation 502 may include an operation 504 for receiving the objective occurrence data including the data indicating incidence of at least one objective occurrence via a user interface as depicted in FIG. 5a. For instance, the user interface data reception module 235* of the computing device 10 or the mobile device 30 receiving the objective occurrence data 70* including the data indicating incidence of at least one objective occurrence 71* via a user interface 122* (e.g., a microphone, a keypad, a touchscreen, and so forth).

In some implementations, the reception operation 502 may include an operation 506 for receiving the objective occurrence data including the data indicating incidence of at least one objective occurrence from at least one of a wireless network or a wired network as depicted in FIG. 5a. For instance, the network interface data reception module 236* of the computing device 10 or the mobile device 30 receiving the objective occurrence data 70* including the data indicating incidence of at least one objective occurrence 71* from at least one of a wireless network or a wired network 40.

In some implementations, the reception operation 502 may include an operation 510 for receiving the objective occurrence data including the data indicating incidence of at least one objective occurrence via one or more blog entries as depicted in FIG. 5a. For instance, the network interface data reception module 236* of the computing device 10 or the mobile device 30 receiving the objective occurrence data 70* including the data indicating incidence of at least one objective occurrence 71* via one or more blog entries (e.g., microblog entries).

In some implementations, the reception operation 502 may include an operation 512 for receiving the objective occurrence data including the data indicating incidence of at least one objective occurrence via one or more status reports as depicted in FIG. 5a. For instance, the network interface data reception module 236* of the computing device 10 or the mobile device 30 receiving the objective occurrence data 70* including the data indicating incidence of at least one objective occurrence 71* via one or more status reports (e.g., social networking status reports).

In some implementations, the reception operation 502 may include an operation 514 for receiving the objective occurrence data including the data indicating incidence of at least one objective occurrence via one or more electronic messages as depicted in FIG. 5a. For instance, the network interface data reception module 236* of the computing device 10 or the mobile device 30 receiving the objective occurrence data 70* including the data indicating incidence of at least one objective occurrence 71* via one or more electronic messages (e.g., text messages, email messages, IM messages, or other types of messages).

Figure 5B:
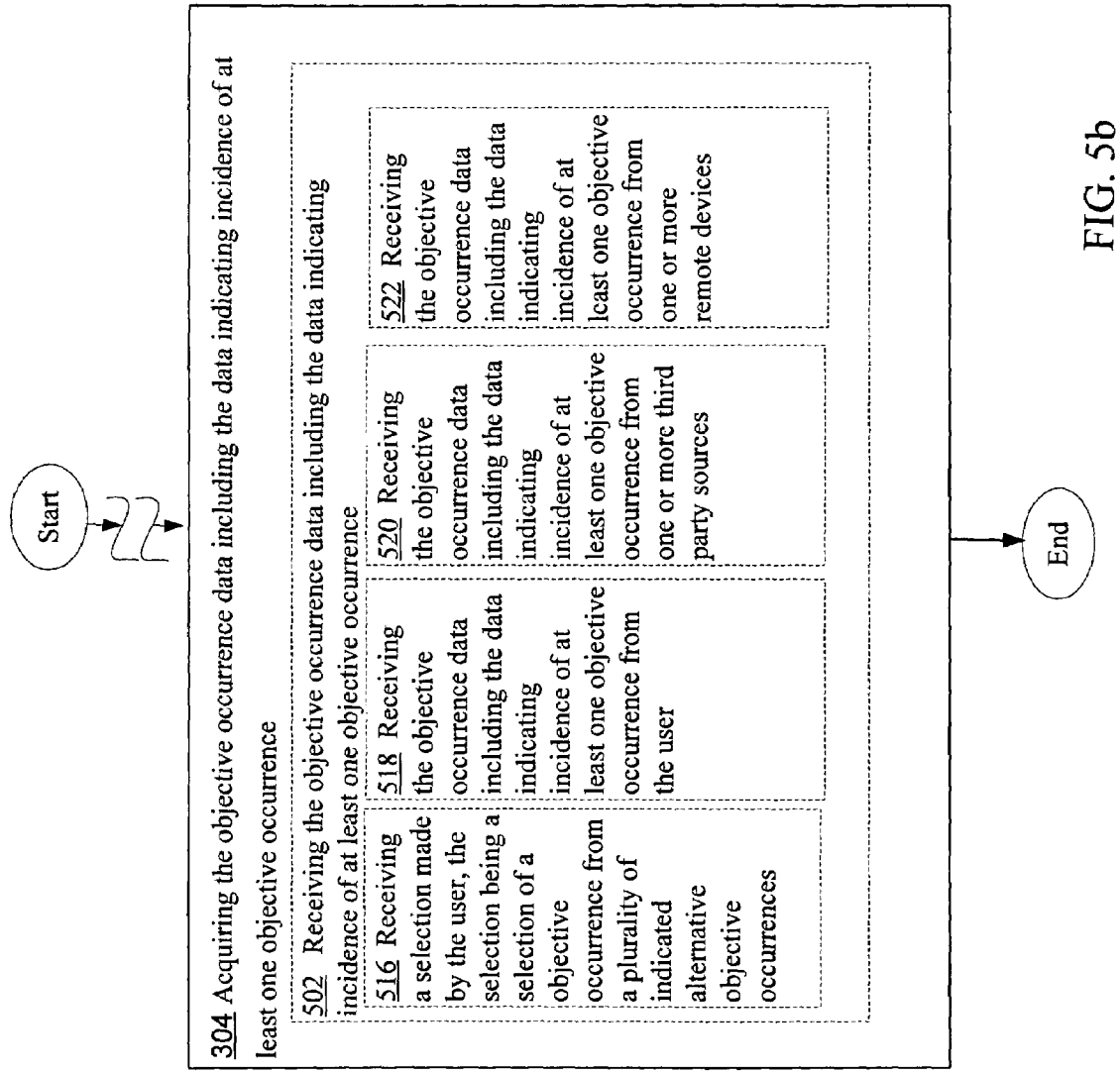
FIG. 5b is a high-level logic flowchart of a process depicting alternate implementations of the objective occurrence data acquisition operation 304 of FIG. 3.

In some implementations, the reception operation 502 may include an operation 516 for receiving a selection made by the user, the selection being a selection of an objective occurrence from a plurality of indicated alternative objective occurrences as depicted in FIG. 5b. For instance, the objective occurrence data reception module 234* of the computing device 10 or the mobile device 30 receiving a selection made by the user 20*, the selection being a selection of an objective occurrence from a plurality of indicated alternative objective occurrences (e.g., as indicated via a user interface 122*).

In some implementations, the reception operation 502 may include an operation 518 for receiving the objective occurrence data including the data indicating incidence of at least one objective occurrence from the user as depicted in FIG. 5b. For instance, the objective occurrence data reception module 234* of the computing device 10 or the mobile device 30 receiving the objective occurrence data 70c including the data indicating incidence of at least one objective occurrence 71c from the user 20*.

In some implementations, the reception operation 502 may include an operation 520 for receiving the objective occurrence data including the data indicating incidence of at least one objective occurrence from one or more third party sources as depicted in FIG. 5b. For instance, the objective occurrence data reception module 234* of the computing device 10 or the mobile device 30 receiving the objective occurrence data 70a including the data indicating incidence of at least one objective occurrence 71a from one or more third party sources 50 (e.g., other users, content providers, health care providers, health fitness providers, social organizations, business, and so forth).

In some implementations, the reception operation 502 may include an operation 522 for receiving the objective occurrence data including the data indicating incidence of at least one objective occurrence from one or more remote devices as depicted in FIG. 5b. For instance, the objective occurrence data reception module 234* of the computing device 10 or the mobile device 30 receiving the objective occurrence data 70b including the data indicating incidence of at least one objective occurrence 71b from one or more remote devices (e.g., sensors 35 or remote network servers).

Figure 5C:
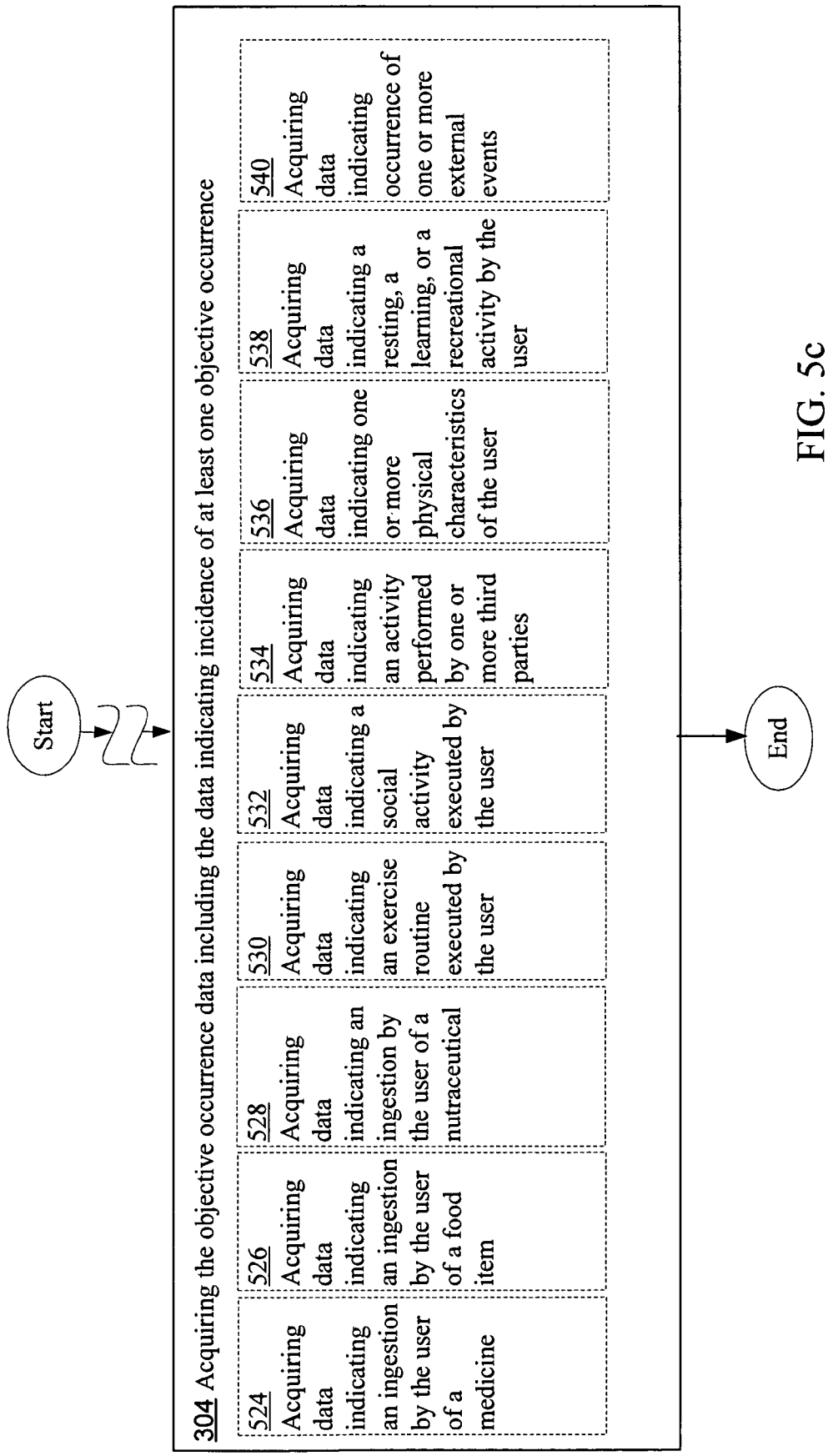
FIG. 5c is a high-level logic flowchart of a process depicting alternate implementations of the objective occurrence data acquisition operation 304 of FIG. 3.

In some implementations, the objective occurrence data acquisition operation 304 of FIG. 3 may include an operation 524 for acquiring data indicating an ingestion by the user of a medicine as depicted in FIG. 5c. For instance, the objective occurrence data acquisition module 104* of the computing device 10 or the mobile device 30 acquiring (e.g., receiving, retrieving, or accessing) data indicating an ingestion by the user 20* of a medicine (e.g., a dosage of a beta blocker).

In some implementations, the objective occurrence data acquisition operation 304 may include an operation 526 for acquiring data indicating an ingestion by the user of a food item as depicted in FIG. 5c. For instance, the objective occurrence data acquisition module 104* of the computing device 10 or the mobile device 30 acquiring data indicating an ingestion by the user 20* of a food item (e.g., a fruit).

In some implementations, the objective occurrence data acquisition operation 304 may include an operation 528 for acquiring data indicating an ingestion by the user of a nutraceutical as depicted in FIG. 5c. For instance, the objective occurrence data acquisition module 104* of the computing device 10 or the mobile device 30 acquiring data indicating an ingestion by the user 20* of a nutraceutical (e.g. broccoli).

In some implementations, the objective occurrence data acquisition operation 304 may include an operation 530 for acquiring data indicating an exercise routine executed by the user as depicted in FIG. 5c. For instance, the objective occurrence data acquisition module 104* of the computing device 10 or the mobile device 30 acquiring data indicating an exercise routine (e.g., exercising on an exercise machine such as a treadmill) executed by the user 20*.

In some implementations, the objective occurrence data acquisition operation 304 may include an operation 532 for acquiring data indicating a social activity executed by the user as depicted in FIG. 5c. For instance, the objective occurrence data acquisition module 104* of the computing device 10 or the mobile device 30 acquiring data indicating a social activity (e.g., hiking or skiing with friends, dates, dinners, and so forth) executed by the user 20*.

In some implementations, the objective occurrence data acquisition operation 304 may include an operation 534 for acquiring data indicating an activity performed by one or more third parties as depicted in FIG. 5c. For instance, the objective occurrence data acquisition module 104* of the computing device 10 or the mobile device 30 acquiring data indicating an activity performed by one or more third parties (e.g., spouse leaving home to visit relatives).

In some implementations, the objective occurrence data acquisition operation 304 may include an operation 536 for acquiring data indicating one or more physical characteristics of the user as depicted in FIG. 5c. For instance, the objective occurrence data acquisition module 104* of the computing device 10 or the mobile device 30 acquiring data indicating one or more physical characteristics (e.g., blood sugar or blood pressure level) of the user 20*.

In some implementations, the objective occurrence data acquisition operation 304 may include an operation 538 for acquiring data indicating a resting, a learning, or a recreational activity by the user as depicted in FIG. 5c. For instance, the objective occurrence data acquisition module 104* of the computing device 10 or the mobile device 30 acquiring data indicating a resting (e.g., napping), a learning (e.g., attending a lecture), or a recreational activity (e.g., boating) by the user 20*.

In some implementations, the objective occurrence data acquisition operation 304 may include an operation 540 for acquiring data indicating occurrence of one or more external events as depicted in FIG. 5c. For instance, the objective occurrence data acquisition module 104* of the computing device 10 or the mobile device 30 acquiring data indicating occurrence of one or more external events (e.g., sub-freezing weather).

Figure 5D:
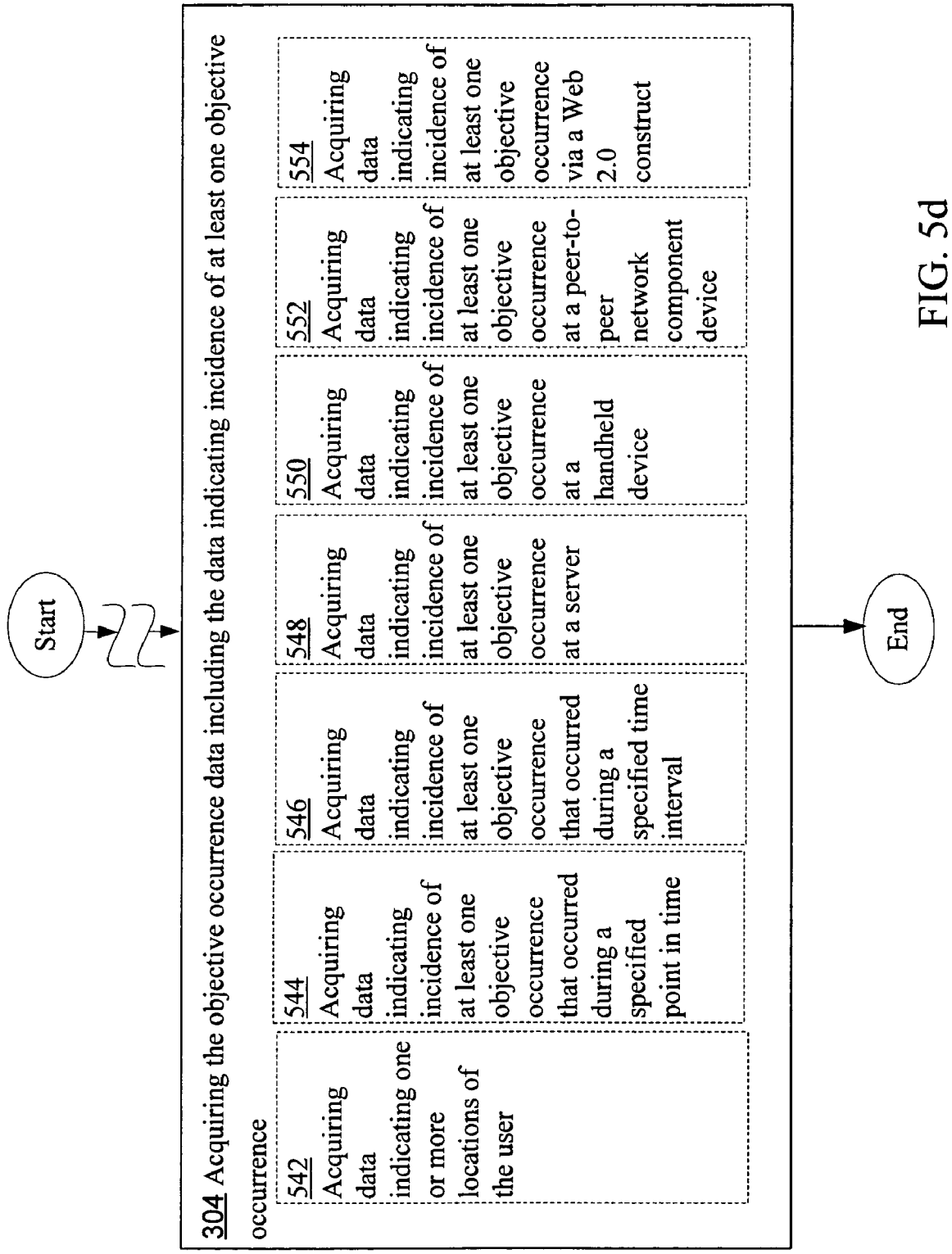
FIG. 5d is a high-level logic flowchart of a process depicting alternate implementations of the objective occurrence data acquisition operation 304 of FIG. 3.

In some implementations, the objective occurrence data acquisition operation 304 may include an operation 542 for acquiring data indicating one or more locations of the user as depicted in FIG. 5d. For instance, the objective occurrence data acquisition module 104* of the computing device 10 or the mobile device 30 acquiring data indicating one or more locations of the user 20*.

In some implementations, the objective occurrence data acquisition operation 304 may include an operation 544 for acquiring data indicating incidence of at least one objective occurrence that occurred during a specified point in time as depicted in FIG. 5d. For instance, the objective occurrence data acquisition module 104* of the computing device 10 or the mobile device 30 acquiring data indicating incidence of at least one objective occurrence 71* that occurred during a specified point in time (e.g., as specified through a user interface 122*).

In some implementations, the objective occurrence data acquisition operation 304 may include an operation 546 for acquiring data indicating incidence of at least one objective occurrence that occurred during a specified time interval as depicted in FIG. 5d. For instance, the objective occurrence data acquisition module 104* of the computing device 10 or the mobile device 30 acquiring data indicating incidence of at least one objective occurrence that occurred during a specified time interval (e.g., as specified through a user interface 122*).

In some implementations, the objective occurrence data acquisition operation 304 may include an operation 548 for acquiring data indicating incidence of at least one objective occurrence at a server as depicted in FIG. 5d. For instance, when the computing device 10 is a server and acquires the data indicating incidence of at least one objective occurrence 71*.

In some implementations, the objective occurrence data acquisition operation 304 may include an operation 550 for acquiring data indicating incidence of at least one objective occurrence at a handheld device as depicted in FIG. 5d. For instance, when the computing device 10 is a standalone device and is a handheld device or when the mobile device 30 is a handheld device and acquires the data indicating incidence of at least one objective occurrence 71*.

In some implementations, the objective occurrence data acquisition operation 304 may include an operation 552 for acquiring data indicating incidence of at least one objective occurrence at a peer-to-peer network component device as depicted in FIG. 5d. For instance, when the computing device 10 is a standalone device and is a peer-to-peer network component device or the mobile device 30 is a peer-to-peer network component device and acquires the data indicating incidence of at least one objective occurrence 71*.

In some implementations, the objective occurrence data acquisition operation 304 may include an operation 554 for acquiring data indicating incidence of at least one objective occurrence via a Web 2.0 construct as depicted in FIG. 5d. For instance, when the computing device 10 or the mobile device 30 is running a web 2.0 application 268 and acquires the data indicating incidence of at least one objective occurrence 71*.

Figure 6:
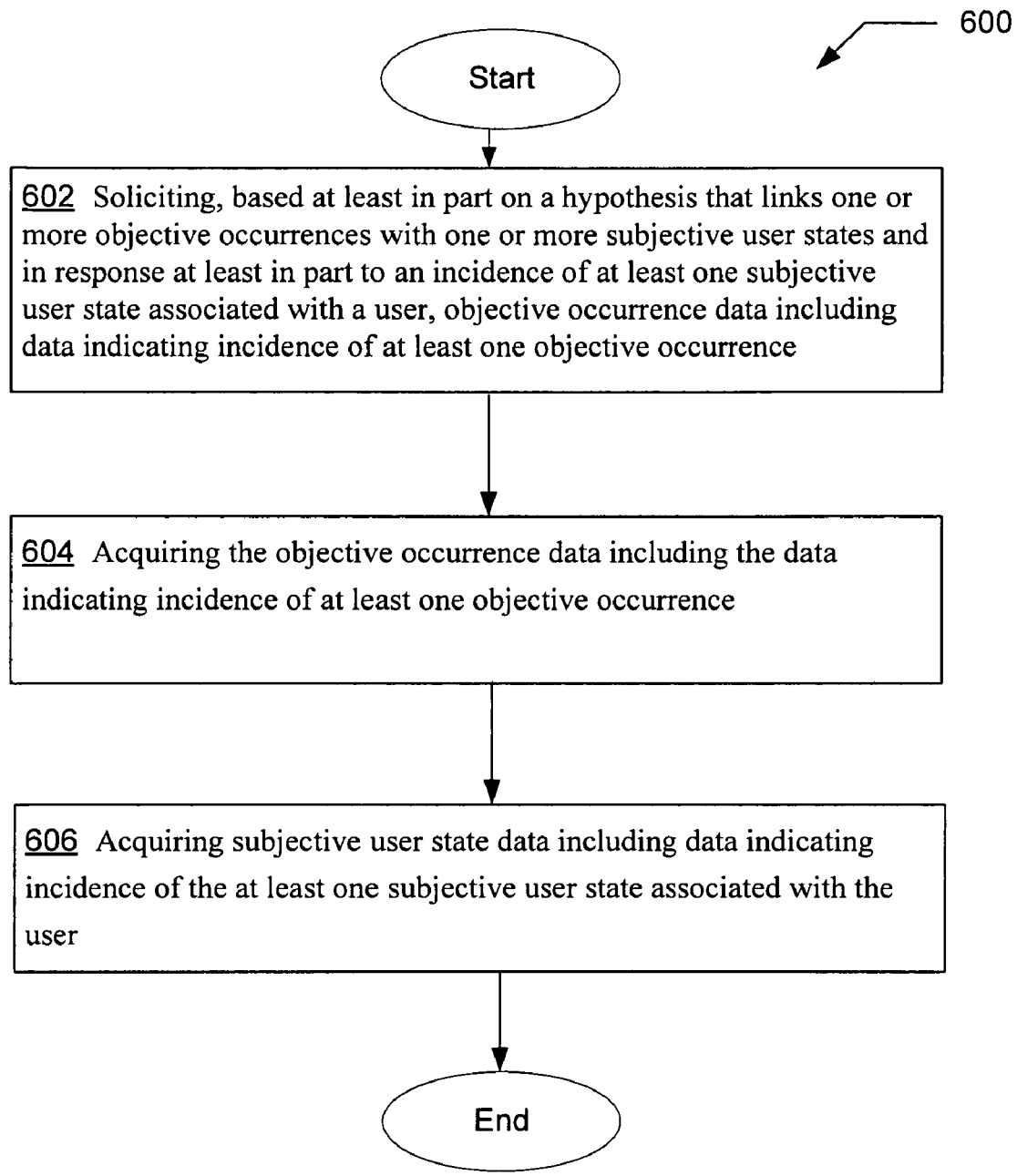
FIG. 6 is a high-level logic flowchart of another process.

Referring to FIG. 6 illustrating another operational flow 600 in accordance with various embodiments. Operational flow 600 includes certain operations that mirror the operations included in operational flow 300 of FIG. 3. For example, operational flow 600 includes an objective occurrence data solicitation operation 602 and an objective occurrence data acquisition operation 604 that correspond to and mirror the objective occurrence data solicitation operation 302 and the objective occurrence data acquisition operation 304, respectively, of FIG. 3.

In addition, and unlike operation 300 of FIG. 3, operational flow 600 may additionally include a subjective user state data acquisition operation 606 for acquiring subjective user state data including data indicating incidence of the at least one subjective user state associated with the user as depicted in FIG. 6. For instance, the subjective user state data acquisition module 102* of the computing device 10 or the mobile device 30 acquiring (e.g., receiving, gathering, or retrieving via the network interface 120* or via the user interface 122*) subjective user state data 60* including data indicating incidence of the at least one subjective user state 61* associated with the user 20*.

Figure 7A:
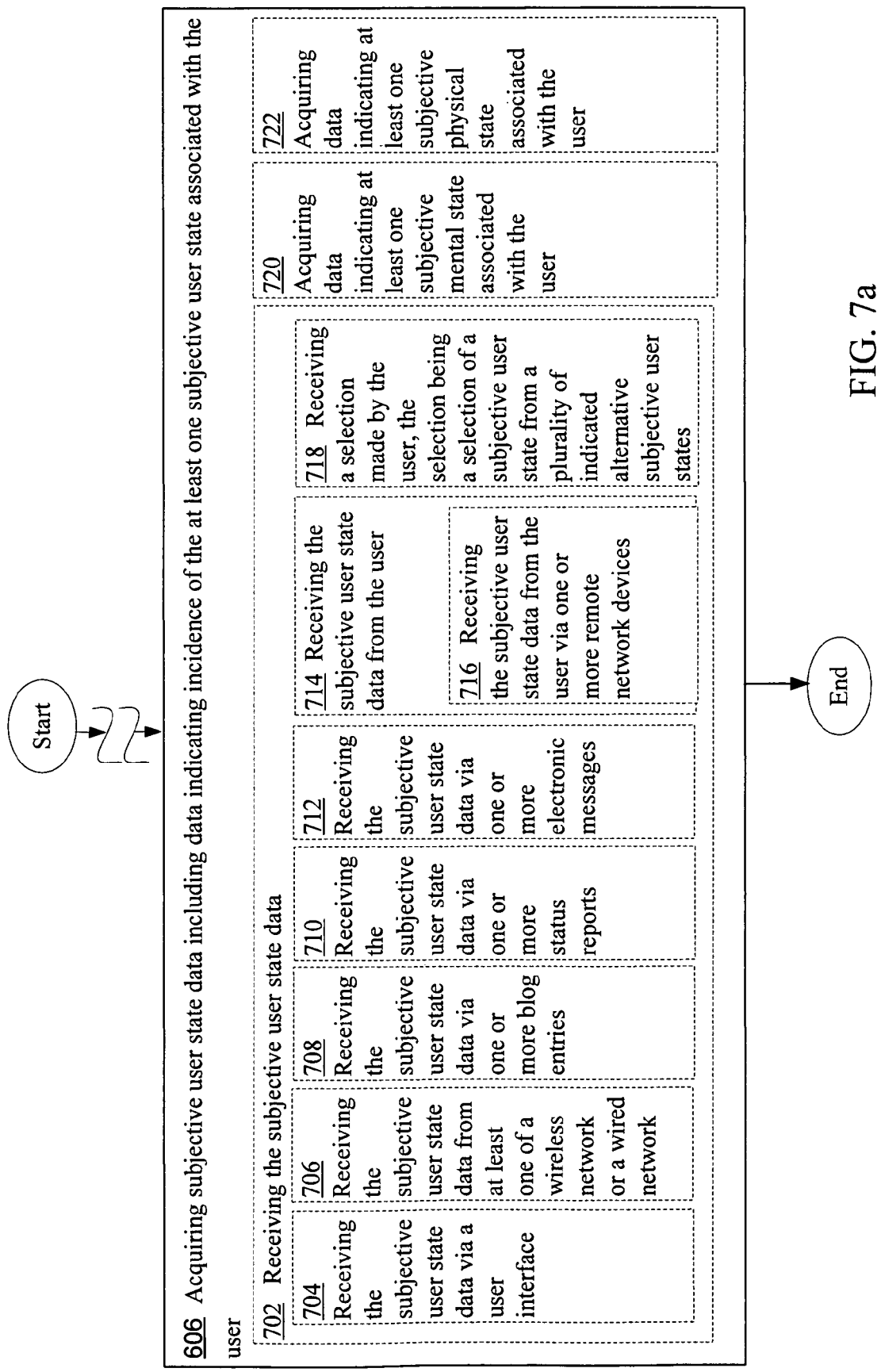
FIG. 7a is a high-level logic flowchart of a process depicting alternate implementations of the subjective user state data acquisition operation 606 of FIG. 6.

In various alternative implementations, the subjective user state data acquisition operation 606 may include one or more additional operations. For example, in some implementations, the subjective user state data acquisition operation 606 may include a reception operation 702 for receiving the subjective user state data as depicted in FIG. 7a. For instance, the subjective user state data reception module 224* of the computing device 10 or the mobile device 30 receiving the subjective user state data 60*.

The reception operation 702, in turn, may include one or more additional operations in various alternative implementations. For example, in some implementations, the reception operation 702 may include an operation 704 for receiving the subjective user state data via a user interface as depicted in FIG. 7a. For instance, the user interface reception module 226* of the computing device 10 (e.g., when the computing device 10 is a standalone device) or the mobile device 30 receiving the subjective user state data 60* via a user interface 122* (e.g., a keyboard, a mouse, a touchscreen, a microphone, an image capturing device such as a digital camera, and/or other interface devices).

In some implementations, the reception operation 702 may include an operation 706 for receiving the subjective user state data from at least one of a wireless network or a wired network as depicted in FIG. 7a. For instance, the network interface reception module 227 of the computing device 10 (e.g., when the computing device 10 is a server) receiving the subjective user state data 60* from at least one of a wireless network or a wired network 40.

In some implementations, the reception operation 702 may include an operation 708 for receiving the subjective user state data via one or more blog entries as depicted in FIG. 7a. For instance, the network interface reception module 227 of the computing device 10 (e.g., when the computing device 10 is a server) receiving the subjective user state data 60* via one or more blog entries (e.g., microblog entries).

In some implementations, the reception operation 702 may include an operation 710 for receiving the subjective user state data via one or more status reports as depicted in FIG. 7a. For instance, the network interface reception module 227 of the computing device 10 (e.g., when the computing device 10 is a server) receiving the subjective user state data 60* via one or more status reports (e.g., social networking status reports).

In some implementations, the reception operation 702 may include an operation 712 for receiving the subjective user state data via one or more electronic messages as depicted in FIG. 7a. For instance, the network interface reception module 227 of the computing device 10 (e.g., when the computing device 10 is a server) receiving the subjective user state data 60* via one or more electronic messages (e.g., text message, email message, audio or text message, IM message, or other types of electronic messages).

In some implementations, the reception operation 702 may include an operation 714 for receiving the subjective user state data from the user as depicted in FIG. 7a. For instance, the subjective user state data reception module 224* of the computing device 10 or the mobile device 30 receiving the subjective user state data 60* from the user 20*.

Operation 714, in turn, may further include an operation 716 for receiving the subjective user state data from the user via one or more remote network devices as depicted in FIG. 7a. For instance, the network interface reception module 227 of the computing device 10 (e.g., when the computing device 10 is a server) receiving the subjective user state data 60a from the user 20a via one or more remote network devices (e.g., mobile device 30 or other devices such as other network servers).

In some implementations, the reception operation 702 may include an operation 718 for receiving a selection made by the user, the selection being a selection of a subjective user state from a plurality of indicated alternative subjective user states as depicted in FIG. 7a. For instance, the subjective user state data reception module 224* of the computing device 10 or the mobile device 30 receiving (e.g., receiving from at least one of a wireless network or a wired network 40 or via a user interface 122*) a selection made by the user 20*, the selection being a selection of a subjective user state from a plurality of indicated alternative subjective user states (e.g., as indicated through a user interface 122*).

In various implementations, the subjective user state data acquisition operation 606 of FIG. 6 may include an operation 720 for acquiring data indicating at least one subjective mental state associated with the user as depicted in FIG. 7a. For instance, the subjective user state data acquisition module 102* of the computing device 10 or the mobile device 30 acquiring (e.g., receiving, retrieving, or accessing) data indicating at least one subjective mental state (e.g., happiness, sadness, depression, anger, frustration, elation, fear, alertness, sleepiness, envy, and so forth) associated with the user 20*.

In some implementations, the subjective user state data acquisition operation 606 may include an operation 722 for acquiring data indicating at least one subjective physical state associated with the user as depicted in FIG. 7a. For instance, the subjective user state data acquisition module 102* of the computing device 10 or the mobile device 30 acquiring (e.g., receiving, retrieving, or accessing) data indicating at least one subjective physical state (e.g., pain, blurring vision, hearing loss, upset stomach, physical exhaustion, and so forth) associated with the user 20*.

Figure 7B:
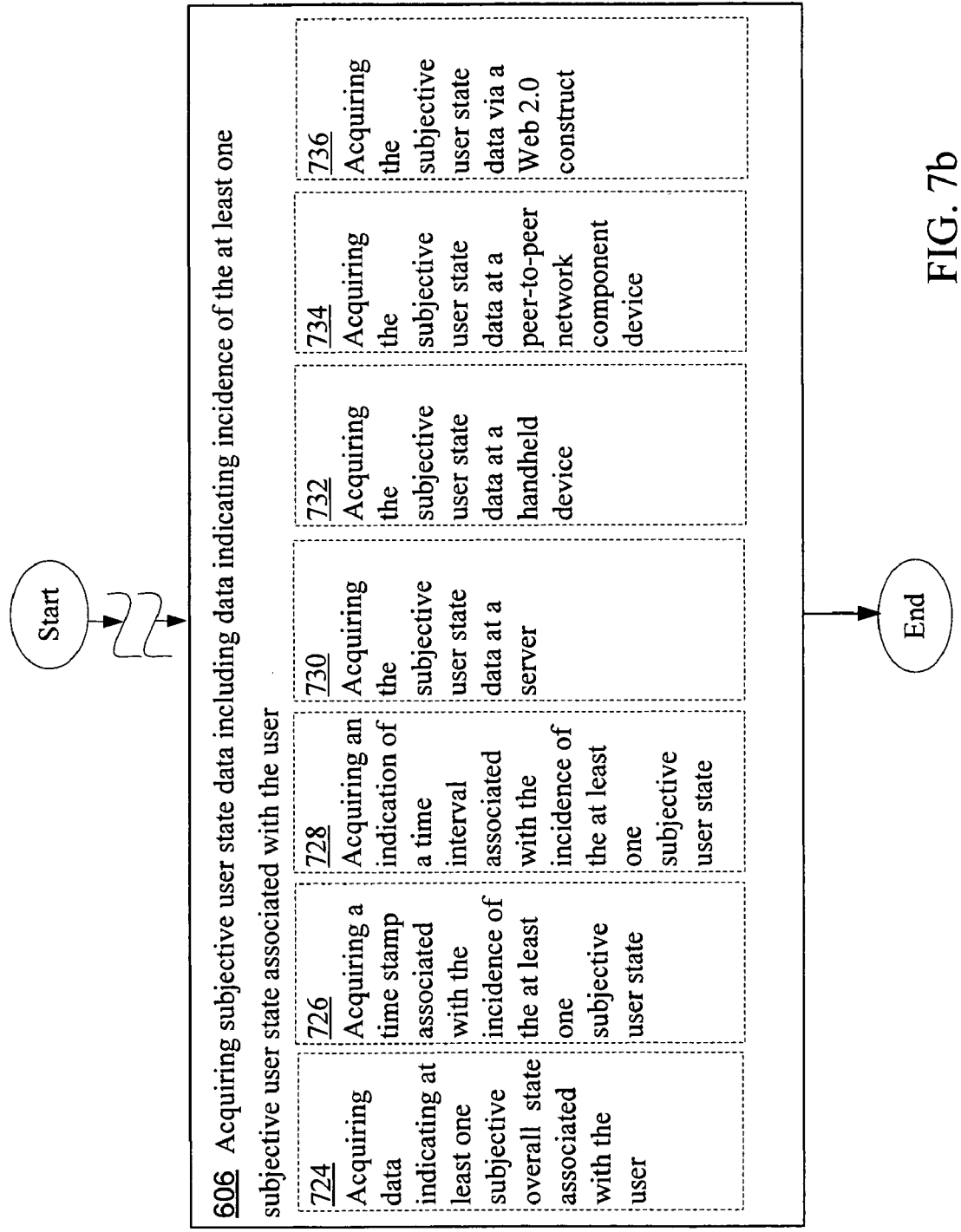
FIG. 7b is a high-level logic flowchart of a process depicting alternate implementations of the subjective user state data acquisition operation 606 of FIG. 6.

In some implementations, the subjective user state data acquisition operation 606 may include an operation 724 for acquiring data indicating at least one subjective overall state associated with the user as depicted in FIG. 7b. For instance, the subjective user state data acquisition module 102* of the computing device 10 or the mobile device 30 acquiring (e.g., receiving, retrieving, or accessing) data indicating at least one subjective overall state (e.g., good, bad, well, lousy, and so forth) associated with the user 20*.

In some implementations, the subjective user state data acquisition operation 606 may include an operation 726 for acquiring a time stamp associated with the incidence of the at least one subjective user state as depicted in FIG. 7b. For instance, the time stamp acquisition module 230* of the computing device 10 or the mobile device 30 acquiring (e.g., receiving or generating) a time stamp associated with the incidence of the at least one subjective user state.

In some implementations, the subjective user state data acquisition operation 606 may include an operation 728 for acquiring an indication of a time interval associated with the incidence of the at least one subjective user state as depicted in FIG. 7b. For instance, the time interval acquisition module 231* of the computing device 10 or the mobile device 30 acquiring (e.g., receiving or generating) an indication of a time interval associated with the incidence of the at least one subjective user state.

In some implementations, the subjective user state data acquisition operation 606 may include an operation 730 for acquiring the subjective user state data at a server as depicted in FIG. 7b. For instance, when the computing device 10 is a network server and is acquiring the subjective user state data 60a.

In some implementations, the subjective user state data acquisition operation 606 may include an operation 732 for acquiring the subjective user state data at a handheld device as depicted in FIG. 7b. For instance, when the computing device 10 is a standalone device and is a handheld device (e.g., a cellular telephone, a smartphone, an MID, an UMPC, or a convergent device such as a PDA) or the mobile device 30 is a handheld device, and the computing device 10 or the mobile device 30 is acquiring the subjective user state data 60*.

In some implementations, the subjective user state data acquisition operation 606 may include an operation 734 for acquiring the subjective user state data at a peer-to-peer network component device as depicted in FIG. 7b. For instance, when the computing device 10 or the mobile device 30 is a peer-to-peer network component device and the computing device 10 or the mobile device 30 is acquiring the subjective user state data 60*.

In some implementations, the subjective user state data acquisition operation 606 may include an operation 736 for acquiring the subjective user state data via a Web 2.0 construct as depicted in FIG. 7b. For instance, when the computing device 10 or the mobile device 30 acquires the subjective user state data 60* via a Web 2.0 construct (e.g., Web 2.0 application 268).

Figure 8:
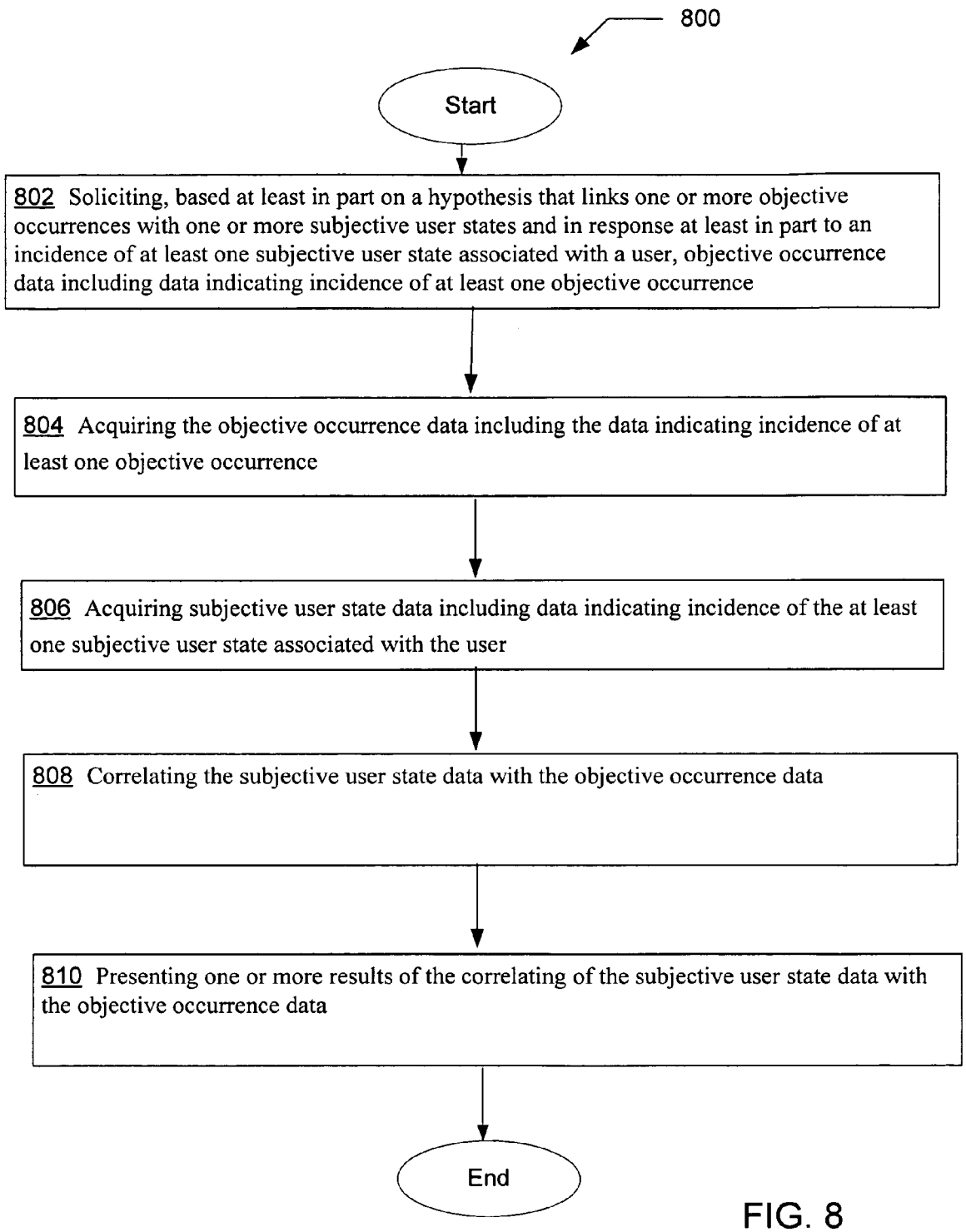
FIG. 8 is a high-level logic flowchart of still another process.

Referring now to FIG. 8 illustrating still another operational flow 800 in accordance with various embodiments. In some embodiments, operational flow 800 may be particularly suited to be performed by the computing device 10, which may be a network server or a standalone device. Operational flow 800 includes operations that mirror the operations included in the operational flow 600 of FIG. 6. For example, operational flow 800 may include an objective occurrence data solicitation operation 802, an objective occurrence data acquisition operation 804, and a subjective user state data acquisition operation 806 that corresponds to and mirror the objective occurrence data solicitation operation 602, the objective occurrence data acquisition operation 604, and the subjective user state data acquisition operation 606, respectively, of FIG. 6.

In addition, and unlike operational flow 600, operational flow 800 may further include a correlation operation 808 for correlating the subjective user state data with the objective occurrence data and a presentation operation 810 for presenting one or more results of the correlating of the subjective user state data with the objective occurrence data as depicted in FIG. 8. For instance, the correlation module 106 of the computing device 10 correlating (e.g., linking or determining a relationship between) the subjective user state data 60\* with the objective occurrence data 70\*. The presentation module 108 of the computing device 10 may then present (e.g., transmit via a network interface 120 or indicate via a user interface 122) one or more results of the correlation operation 808 performed by the correlation module 106.

Figure 9:
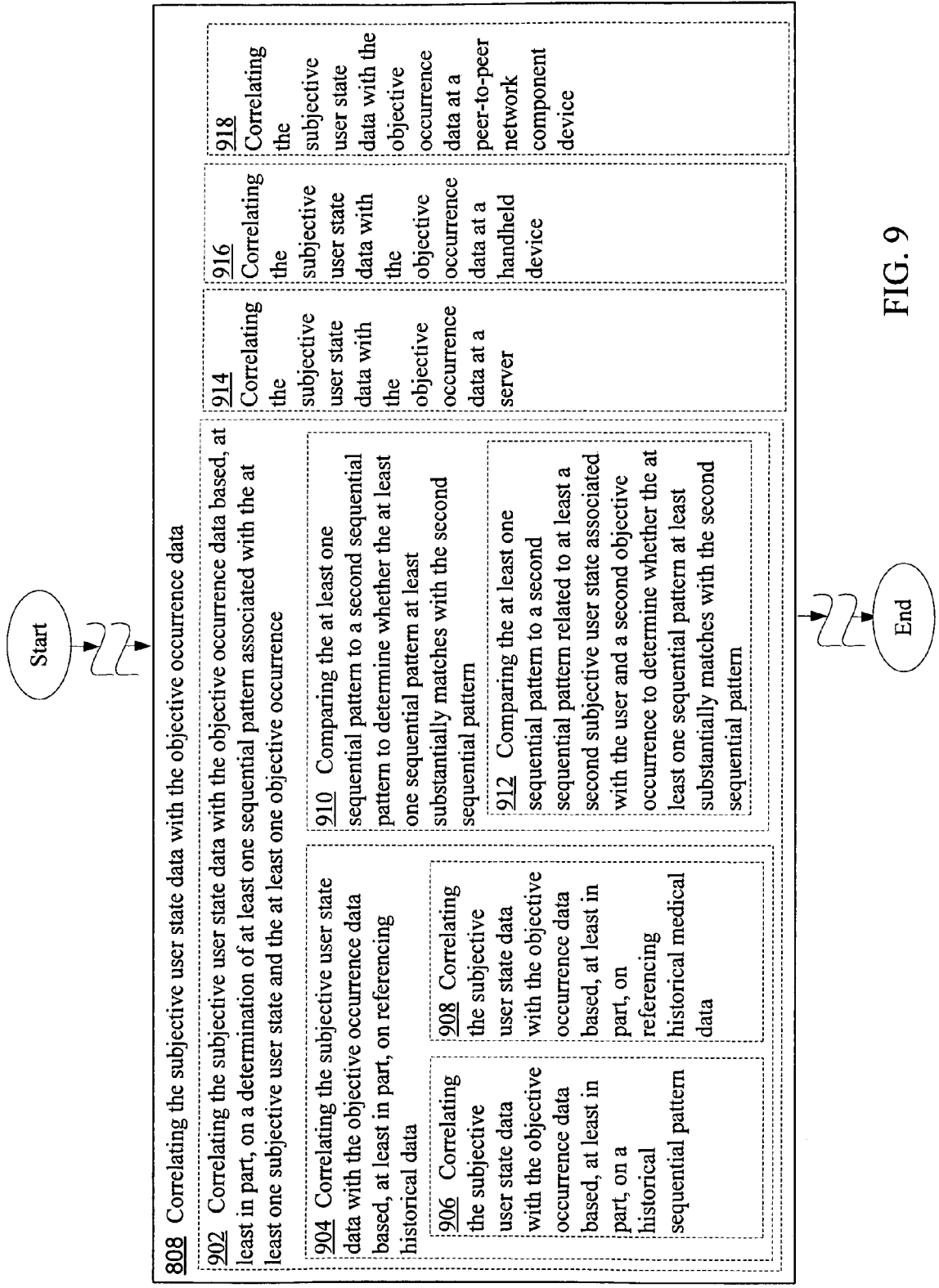
FIG. 9 is a high-level logic flowchart of a process depicting alternate implementations of the correlation operation 808 of FIG. 8.

In various alternative implementations, the correlation operation 808 may include one or more additional operations. For example, in some implementations, the correlation operation 808 may include an operation 902 for correlating the subjective user state data with the objective occurrence data based, at least in part, on a determination of at least one sequential pattern associated with the at least one subjective user state and the at least one objective occurrence as depicted in FIG. 9. For instance, the correlation module 106 of the computing device 10 correlating the subjective user state data 60\* with the objective occurrence data 70\* based, at least in part, on the sequential pattern determination module 242 determining at least one sequential pattern associated with the at least one subjective user state indicated by the subjective user state data 60\* and the at least one objective occurrence indicated by the objective occurrence data 70\*.

Operation 902, in turn, may further include one or more additional operations. For example, in some implementations, operation 902 may include an operation 904 for correlating the subjective user state data with the objective occurrence data based, at least in part, on referencing historical data as depicted in FIG. 9. For instance, the correlation module 106 of the computing device 10 correlating the subjective user state data 60\* with the objective occurrence data 70\* based, at least in part, on the historical data referencing module 243 referencing historical data 78. Examples of historical data 78 includes, for example, previously reported incidences of subjective user states associated with the user 20\* and/or with other users as they relate to objective occurrences, historical sequential patterns associated with the user 20\* or with other users, historical medical data relating to the user 20 and/or other users, and/or other types of historical data 78.

In some implementations, operation 904 may include an operation 906 for correlating the subjective user state data with the objective occurrence data based, at least in part, on a historical sequential pattern as further depicted in FIG. 9. For instance, the correlation module 106 of the computing device 10 correlating the subjective user state data 60\* with the objective occurrence data 70\* based, at least in part, on the historical data referencing module 243 referencing a historical sequential pattern associated with the user 20\*, with other users, and/or with a subset of the general population.

In some implementations, operation 904 may include an operation 908 for correlating the subjective user state data with the objective occurrence data based, at least in part, on referencing historical medical data as depicted in FIG. 9. For instance, the correlation module 106 of the computing device 10 correlating the subjective user state data 60\* with the objective occurrence data 70\* based, at least in part, on the historical data referencing module 243 referencing historical medical data (e.g., genetic, metabolome, or proteome information or medical records of the user 20\* or of others related to, for example, diabetes or heart disease).

In various implementations, operation 902 may include an operation 910 for comparing the at least one sequential pattern to a second sequential pattern to determine whether the at least one sequential pattern at least substantially matches with the second sequential pattern as depicted in FIG. 9. For instance, the sequential pattern comparison module 248 of the computing device 10 comparing the at least one sequential pattern to a second sequential pattern to determine whether the at least one sequential pattern at least substantially matches with the second sequential pattern.

Operation 910, in some implementations, may further include an operation 912 for comparing the at least one sequential pattern to a second sequential pattern related to at least a second subjective user state associated with the user and a second objective occurrence to determine whether the at least one sequential pattern at least substantially matches with the second sequential pattern as depicted in FIG. 9. For instance, the sequential pattern comparison module 248 of the computing device 10 comparing the at least one sequential pattern to a second sequential pattern related to at least a previously reported second subjective user state associated with the user 20\* and a second previously reported objective occurrence to determine whether the at least one sequential pattern at least substantially matches with the second sequential pattern.

For these implementations, the comparison of the first sequential pattern to the second sequential pattern may involve making certain comparisons, For example, comparing the first subjective user state to the second subjective user state to determine at least whether they are the same or different types of subjective user states. Similarly, the first objective occurrence may be compared to the second objective occurrence to determine at least whether they are the same or different types of objective occurrences. The temporal relationship or the specific time sequencing between the incidence of the first subjective user state and the incidence of the first objective occurrence (e.g., as represented by the first sequential pattern) may then be compared to the temporal relationship or the specific time sequencing between the incidence of the second subjective user state and the incidence of the second objective occurrence (e.g., as represented by the second sequential pattern).

In some implementations, the correlation operation 808 of FIG. 8 may include an operation 914 for correlating the subjective user state data with the objective occurrence data at a server as depicted in FIG. 9. For instance, when the computing device 10 is a server (e.g., network server) and the correlation module 106 correlates the subjective user state data 60\* with the objective occurrence data 70\*.

In alternative implementations, the correlation operation 808 may include an operation 916 for correlating the subjective user state data with the objective occurrence data at a handheld device as depicted in FIG. 9. For instance, when the computing device 10 is a standalone device, such as a handheld device, and the correlation module 106 correlates the subjective user state data 60* with the objective occurrence data 70*.

In some implementations, the correlation operation 808 may include an operation 918 for correlating the subjective user state data with the objective occurrence data at a peer-to-peer network component device as depicted in FIG. 9. For instance, when the computing device 10 is a standalone device and is a peer-to-peer network component device, and the correlation module 106 correlates the subjective user state data 60* with the objective occurrence data 70*.

Figure 10:
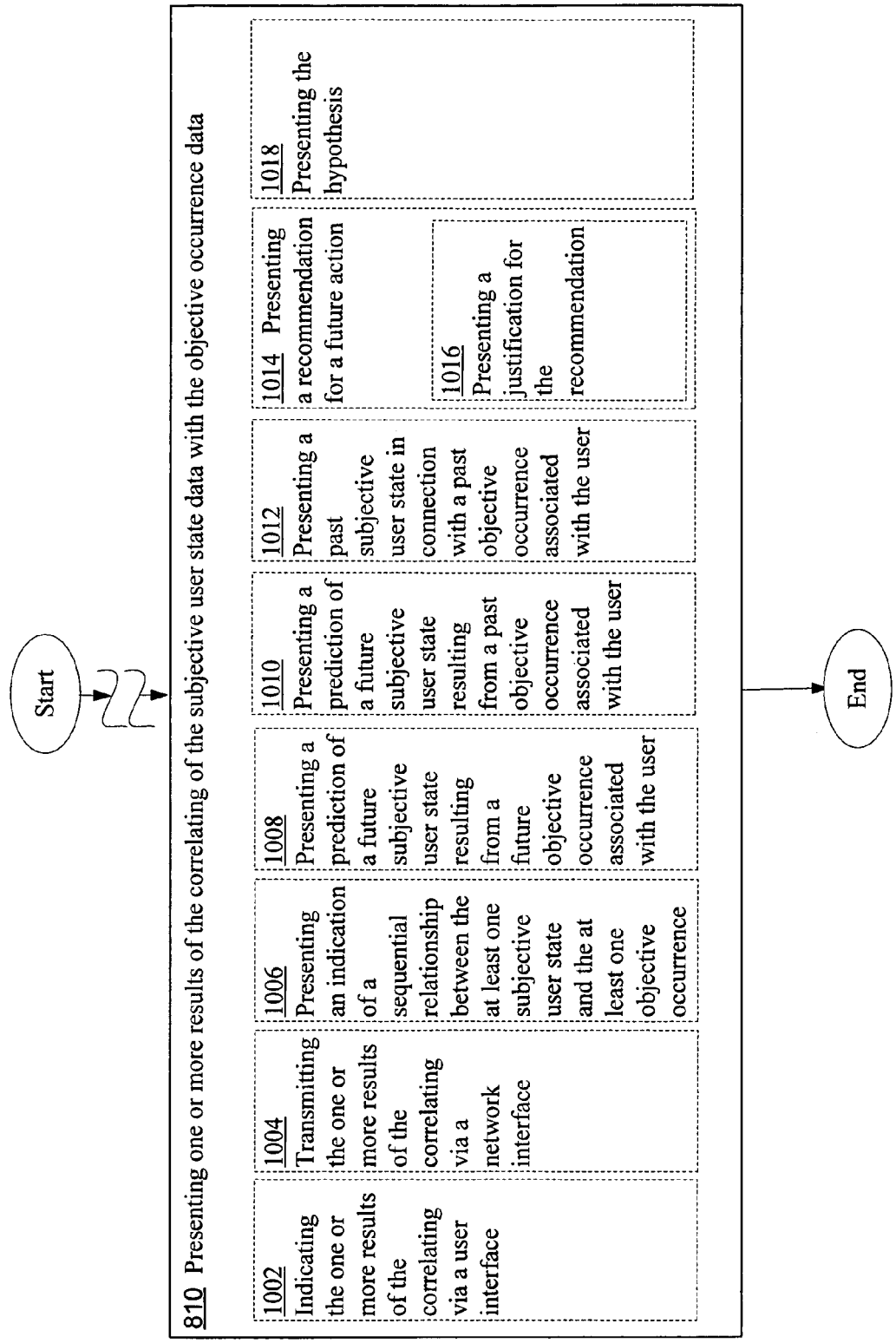
FIG. 10 is a high-level logic flowchart of a process depicting alternate implementations of the presentation operation 810 of FIG. 8.

Referring back to FIG. 8, the presentation operation 810 may include one or more additional operations in various alternative implementations. For example, in some implementations, the presentation operation 810 may include an operation 1002 for indicating the one or more results of the correlating via a user interface as depicted in FIG. 10. For instance, when the computing device 10 is a standalone device such as a handheld device (e.g., cellular telephone, a smartphone, an MID, an UMPC, a convergent device, and so forth) or other mobile devices, and the user interface indication module 259 of the computing device 10 indicates the one or more results of the correlation operation performed by the correlation module 106 via a user interface 122 (e.g., display monitor or audio system including a speaker).

In some implementations, the presentation operation 810 may include an operation 1004 for transmitting the one or more results of the correlating via a network interface as depicted in FIG. 10. For instance, when the computing device 10 is a server and the network interface transmission module 258 of the computing device 10 transmits the one or more results of the correlation operation performed by the correlation module 106 via a network interface 120 (e.g., NIC).

In some implementations, the presentation operation 810 may include an operation 1006 for presenting an indication of a sequential relationship between the at least one subjective user state and the at least one objective occurrence as depicted in FIG. 10. For instance, the sequential relationship presentation module 260 of the computing device 10 presenting (e.g., either by transmitting via the network interface 120 or by indicating via the user interface 122) an indication of a sequential relationship between the at least one subjective user state (e.g., happy) and the at least one objective occurrence (e.g., playing with children).

In some implementations, the presentation operation 810 may include an operation 1008 for presenting a prediction of a future subjective user state resulting from a future objective occurrence associated with the user as depicted in FIG. 10. For instance, the prediction presentation module 261 of the computing device 10 presenting (e.g., either by transmitting via the network interface 120 or by indicating via the user interface 122) a prediction of a future subjective user state associated with the user 20* resulting from a future objective occurrence (e.g., "if you drink the 24 ounces of beer you ordered, you will have a hangover tomorrow").

In some implementations, the presentation operation 810 may include an operation 1010 for presenting a prediction of a future subjective user state resulting from a past objective occurrence associated with the user as depicted in FIG. 10. For instance, the prediction presentation module 261 of the computing device 10 presenting (e.g., either by transmitting via the network interface 120 or by indicating via the user interface 122) a prediction of a future subjective user state associated with the user 20* resulting from a past objective occurrence (e.g., "you will have a stomach ache shortly because of the hot fudge sundae that you just ate").

In some implementations, the presentation operation 810 may include an operation 1012 for presenting a past subjective user state in connection with a past objective occurrence associated with the user as depicted in FIG. 10. For instance, the past presentation module 262 of the computing device 10 presenting (e.g., either by transmitting via the network interface 120 or by indicating via the user interface 122) a past subjective user state associated with the user 20* in connection with a past objective occurrence (e.g., "reason why you had a headache this morning may be because you drank that 24 ounces of beer last night").

In some implementations, the presentation operation 810 may include an operation 1014 for presenting a recommendation for a future action as depicted in FIG. 10. For instance, the recommendation module 263 of the computing device 10 presenting (e.g., either by transmitting via the network interface 120 or by indicating via the user interface 122) a recommendation for a future action (e.g., "you should buy something to calm your stomach tonight after you leave the bar tonight").

In some implementations, operation 1014 may further include an operation 1016 for presenting a justification for the recommendation as depicted in FIG. 10. For instance, the justification module 264 of the computing device 10 presenting (e.g., either by transmitting via the network interface 120 or by indicating via the user interface 122) a justification for the recommendation (e.g., "you should buy something to calm your stomach tonight since you are drinking beer tonight, and the last time you drank beer, you had an upset stomach the next morning").

In some implementations, the presentation operation 810 may include an operation 1018 for presenting the hypothesis as depicted in FIG. 10. For instance, the hypothesis presentation module 267 of the computing device 10 presenting (e.g., via the user interface 122 or via the network interface 120) the hypothesis 77 to, for example, the user 20* or to one or more third parties. Such an operation may be performed in some cases when the data indicating incidence of at least one objective occurrence 71* that was solicited is acquired and confirms or provides support for the hypothesis 77.

Figure 11:
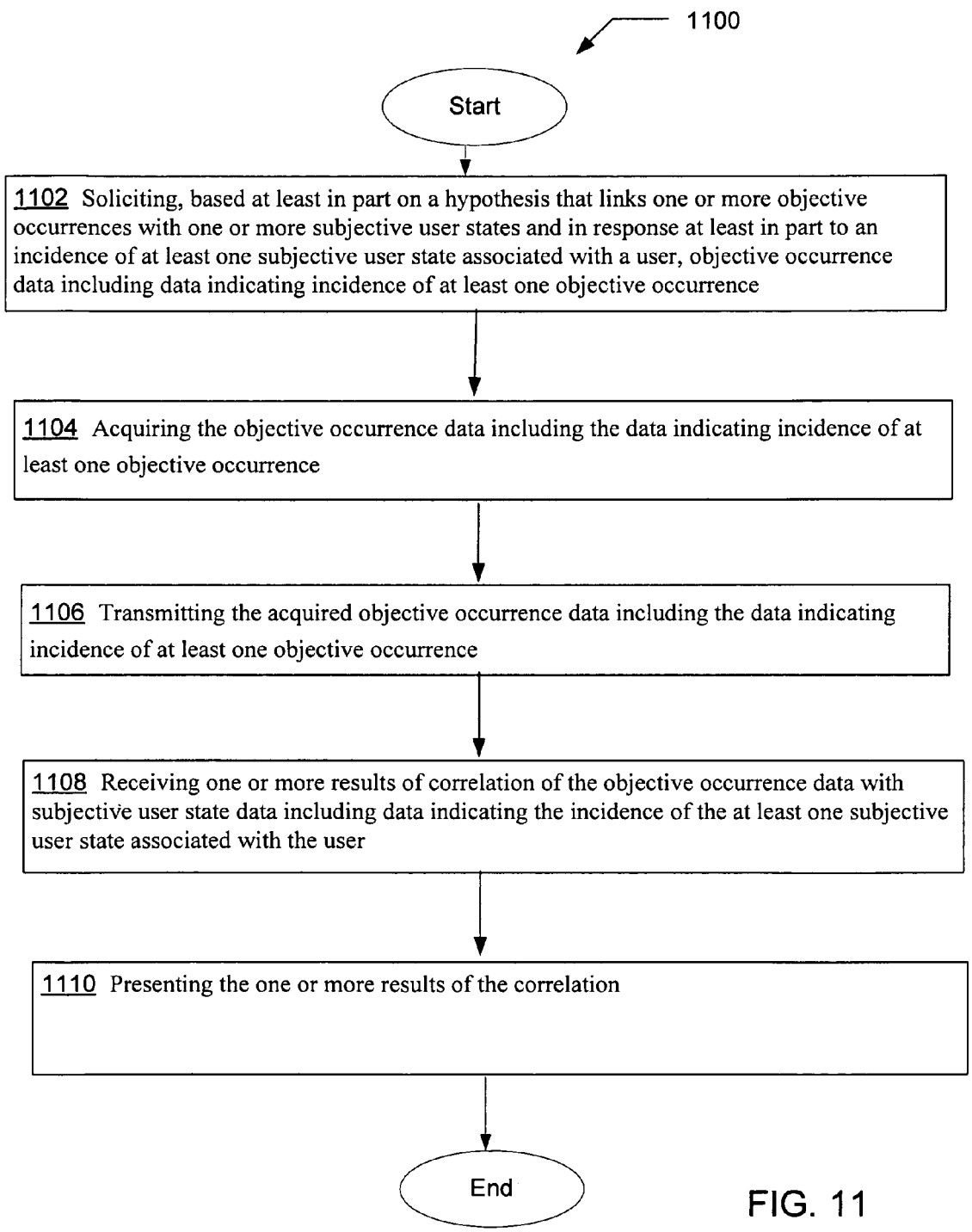
FIG. 11 is a high-level logic flowchart of still another process.

FIG. 11 illustrates another operational flow 1100 in accordance with various embodiments. In contrast to the previous operational flow 800, operational flow 1100 may be particularly suited to be performed by a mobile device 30 rather than by the computing device 10. Operational flow 1100 includes certain operations that may completely or substantially mirror certain operations included in the operational flow 800 of FIG. 8. For example, operational flow 1100 may include an objective occurrence data solicitation operation 1102, an objective occurrence data acquisition operation 1104, and a presentation operation 1110 that corresponds to and completely or substantially mirror the objective occurrence data solicitation operation 802, the objective occurrence data acquisition operation 804, and the presentation operation 810, respectively, of FIG. 8.

In addition, and unlike operational flow 800, operational flow 1100 may further include an objective occurrence data transmission operation 1106 for transmitting the acquired objective occurrence data including the data indicating incidence of at least one objective occurrence and a reception operation 1108 for receiving one or more results of correlation of the objective occurrence data with subjective user state data including data indicating the incidence of the at least one subjective user state associated with the user as depicted in FIG. 11. For example, the objective occurrence data transmission module 160 of the mobile device 30 transmitting (e.g., transmitting via at least one of the wireless network or wired network 40 to, for example, a network server such as computing device 10) the acquired objective occurrence data 70\* including the data indicating incidence of at least one objective occurrence 71\*. Note that the mobile device 30 may, itself, have originally acquired the data indicating incidence of at least one objective occurrence 71\* from the user 20*a*, from one or more sensors 35, or from one or more third party sources 50.

The correlation results reception module 162 of the mobile device 30 may then receive (e.g., receive from the computing device 10) one or more results of correlation of the subjective user state data 60*a* with objective occurrence data 70\* including data indicating the incidence of the at least one objective occurrence 71\*.

Figure 12:
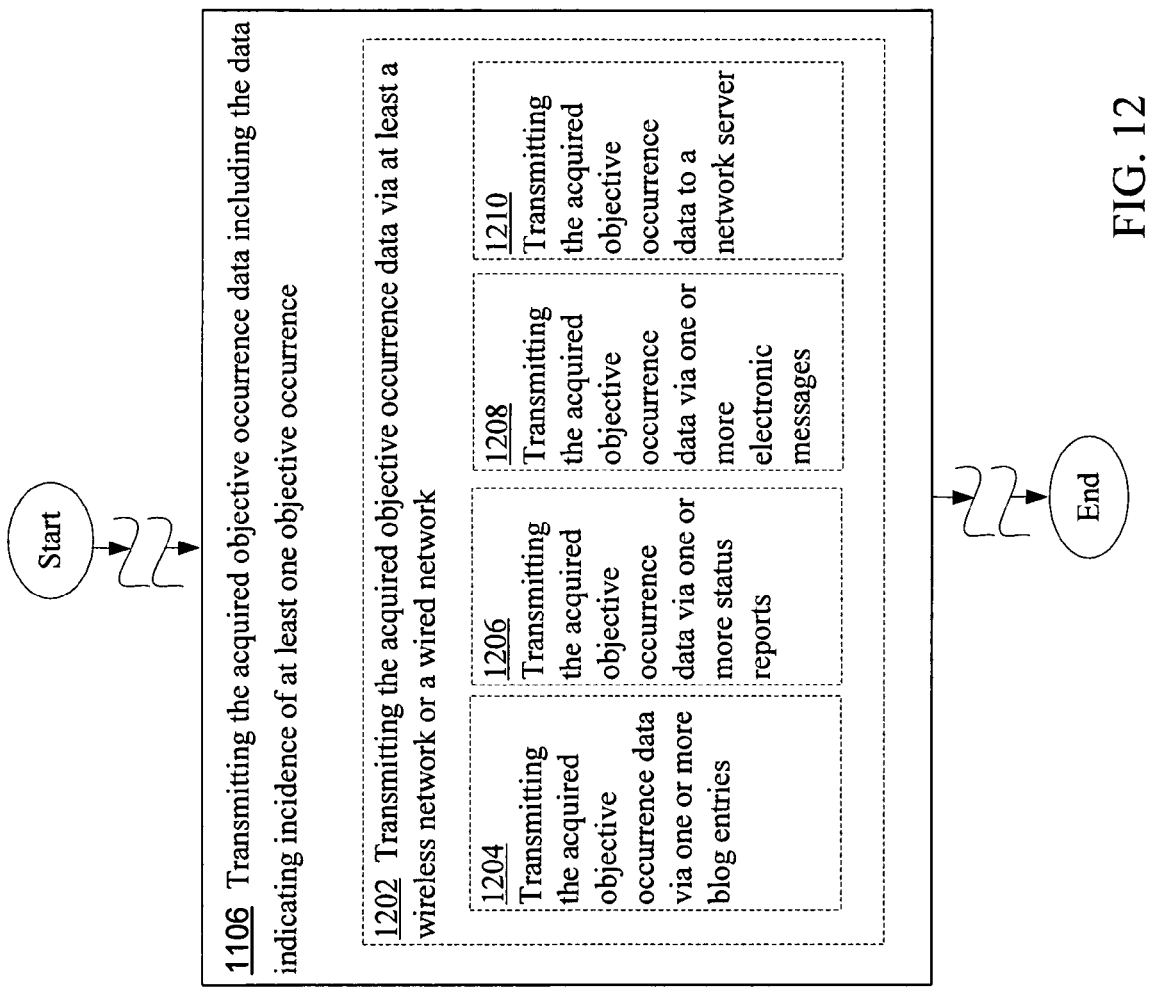
FIG. 12 is a high-level logic flowchart of a process depicting alternate implementations of the objective occurrence data transmission operation 1106 of FIG. 11.

In various alternative implementations, the objective occurrence data transmission operation 1106 may include one or more additional operations. For example, in some implementations, the objective occurrence data transmission operation 1106 may include an operation 1202 for transmitting the acquired objective occurrence data via at least a wireless network or a wired network as depicted in FIG. 12. For instance, the objective occurrence data transmission module 160 of the mobile device 30 transmitting the acquired objective occurrence data 70\* via at least one of a wireless network or a wired network 40.

In some implementations, operation 1202 may further include an operation 1204 for transmitting the acquired objective occurrence data via one or more blog entries as depicted in FIG. 12. For instance, the objective occurrence data transmission module 160 of the mobile device 30 transmitting the acquired objective occurrence data 70\* via one or more blog entries (e.g., microblog entries).

In some implementations, operation 1202 may include an operation 1206 for transmitting the acquired objective occurrence data via one or more status reports as depicted in FIG. 12. For instance, the objective occurrence data transmission module 160 of the mobile device 30 transmitting the acquired objective occurrence data 70\* via one or more status reports (e.g., social networking status reports).

In some implementations, operation 1202 may include an operation 1208 for transmitting the acquired objective occurrence data via one or more electronic messages as depicted in FIG. 12. For instance, the objective occurrence data transmission module 160 of the mobile device 30 transmitting the acquired objective occurrence data 70\* via one or more electronic messages (e.g., email message, IM messages, text messages, and so forth).

In some implementations, operation 1202 may include an operation 1210 for transmitting the acquired objective occurrence data to a network server as depicted in FIG. 12. For instance, the objective occurrence data transmission module 160 of the mobile device 30 transmitting the acquired objective occurrence data 70\* to a network server (e.g., computing device 10).

Figure 13:
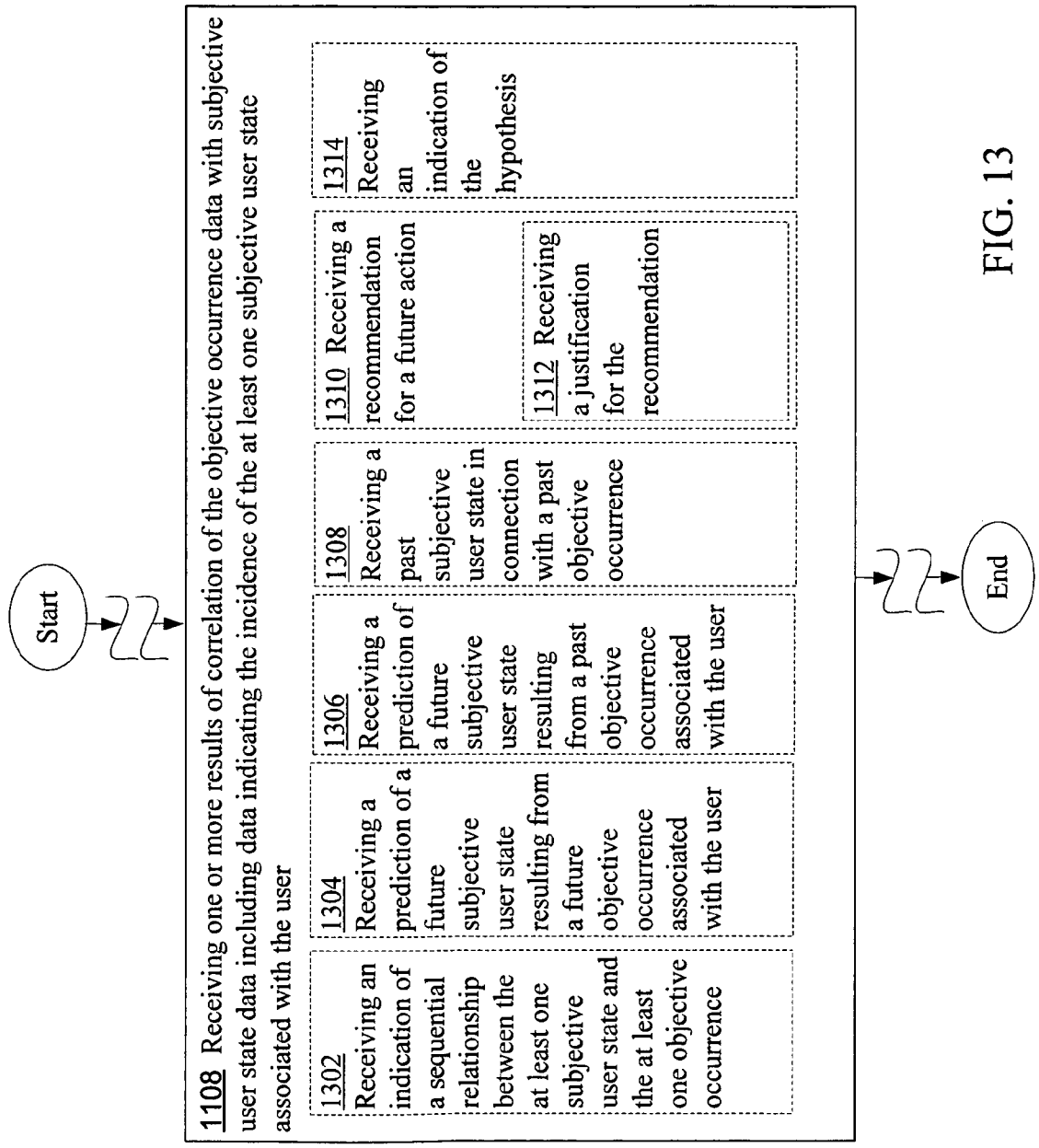
FIG. 13 is a high-level logic flowchart of a process depicting alternate implementations of the reception operation 1108 of FIG. 11.

Referring back to FIG. 11, the reception operation 1108 may include one or more additional operations in various alternative implementations. For example, in some implementations, the reception operation 1108 may include an operation 1302 for receiving an indication of a sequential relationship between the at least one subjective user state and the at least one objective occurrence as depicted in FIG. 13. For instance, the correlation results reception module 162 of the mobile device 30 receiving (e.g., via wireless network and/or wired network 40) at least an indication of a sequential relationship between the at least one subjective user state (e.g., as indicated by the data indicating incidence of at least one subjective user state 61*a*) and the at least one objective occurrence (e.g., as indicated by the data indicating incidence of at least one objective occurrence 71\*). For example, receiving an indication that the user 20*a* felt energized after jogging for thirty minutes.

In some implementations, the reception operation 1108 may include an operation 1304 for receiving a prediction of a future subjective user state resulting from a future objective occurrence associated with the user as depicted in FIG. 13. For instance, the correlation results reception module 162 of the mobile device 30 receiving (e.g., via wireless network and/or wired network 40) at least a prediction of a future subjective user state (e.g., feeling energized) associated with the user 20*a* resulting from a future objective occurrence (e.g., jogging for 30 minutes).

In some implementations, the reception operation 1108 may include an operation 1306 for receiving a prediction of a future subjective user state resulting from a past objective occurrence associated with the user as depicted in FIG. 13. For instance, the correlation results reception module 162 of the mobile device 30 receiving (e.g., via wireless network and/or wired network 40) at least a prediction of a future subjective user state (e.g., easing of pain) associated with the user 20*a* resulting from a past objective occurrence (e.g., previous ingestion of aspirin).

In some implementations, the reception operation 1108 may include an operation 1308 for receiving a past subjective user state in connection with a past objective occurrence as depicted in FIG. 13. For instance, the correlation results reception module 162 of the mobile device 30 receiving (e.g., via wireless network and/or wired network 40) at least an indication of a past subjective user state (e.g., depression) associated with the user 20*a* in connection with a past objective occurrence (e.g., overcast weather).

In some implementations, the reception operation 1108 may include an operation 1310 for receiving a recommendation for a future action as depicted in FIG. 13. For instance, the correlation results reception module 162 of the mobile device 30 receiving (e.g., via wireless network and/or wired network 40) at least a recommendation for a future action (e.g., "you should go to sleep early").

In certain implementations, operation 1310 may further include an operation 1312 for receiving a justification for the recommendation as depicted in FIG. 13. For instance, the correlation results reception module 162 of the mobile device 30 receiving (e.g., via wireless network and/or wired network 40) at least a justification for the recommendation (e.g., "last time you stayed up late, you were very tired the next morning").

In some implementations, the reception operation 1108 may include an operation 1314 for receiving an indication of the hypothesis as depicted in FIG. 13. For instance, the correlation results reception module 162 of the mobile device 30 receiving (e.g., via wireless network and/or wired network 40) an indication of the hypothesis 77. Such an operation may be performed when, for example, the objective occurrence data 70\* and the subjective user state data 60*a* supports the hypothesis 77.

Figure 14:
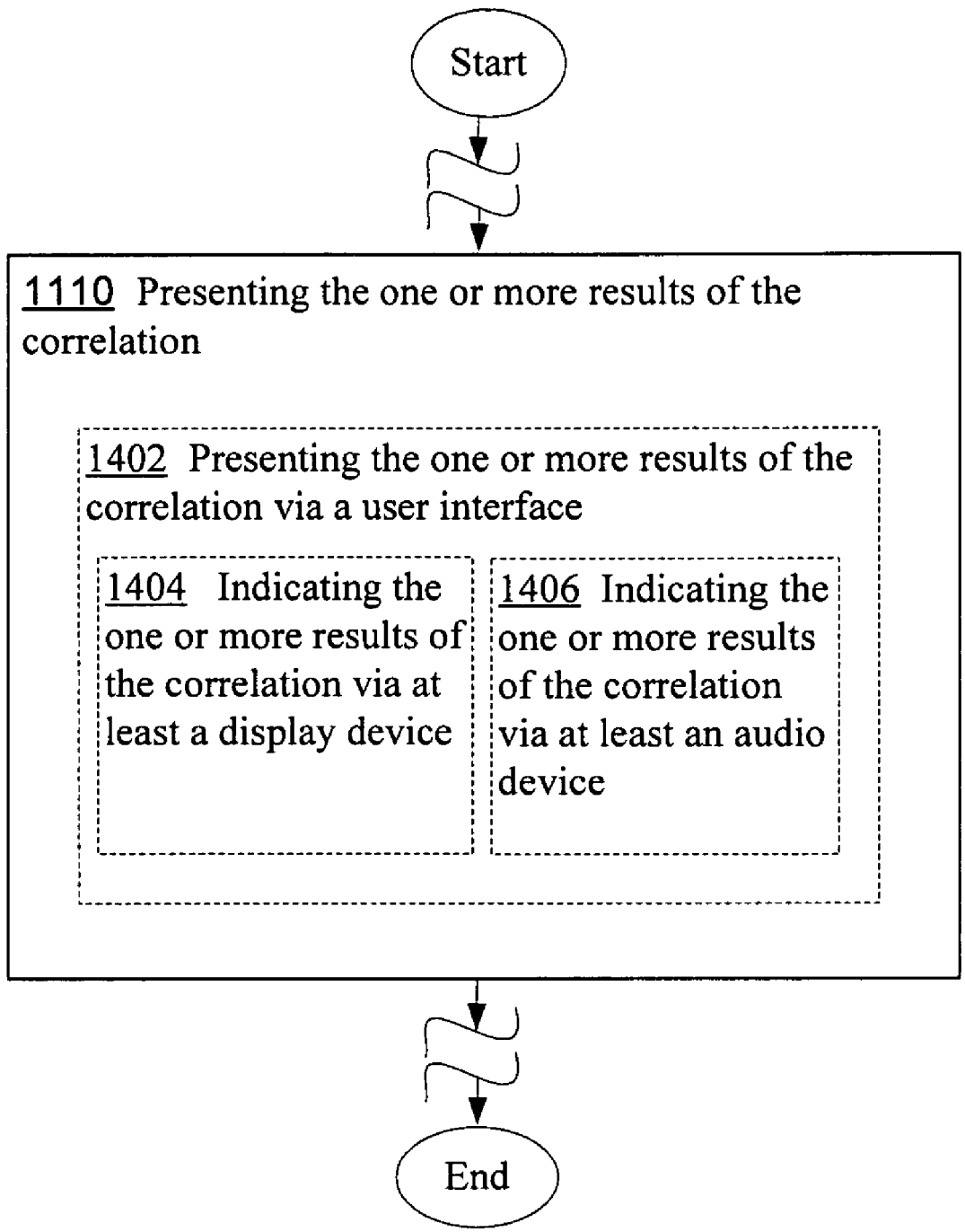
FIG. 14 is a high-level logic flowchart of a process depicting alternate implementations of the presentation operation 1110 of FIG. 11.

Referring back to FIG. 11, the process 1100 in various implementations may include a presentation operation 1110 to be performed by the mobile device 30 for presenting the one or more results of the correlation. For example, the presentation module 108' of the mobile device 30 presenting the one or more results of the correlation received by the correlation results reception module 162. As described earlier, the presentation operation 1110 of FIG. 11 in some implementations may completely or substantially mirror the presentation operation 810 of FIG. 8. For instance, in some implementations, the presentation operation 1110 may include, similar to the presentation operation 810 of FIG. 8, an operation 1402 for presenting the one or more results of the correlation via a user interface as depicted in FIG. 14. For instance, the user interface indication module 259' of the mobile device 30 indicating the one or more results of the correlation via a user interface 122' (e.g., an audio device including one or more speakers and/or a display device such as a LCD or a touchscreen).

In some implementations, operation 1402 may further include an operation 1404 for indicating the one or more results of the correlation via at least a display device as depicted in FIG. 14. For instance, the user interface indication module 259' of the mobile device 30 indicating the one or more results of the correlation via a display device (e.g., a display monitor such as a LCD or a touchscreen).

In some implementations, operation 1402 may include an operation 1406 for indicating the one or more results of the correlation via at least an audio device as depicted in FIG. 14. For instance, the user interface indication module 259' of the mobile device 30 indicating the one or more results of the correlation via an audio device (e.g., a speaker).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The invention claimed is:

1. A system in the form of a machine, article of manufacture, or composition of matter, comprising:
    an objective occurrence data solicitation module configured to solicit at least a portion of objective occurrence data including soliciting data indicating incidence of at least one objective occurrence, the solicitation being prompted based at least in part on a hypothesis linking one or more objective occurrences with one or more subjective user states and in response, at least in part, to an occurrence of at least one subjective user state associated with a user; and
    an objective occurrence data acquisition module configured to acquire the objective occurrence data, the objective occurrence data to be acquired including the data indicating incidence of at least one objective occurrence.

2. The system of claim 1, wherein said objective occurrence data solicitation module configured to solicit at least a portion of objective occurrence data including soliciting data indicating incidence of at least one objective occurrence, the solicitation being prompted based at least in part on a hypothesis linking one or more objective occurrences with one or more subjective user states and in response, at least in part, to an occurrence of at least one subjective user state associated with a user comprises:
    a requesting module configured to request for at least the portion of the objective occurrence data including the data indicating incidence of at least one objective occurrence from the user.

3. The system of claim 2, wherein said requesting module configured to request for at least the portion of the objective occurrence data including the data indicating incidence of at least one objective occurrence from the user comprises:
    a selection request module configured to request for a selection to be made by the user of an objective occurrence from a plurality of indicated alternative objective occurrences.

4. The system of claim 2, wherein said requesting module configured to request for at least the portion of the objective occurrence data including the data indicating incidence of at least one objective occurrence from the user comprises:
    a confirmation request module configured to request for a confirmation by the user of incidence of the at least one objective occurrence.

5. The system of claim 2, wherein said requesting module configured to request for at least the portion of the objective occurrence data including the data indicating incidence of at least one objective occurrence from the user comprises:

a motivation request module configured to provide a motivation for requesting for the request.

6. The system of claim 1, wherein said objective occurrence data solicitation module configured to solicit at least a portion of objective occurrence data including soliciting data indicating incidence of at least one objective occurrence, the data solicitation being prompted based at least in part on a hypothesis linking one or more objective occurrences with one or more subjective user states and in response, at least in part, to an occurrence of at least one subjective user state associated with a user comprises:

a requesting module configured to request from one or more third party sources the data indicating incidence of at least one objective occurrence.

7. The system of claim 6, wherein said requesting module configured to request from one or more third party sources the data indicating incidence of at least one objective occurrence comprises:

a confirmation request module configured to request for a confirmation of incidence of at least one objective occurrence by the one or more third party sources.

8. The system of claim 1, wherein said objective occurrence data solicitation module configured to solicit at least a portion of objective occurrence data including soliciting data indicating incidence of at least one objective occurrence, the solicitation being prompted based at least in part on a hypothesis linking one or more objective occurrences with one or more subjective user states and in response, at least in part, to an occurrence of at least one subjective user state associated with a user comprises:

a requesting module configured to request one or more remote devices to provide the data indicating incidence of at least one objective occurrence.

9. The system of claim 8, wherein said requesting module configured to request one or more remote devices to provide the data indicating incidence of at least one objective occurrence comprises:

a request transmission module configured to transmit to the one or more remote devices a request to be provided with the data indicating incidence of at least one objective occurrence.

10. The system of claim 8, wherein said requesting module configured to request one or more remote devices to provide the data indicating incidence of at least one objective occurrence comprises:

a request to access module configured to transmit a request to the one or more remote devices to have access to the data indicating incidence of at least one objective occurrence.

11. The system of claim 8, wherein said requesting module configured to request one or more remote devices to provide the data indicating incidence of at least one objective occurrence comprises:

a configuration module designed to configure one or more remote devices to provide the data indicating incidence of at least one objective occurrence.

12. The system of claim 8, wherein said requesting module configured to request one or more remote devices to provide the data indicating incidence of at least one objective occurrence comprises:

a directing/instructing module configured to direct or instruct one or more remote devices to provide the data indicating incidence of at least one objective occurrence.

13. The system of claim 8, wherein said requesting module configured to request one or more remote devices to provide the data indicating incidence of at least one objective occurrence comprises:

a requesting module configured to request one or more sensors to provide the data indicating incidence of at least one objective occurrence.

14. The system of claim 1, wherein said objective occurrence data solicitation module configured to solicit at least a portion of objective occurrence data including soliciting data indicating incidence of at least one objective occurrence, the solicitation being prompted based at least in part on a hypothesis linking one or more objective occurrences with one or more subjective user states and in response, at least in part, to an occurrence of at least one subjective user state associated with a user comprises:

an objective occurrence data solicitation module including a hypothesis reference module, the objective occurrence data solicitation module configured to solicit data indicating incidence of at least one objective occurrence based, at least in part, on the hypothesis reference module referencing the hypothesis.

15. The system of claim 14, wherein said objective occurrence data solicitation module including a hypothesis reference module, the objective occurrence data solicitation module configured to solicit data indicating incidence of at least one objective occurrence based, at least in part, on the hypothesis reference module referencing the hypothesis comprises:

a hypothesis reference module configured to reference a hypothesis that identifies one or more temporal relationships between the one or more objective occurrences and the one or more subjective user states.

16. The system of claim 15, wherein said hypothesis reference module configured to reference a hypothesis that identifies one or more temporal relationships between the one or more objective occurrences and the one or more subjective user states comprises:

a hypothesis reference module configured to reference a hypothesis that identifies one or more time sequential relationships between the at least one subjective user state and the one or more objective occurrences.

17. The system of claim 14, wherein said objective occurrence data solicitation module including a hypothesis reference module, the objective occurrence data solicitation module configured to solicit data indicating incidence of at least one objective occurrence based, at least in part, on the hypothesis reference module referencing the hypothesis comprises:

a hypothesis reference module configured to reference a hypothesis that identifies a relationship between at least an ingestion of a medicine and the one or more subjective user states.

18. The system of claim 14, wherein said objective occurrence data solicitation module including a hypothesis reference module, the objective occurrence data solicitation module configured to solicit data indicating incidence of at least one objective occurrence based, at least in part, on the hypothesis reference module referencing the hypothesis comprises:

a hypothesis reference module configured to reference a hypothesis that identifies a relationship between at least an ingestion of a food item and the one or more subjective user states.

19. The system of claim 14, wherein said objective occurrence data solicitation module including a hypothesis reference module, the objective occurrence data solicitation module configured to solicit data indicating incidence of at least one objective occurrence based, at least in part, on the hypothesis reference module referencing the hypothesis comprises:

a hypothesis reference module configured to reference a hypothesis that identifies a relationship between at least an ingestion of a nutraceutical and the one or more subjective user states.

20. The system of claim 14, wherein said objective occurrence data solicitation module including a hypothesis reference module, the objective occurrence data solicitation module configured to solicit data indicating incidence of at least one objective occurrence based, at least in part, on the hypothesis reference module referencing the hypothesis comprises:
a hypothesis reference module configured to reference a hypothesis that identifies a relationship between execution of one or more exercise routines and the one or more subjective user states.

21. The system of claim 14, wherein said objective occurrence data solicitation module including a hypothesis reference module, the objective occurrence data solicitation module configured to solicit data indicating incidence of at least one objective occurrence based, at least in part, on the hypothesis reference module referencing the hypothesis comprises:
a hypothesis reference module configured to reference a hypothesis that identifies a relationship between execution of one or more social activities and the one or more subjective user states.

22. The system of claim 14, wherein said objective occurrence data solicitation module including a hypothesis reference module, the objective occurrence data solicitation module configured to solicit data indicating incidence of at least one objective occurrence based, at least in part, on the hypothesis reference module referencing the hypothesis comprises:
a hypothesis reference module configured to reference a hypothesis that identifies a relationship between execution of one or more activities executed by a third party and the one or more subjective user states.

23. The system of claim 14, wherein said objective occurrence data solicitation module including a hypothesis reference module, the objective occurrence data solicitation module configured to solicit data indicating incidence of at least one objective occurrence based, at least in part, on the hypothesis reference module referencing the hypothesis comprises:
a hypothesis reference module configured to reference a hypothesis that identifies a relationship between one or more physical characteristics of the user and the one or more subjective user states.

24. The system of claim 14, wherein said objective occurrence data solicitation module including a hypothesis reference module, the objective occurrence data solicitation module configured to solicit data indicating incidence of at least one objective occurrence based, at least in part, on the hypothesis reference module referencing the hypothesis comprises:
a hypothesis reference module configured to reference a hypothesis that identifies a relationship between a resting, a learning, or a recreational activity performed by the user and the one or more subjective user states.

25. The system of claim 14, wherein said objective occurrence data solicitation module including a hypothesis reference module, the objective occurrence data solicitation module configured to solicit data indicating incidence of at least one objective occurrence based, at least in part, on the hypothesis reference module referencing the hypothesis comprises:
a hypothesis reference module configured to reference a hypothesis that identifies a relationship between one or more external activities and the one or more subjective user states.

26. The system of claim 14, wherein said objective occurrence data solicitation module including a hypothesis reference module, the objective occurrence data solicitation module configured to solicit data indicating incidence of at least one objective occurrence based, at least in part, on the hypothesis reference module referencing the hypothesis comprises:
a hypothesis reference module configured to reference a hypothesis that identifies a relationship between one or more locations of the user and the one or more subjective user states.

27. The system of claim 1, wherein said objective occurrence data solicitation module configured to solicit at least a portion of objective occurrence data including soliciting data indicating incidence of at least one objective occurrence, the solicitation being prompted based at least in part on a hypothesis linking one or more objective occurrences with one or more subjective user states and in response, at least in part, to an occurrence of at least one subjective user state associated with a user comprises:
an objective occurrence data solicitation module configured to solicit data indicating incidence of at least one objective occurrence in response to a reception to a request to solicit the data indicating incidence of at least one objective occurrence, the request to solicit being remotely generated based, at least in part, on the hypothesis.

28. The system of claim 27, wherein said objective occurrence data solicitation module configured to solicit data indicating incidence of at least one objective occurrence in response to a reception to a request to solicit the data indicating incidence of at least one objective occurrence, the request to solicit being remotely generated based, at least in part, on the hypothesis comprises:
an objective occurrence data solicitation module configured to solicit data indicating incidence of at least one objective occurrence in response to a request to solicit reception module receiving a request to solicit the data indicating incidence of at least one objective occurrence, the request to solicit being remotely generated based, at least in part, on the hypothesis and based and in response to the incidence of the at least one subjective user state associated with the user.

29. The system of claim 1, wherein said objective occurrence data solicitation module configured to solicit at least a portion of objective occurrence data including soliciting data indicating incidence of at least one objective occurrence, the solicitation being prompted based at least in part on a hypothesis linking one or more objective occurrences with one or more subjective user states and in response, at least in part, to an occurrence of at least one subjective user state associated with a user comprises:
an objective occurrence data solicitation module configured to solicit the data indicating incidence of at least one objective occurrence in response, at least in part, to a subjective user state data reception module receiving data indicating incidence of the at least one subjective user state associated with the user.

30. The system of claim 29, wherein said objective occurrence data solicitation module configured to solicit the data indicating incidence of at least one objective occurrence in response, at least in part, to a subjective user state data reception module receiving data indicating incidence of the at least one subjective user state associated with the user comprises:
an objective occurrence data solicitation module configured to solicit the data indicating incidence of at least one objective occurrence in response, at least in part, to a subjective user state data reception module receiving, via one or more blog entries, the data indicating incidence of the at least one subjective user state associated with the user.

31. The system of claim 29, wherein said objective occurrence data solicitation module configured to solicit the data indicating incidence of at least one objective occurrence in response, at least in part, to a subjective user state data reception module receiving data indicating incidence of the at least one subjective user state associated with the user comprises:
an objective occurrence data solicitation module configured to solicit the data indicating incidence of at least one objective occurrence in response, at least in part, to a subjective user state data reception module receiving, via one or more status reports, the data indicating incidence of the at least one subjective user state associated with the user.

32. The system of claim 29, wherein said objective occurrence data solicitation module configured to solicit the data indicating incidence of at least one objective occurrence in response, at least in part, to a subjective user state data reception module receiving data indicating incidence of the at least one subjective user state associated with the user comprises:
an objective occurrence data solicitation module configured to solicit the data indicating incidence of at least one objective occurrence in response, at least in part, to a subjective user state data reception module receiving, via one or more electronic messages, the data indicating incidence of the at least one subjective user state associated with the user.

33. The system of claim 29, wherein said objective occurrence data solicitation module configured to solicit the data indicating incidence of at least one objective occurrence in response, at least in part, to a subjective user state data reception module receiving data indicating incidence of the at least one subjective user state associated with the user comprises:
an objective occurrence data solicitation module configured to solicit the data indicating incidence of at least one objective occurrence in response, at least in part, to a subjective user state data reception module receiving from the user the data indicating incidence of the at least one subjective user state associated with the user.

34. The system of claim 1, wherein said objective occurrence data acquisition module configured to acquire the objective occurrence data, the objective occurrence data to be acquired including the data indicating incidence of at least one objective occurrence comprises:
an objective occurrence data reception module configured to receive at least the data indicating incidence of at least one objective occurrence.

35. The system of claim 34, wherein said objective occurrence data reception module configured to receive at least the data indicating incidence of at least one objective occurrence comprises:
an objective occurrence data reception module configured to receive, via one or more blog entries, the data indicating incidence of at least one objective occurrence.

36. The system of claim 34, wherein said objective occurrence data reception module configured to receive at least the data indicating incidence of at least one objective occurrence comprises:
an objective occurrence data reception module configured to receive, via one or more status reports, the data indicating incidence of at least one objective occurrence.

37. The system of claim 34, wherein said objective occurrence data reception module configured to receive at least the data indicating incidence of at least one objective occurrence comprises:
an objective occurrence data reception module configured to receive, via one or more electronic messages, the data indicating incidence of at least one objective occurrence.

38. The system of claim 1, further comprising:
a subjective user state data acquisition module configured to acquire subjective user state data, the acquired subjective user state data including data indicating incidence of the at least one subjective user state associated with the user.

39. The system of claim 38, wherein said subjective user state data acquisition module configured to acquire subjective user state data, the acquired subjective user state data including data indicating incidence of the at least one subjective user state associated with the user comprises:
a subjective user state data reception module configured to receive the subjective user state data including the data indicating incidence of the at least one subjective user state associated with the user.

40. The system of claim 39, wherein said subjective user state data reception module configured to receive the subjective user state data including the data indicating incidence of the at least one subjective user state associated with the user comprises:
a subjective user state data reception module configured to receive, via one or more blog entries, the subjective user state data.

41. The system of claim 39, wherein said subjective user state data reception module configured to receive the subjective user state data including the data indicating incidence of the at least one subjective user state associated with the user comprises:
a subjective user state data reception module configured to receive, via one or more status reports, the subjective user state data.

42. The system of claim 39, wherein said subjective user state data reception module configured to receive the subjective user state data including the data indicating incidence of the at least one subjective user state associated with the user comprises:
a subjective user state data reception module configured to receive, via one or more electronic messages, the subjective user state data.

43. The system of claim 38, wherein said subjective user state data acquisition module configured to acquire subjective user state data, the acquired subjective user state data including data indicating incidence of the at least one subjective user state associated with the user comprises:
a time stamp acquisition module configured to receive a time stamp associated with the incidence of the at least one subjective user state.

44. The system of claim 38, wherein said subjective user state data acquisition module configured to acquire subjective user state data, the acquired subjective user state data including data indicating incidence of the at least one subjective user state associated with the user comprises:
a time interval acquisition module configured to acquire an indication of a time interval associated with the incidence of the at least one subjective user state.

45. A computationally-implemented system, comprising:
circuitry for soliciting at least a portion of objective occurrence data including soliciting data indicating incidence of at least one objective occurrence, the solicitation being prompted based at least in part on a hypothesis linking one or more objective occurrences with one or more subjective user states and in response, at least in part, to an occurrence of at least one subjective user state associated with a user; and circuitry for acquiring the objective occurrence data, the objective occurrence data to be acquired including the data indicating incidence of at least one objective occurrence.

46. An article of manufacture, comprising:

a non-transitory signal-bearing medium bearing:

one or more instructions for soliciting at least a portion of objective occurrence data including soliciting data indicating incidence of at least one objective occurrence, the solicitation being prompted based at least in part on a hypothesis linking one or more objective occurrences with one or more subjective user states and in response, at least in part, to an occurrence of at least one subjective user state associated with a user; and one or more instructions for acquiring the objective occurrence data, the objective occurrence data to be acquired including the data indicating incidence of at least one objective occurrence.

\* \* \* \* \*